(12) United States Patent
Sasada

(10) Patent No.: US 9,309,463 B2
(45) Date of Patent: Apr. 12, 2016

(54) LIQUID CRYSTAL COMPOUND, LIQUID CRYSTAL COMPOSITION AND LIQUID CRYSTAL DISPLAY DEVICE

(71) Applicant: Yasuyuki Sasada, Ichihara (JP)

(72) Inventor: Yasuyuki Sasada, Ichihara (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 40 days.

(21) Appl. No.: 14/023,044

(22) Filed: Sep. 10, 2013

(65) Prior Publication Data

US 2014/0077131 A1    Mar. 20, 2014

(30) Foreign Application Priority Data

Sep. 11, 2012  (JP) ................. 2012-199053

(51) Int. Cl.
| | |
|---|---|
| *C09K 19/12* | (2006.01) |
| *C09K 19/14* | (2006.01) |
| *C09K 19/16* | (2006.01) |
| *C09K 19/18* | (2006.01) |
| *C09K 19/20* | (2006.01) |
| *C09K 19/30* | (2006.01) |
| *C07C 43/20* | (2006.01) |
| *C09K 19/04* | (2006.01) |

(52) U.S. Cl.
CPC ............. *C09K 19/3066* (2013.01); *C07C 43/20* (2013.01); *C09K 19/12* (2013.01); *C09K 19/14* (2013.01); *C09K 19/16* (2013.01); *C09K 19/18* (2013.01); *C09K 19/20* (2013.01); *C09K 19/3001* (2013.01); *C09K 2019/0459* (2013.01); *C09K 2019/0466* (2013.01); *C09K 2019/0481* (2013.01)

(58) Field of Classification Search
CPC .... C09K 19/12; C09K 19/18; C09K 19/3001; C09K 19/3066; C09K 2019/0459; C09K 2019/0466; C09K 2019/0481; C07C 43/20; C07C 43/2005; C07C 43/23
See application file for complete search history.

(56) References Cited

PUBLICATIONS

Martin Schadt et al., "Material Properties, Structural Relations with Molecular Ensembles and Electro-Optical Performance of New Bicyclohexane Liquid Crystals in Field-Effect Liquid Crystal Displays," Liquid Crystals, 1989, vol. 5, No. 1, pp. 293-312.

A.J. Jin et al., "Highly Anisotropic Elasticity of a Dendrimeric Liquid Crystal," European Physical Journal B, vol. 5, pp. 251-255, (1998).
Seishi Shibayama et al., "Enlargement of Temperature Range in Liquid Crystalline Blue Phases by Novel Dendritic Molecules," 2010 Preprints of Symposium on Liquid Crystals, Japan, 2010.
T. Ishihara et al., "An Efficient Generation of the Aluminum Enolates of 1H-Perfluroalkyl Ketones from 1-Substituted-1-perflurouoalkenyl Phosphates and Their Aldol Reaction with Aldehydes," Journal of Organic Chemistry, 55 (10), 3107-3114(1990).
Z. Zhu et al., "Synthesis of 1,3,5-Trioxanes: Catalyic Cyclotrimerization of Aldehydes," Synthesis, 4, 417-422 (1998).
D. Pini et al., "Enantioselective Synthesis and CD Assignment of Absolute Configuration of (–)-1,3-Diphenylpropane-1,3-Diol," Asymmetry, 6(5), 1031-1034 (1995).

*Primary Examiner* — Shean C Wu
(74) *Attorney, Agent, or Firm* — Hogan Lovells US LLP

(57) ABSTRACT

The invention provides a liquid crystal compound represented by formula (1):

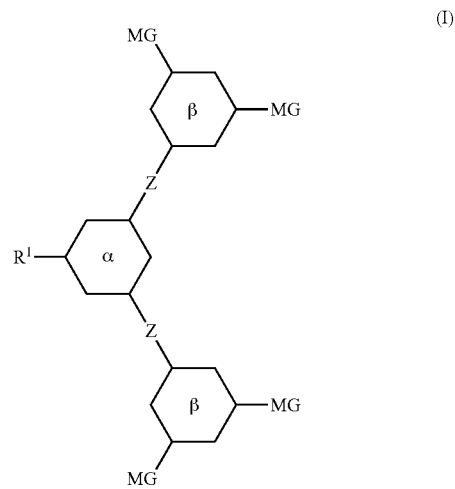

wherein, in formula (I), for example, $R^1$ is fluorine, chlorine, or alkyl having 1 to 10 carbons, and in the alkyl, at least one of —$CH_2$— may be replaced by —O—, —S—, —CO— or —$SiH_2$—, and at least one of —$(CH_2)_2$— may be replaced by —CH=CH— or —C≡C—. The compound has a low threshold voltage and excellent compatibility with other liquid crystal compounds, and further excellent general physical properties required for the compound. The invention also provides a liquid crystal composition containing at least one of the compounds and having excellent properties, and a liquid crystal display device including the composition, and having a wide usable temperature range, a short response time, a large contrast ratio and a low driving voltage, and therefore can be used for a liquid crystal projector and a liquid crystal television.

23 Claims, No Drawings

LIQUID CRYSTAL COMPOUND, LIQUID CRYSTAL COMPOSITION AND LIQUID CRYSTAL DISPLAY DEVICE

This is a Non-Provisional application, which claims priority to Japanese Patent Application No. 2012-199053, filed on Sep. 11, 2012; the contents of which are all herein incorporated by this reference in their entireties. All publications, patents, patent applications, databases and other references cited in this application, all related applications referenced herein, and all references cited therein, are incorporated by reference in their entirety as if restated here in full and as if each individual publication, patent, patent application, database or other reference were specifically and individuality indicated to be incorporated by reference.

TECHNICAL FIELD

The present invention relates to a liquid crystal compound, a liquid crystal composition and a liquid crystal display device. More specifically, the invention relates to a dendron compound, a liquid crystal composition containing the same and having a nematic phase, and a liquid crystal display device including the composition.

BACKGROUND ART

A liquid crystal display device typified by a liquid crystal display panel, a liquid crystal display module or the like utilizes optical anisotropy, dielectric anisotropy or the like of a liquid crystal compound. As an operating mode of the liquid crystal display device, various modes are known, such as a phase change (PC) mode, a twisted nematic (TN) mode, a super twisted nematic (STN) mode, a bistable twisted nematic (BTN) mode, an electrically controlled birefringence (ECB) mode, an optically compensated bend (OCB) mode, an in-plane switching (IPS) mode, a vertical alignment (VA) mode and a polymer sustained alignment (PSA) mode.

Without regard to use according to any mode, any liquid crystal material requires, as common properties, the following characteristics:

1) being stable to external environment factors such as moisture, air, heat and light;
2) exhibiting a liquid crystal phase in a wide temperature range centering on room temperature;
3) having a low viscosity;
4) allowing a decrease of driving voltage when driving a display device;
5) having an optimum dielectric anisotropy ($\Delta\in$); and
6) having an optimum refractive index anisotropy ($\Delta n$).

CITATION LIST

Non-Patent Literature

Non-patent literature No. 1: MARTINE SCHADT et al., Material properties, structural relations with molecular ensembles and electro-optical performance of new bicyclohexane liquid crystals in field-effect liquid crystal displays, LIQUID CRYSTAL, (Great Britain), Taylor & Frances Ltd, 1989, Vol. 5, No. 1, pp. 293-312.

Non-patent literature No. 2: A. J. Jin, C. Rosenblatt et al., Highly anisotropic elasticity of a dendrimeric liquid crystal, The European Physical Journal B, EDP Sciences Springer-Verlag, 1998, Vol. 5, pp. 251-255.

Non-patent literature No. 3: Seishi Shibayama, Hiroki Higuchi, Hirotsugu Kikuch, 2010 Preprints of Symposium on Liquid Crystals (The Japanese Liquid Crystal Society) (2010 Nen Nihon Ekisho Gakkai Toronkai Yokoshu in Japanese), Japan, 2010, 2b11.

Then, various kinds of research have been conducted on structures of compounds useful as a liquid crystal material. For example, Non-patent literature No. 1 describes a relationship between a molecular structure of bicyclohexane that is represented by structure formula (A) below and has a double bond in a terminal part of an alkenyl side chain, and characteristics thereof as a liquid crystal material. However, as the characteristics as the liquid crystal material, mere response speed is specifically researched.

Non-patent literature No. 2 describes a dendrimer represented by structure formula (B) below as a liquid crystal material. However, such a dendrimeric compound is a huge molecule, and has a large viscosity, and therefore has lacked practical applicability.

Formula 1

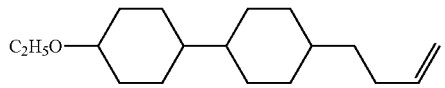

(A)

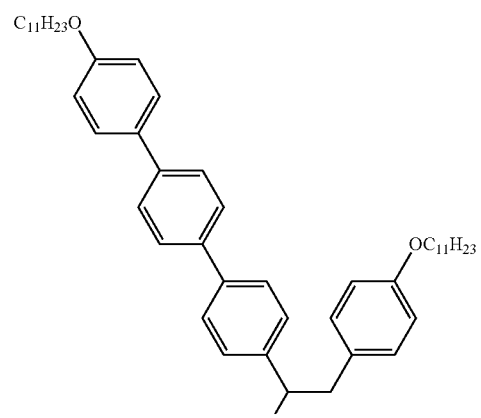

(B)

-continued

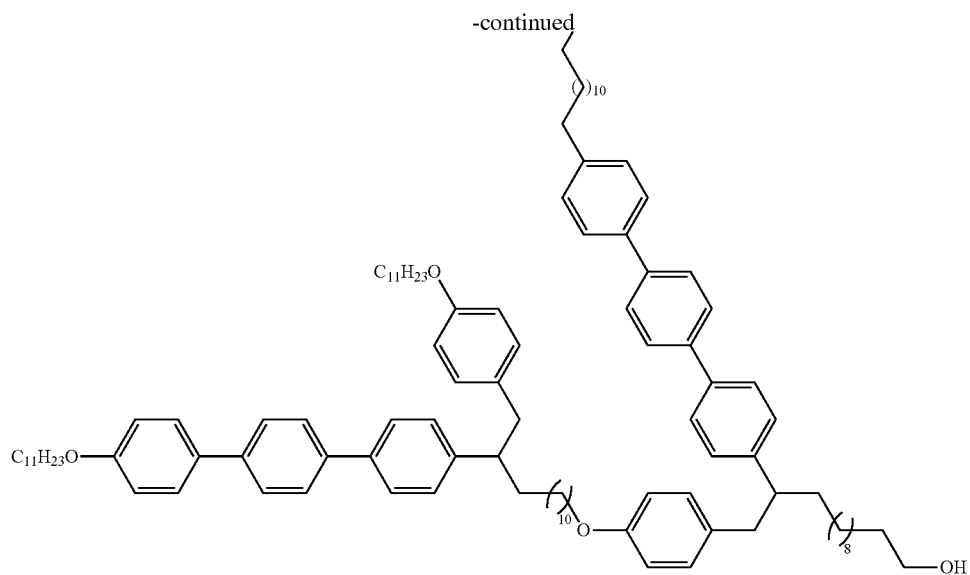

Non-patent literature No. 3 reports a dendrimeric compound represented by structure formula (C) below as a liquid crystal material. However, the compound has a terminal cyano group, and thus has had a problem of exerting effect only in a liquid crystal composition containing a cyano-based liquid crystal material.

Thus, a liquid crystal compound satisfying all of the characteristics 1 to 6 has not been found out. Therefore, as a liquid crystal composition prepared by mixing several kinds to twenty or more kinds of liquid crystal compounds, the liquid crystal composition being the mixture is used for a liquid crystal display device under a current situation. Therefore, a Formula 2

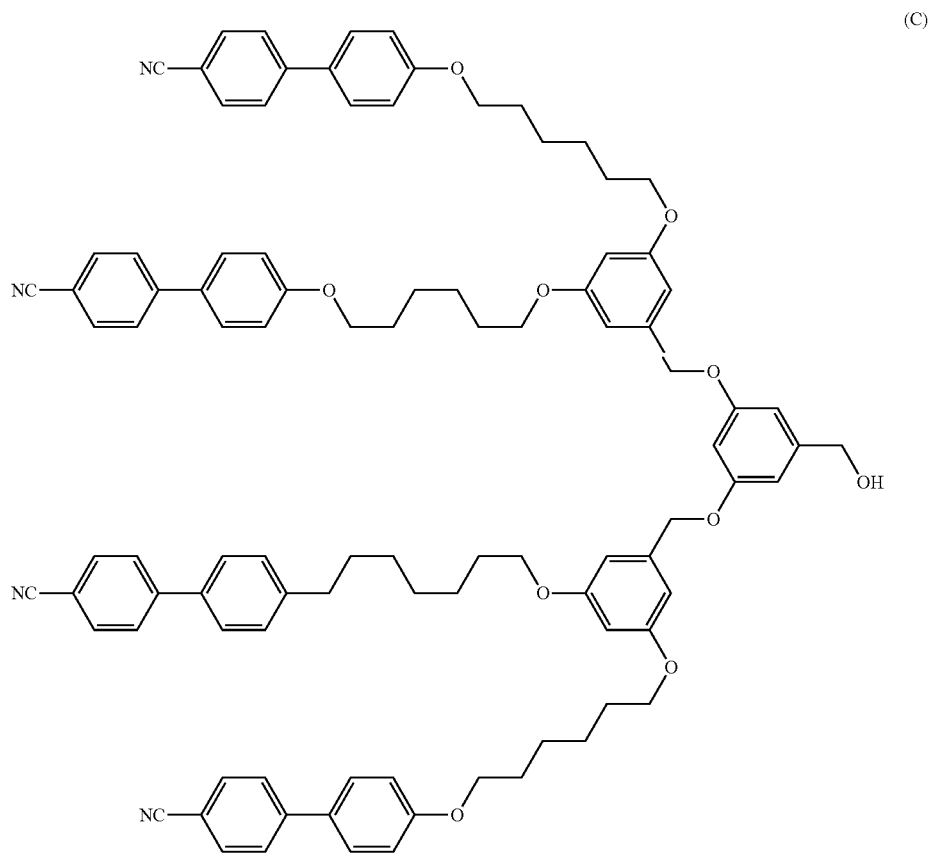

(C)

liquid crystal material is also required to have the following characteristics:

7) a liquid crystal compound, used as a composition component exhibiting good compatibility with other components.

Furthermore, a liquid crystal display device having a higher level of display performance in contrast, display capacity, response time and so forth has been recently required. In order to meet the requirement, a demand for a display device according to an active matrix mode typified by a thin film transistor (TFT) mode is increasing mainly in a field of a television, a viewfinder or the like. With regard to a display device according to an STN mode, a manufacturing process is simple and cost is low, while the display device has a large display capacity. Thus, such a display device is frequently used in a display field such as a cell phone and a personal computer. Moreover, as a mode overcoming a limited viewing angle as the largest problem of a liquid crystal display device, a new mode such as an in-plane switching (IPS) mode, a vertical alignment (VA) mode, a multi-domain vertical alignment (MVA) mode and an OCB mode has been recently disclosed. Threshold voltage or an elastic constant influencing response speed is different for each mode. Among the modes, the IPS mode is particularly excellent in viewing angle characteristics, and also has a high contrast, and therefore has been actively developed by each display manufacturer. As a recent development trend in the fields, as seen in a portable terminal including a smartphone, a personal computer according to a tablet mode to be portable due to size reduction and weight reduction, the development has been advanced centering on size reduction and achievement of a portable display.

In order to satisfy a demand for an improvement in performance, size reduction, achievement of the portable terminal for liquid crystal display equipment in recent years, the liquid crystal material is also required, in addition to the characteristics described above, to have the following characteristics:

8) low threshold voltage (driving voltage required for a liquid crystal display).

However, a liquid crystal compound satisfying the characteristics 1 to 8 in a wide range has not been obtained yet.

An object of the invention is to eliminate a defect of a conventional technology as described above, and is to provide a liquid crystal compound allowing low voltage drive and high speed response according to various display modes, and a liquid crystal composition using the liquid crystal compound, and a liquid crystal display device using the liquid crystal composition.

Solution to Problem

The present inventors have diligently continued to conduct research for achieving the object described above, as a result, succeeded in manufacturing a new liquid crystal compound represented by formula (I) and having at the terminal a mesogen having neither fluorine substituent nor polar substituent. Then, the present inventors have found that, if the liquid crystal compound of the invention is used, an excellent liquid crystal composition and liquid crystal display device responding to various operating modes can be obtained.

More specifically, a constitution of the invention is as described below.

Item 1. A compound represented by formula (I).

Here, a description on a substituent herein will be explained in advance. First, when a position of group A is not limited to one in a general formula, the position of group A can be selected without any limitation. When only one of A is present in a formula, A may have any position, if the position is chemically allowed. When a plurality of A are present in a formula, A may have each independently any position, if the position is chemically allowed.

Next, an expression "at least one" or "may be replaced" will be explained. For example, according to a comment "at least one of A may be replaced by B," if only one of A is present in a general formula corresponding to the comment, as group A, any of a case where group A is replaced by group B and a case where group A is not replaced by group B is allowed. If a plurality of A are present in a general formula corresponding to the comment, any of a case where any one of group A is replaced by group B, a case where some of group A is replaced by group B, and a case where all of group A are replaced by group B is allowed. Accordingly, for example, according to a comment "at least one of A may be replaced by B or C," if only one of A is present in a general formula in response to the comment, any of a case where no group A is replaced, a case where group A is replaced by group B and a case where group A is replaced by group C is allowed. If a plurality of A are present in a general formula corresponding to the comment, any of a case where no group A is replaced, a case where some of group A is replaced by group B or group C, and a case where all of group A are replaced by group B or group C is allowed. Here, group A replaced by any one may include a case where group A is replaced by group B, a case where group A is replaced by group C, and a case where group A replaced by group B and group A replaced by group C are mixed. Furthermore, when an option of substituent is increased, such as "may be replaced by B, C or D," the definitions as described above apply mutatis mutandis.

Formula 3

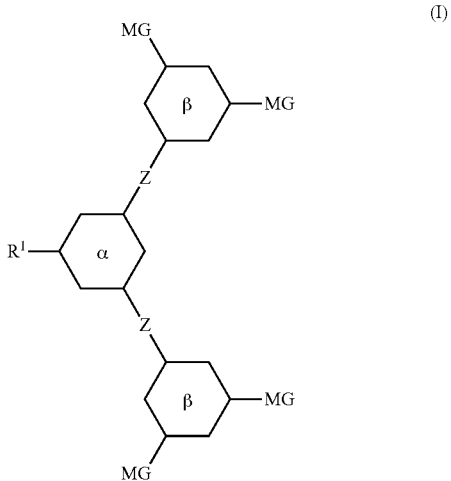

wherein, in formula (I), $R^1$ is fluorine, chlorine, or alkyl having 1 to 10 carbons, and in the alkyl, at least one of —$CH_2$— may be replaced by —O—, —S—, —CO— or —$SiH_2$—, and at least one of —$(CH_2)_2$— may be replaced by —CH=CH— or —C≡C—; α and β are independently cyclohexane-1,3,5-triyl or benzene-1,3,5-triyl, and in the rings, —$CH_2$— may be replaced by —O—, —S— or —$SiH_2$—, —CH— may be replaced by —N—, and —$(CH_2)_2$— may be replaced by —CH=CH—, and in the rings, at least one of hydrogen may be replaced by fluorine, chlorine, —$CF_3$, —$CHF_2$, —$CH_2F$, —$OCF_3$, —$OCHF_2$ or —$OCH_2F$; Z is a single bond or unbranched alkylene having 1 to 4 carbons, and in the alkylene, at least one of —$CH_2$— may be replaced by —O—, —CO—, —S— or —$SiH_2$—, at least one of —$(CH_2)_2$— may replaced by —CH=CH— or —C≡C—, and at least one of hydrogen may be replaced by fluorine; and MG is represented by formula (II):

Formula 4

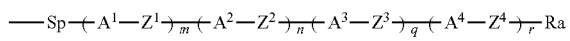
(II)

wherein, in formula (II), Sp is a single bond or unbranched alkylene having 1 to 10 carbons, and in the alkylene, at least one of —$CH_2$— may be replaced by —O—, —S—, —CO— or —$SiH_2$—, and at least one of —$(CH_2)_2$— may replaced by —CH═CH— or —C≡C—; Ra is independently fluorine, chlorine, or unbranched alkyl having 1 to 10 carbons, and in the alkyl, at least one of —$CH_2$— may be replaced by —O—, —S—, —CO— or —$SiH_2$—, and at least one of —$(CH_2)_2$— may be replaced by —CH═CH— or —C≡C—; $A^1$, $A^2$, $A^3$ and $A^4$ are independently 1,4-cyclohexylene, 1,4-phenylene, cyclohexene-1,4-diyl, decahydronaphthalene-2,6-diyl, 1,2,3,4-tetrahydronaphthalene-2,6-diyl or naphthalene-2,6-diyl, and in the rings, one of —$CH_2$— may be replaced by —O—, —S—, —CO— or —$SiH_2$—, and at least one of —$(CH_2)_2$— may be replaced by —CH═CH—, and in the rings, at least one of hydrogen may be replaced by fluorine, chlorine, —$CF_3$, —$CHF_2$, —$CH_2F$, —$OCF_3$, —$OCHF_2$ or —$OCH_2F$; $Z^1$, $Z^2$, $Z^4$ and $Z^5$ are independently a single bond or alkylene having 1 to 4 carbons, and in the alkylene, at least one of —$CH_2$— may be replaced by —O—, —S—, —CO— or —$SiH_2$—, at least one of —$(CH_2)_2$— may be replaced by —CH═CH— or —C≡C—, and at least one of hydrogen may be replaced by fluorine; and m, n, q and r are independently 0, 1 or 2, and a sum of m, n, q and r is 2, 3, 4 or 5.

The expression "in the alkylene, at least one of —$CH_2$— may be replaced by —O—, —S—, —CO— or —$SiH_2$—, and at least one of —$(CH_2)_2$— may be replaced by —CH═CH— or —C≡C—" as described above follows the definition of the comment. More specifically, the wording "at least one" means "at least one selected without distinction." Accordingly, in the alkyl, for example, $C_4H_9$—, examples of groups in which at least one of —$CH_2$— is replaced by —O—, or a group or groups in which at least one of —$(CH_2)_2$— is replaced by —CH═CH— include $HOC_3H_6$—, $C_3H_7O$—, $CH_3$—O—$(CH_2)_2$—, $CH_3$—O—$CH_2$—O—, $H_2C$═CH—$(CH_2)_2$—, $CH_3$—CH═CH—$CH_2$— and $CH_2$═CH—$CH_2$—O—. If stability of a compound is taken into consideration, $CH_3$—O—$CH_2$—O— in which oxygen and oxygen are not adjacent is preferred to $CH_3$—O—O—$CH_2$— in which oxygen and oxygen are adjacent.

Preferred $R^1$ is chlorine, fluorine, and alkyl, alkenyl, alkoxy, alkoxyalkyl, alkenyloxy, polyfluoroalkyl, polyfluoroalkoxy and polyfluoroalkenyl each having 1 to 8 carbons. In the groups, a straight chain is preferred to a branched chain. Further preferred $R^1$ is hydroxy-terminated alkyl or alkyl each having 1 to 10 carbons, alkenyl having 2 to 10 carbons, and alkoxy, alkoxyalkyl or alkenyloxy each having 1 to 9 carbons. Most preferred $R^1$ is hydroxy-terminated alkyl or alkyl each having 1 to 6 carbons, or alkenyl having 2 to 6 carbons.

A preferred configuration of —CH═CH— in alkenyl depends on a position of a double bond. In alkenyl such as 1-propenyl, 1-butenyl, 1-pentenyl, 1-hexenyl, 3-pentenyl or 3-hexenyl, a trans configuration is preferred. In alkenyl such as 2-butenyl, 2-pentenyl or 2-hexenyl, a cis configuration is preferred.

Specific examples of $R^1$ include hydroxymethyl, 2-hydroxyethyl, 3-hydroxypropyl, 4-hydroxybutyl, 5-hydroxypentyl, 6-hydroxyhexyl, 7-hydroxyheptyl, 8-hydroxyoctyl, methyl, ethyl, propyl, butyl, pentyl, hexyl, heptyl, octyl, methoxy, ethoxy, propoxy, butoxy, pentyloxy, hexyloxy, heptyloxy, methoxymethyl, methoxyethyl, methoxypropyl, ethoxymethyl, ethoxyethyl, ethoxypropyl, propoxymethyl, butoxymethyl, pentoxymethyl, vinyl, 1-propenyl, 2-propenyl, 1-butenyl, 2-butenyl, 3-butenyl, 1-pentenyl, 2-pentenyl, 3-pentenyl, 4-pentenyl, 2-propenyloxy, 2-butenyloxy, 2-pentenyloxy, —$CH_2F$, —$CHF_2$, —$CF_3$, —$(CH_2)_2F$, —$CF_2CH_2F$, —$CF_2CHF_2$, —$CH_2CF_3$, —$CF_2CF_3$, —$(CH_2)_3F$, —$(CF_2)_2CF_3$, —$CF_2CHFCF_3$, —$CHFCF_2CF_3$, —$OCF_3$, —$OCHF_2$, —$OCH_2F$, —$OCF_2CF_3$, —$OCF_2CHF_2$, —$OCF_2CH_2F$, —$OCF_2CF_2CF_3$, —$OCF_2CHFCF_3$, —$OCHFCF_2CF_3$, —CH═CHF, —CH═$CF_2$, —CF═CHF, —CH═$CHCH_2F$, —CH═$CHCF_3$ and —$(CH_2)_2CH$═$CF_2$.

Further preferred $R^1$ is fluorine, hydroxymethyl, 2-hydroxyethyl, 3-hydroxypropyl, 4-hydroxybutyl, 5-hydroxypentyl, 6-hydroxyhexyl, 7-hydroxyheptyl, 8-hydroxyoctyl, methyl, ethyl, propyl, butyl, pentyl, hexyl, heptyl, octyl, methoxy, ethoxy, propoxy, butoxy, pentyloxy, hexyloxy, heptyloxy, methoxymethyl, methoxyethyl, methoxypropyl, ethoxymethyl, ethoxyethyl, ethoxypropyl, propoxymethyl, butoxymethyl, pentoxymethyl, vinyl, 1-propenyl, 2-propenyl, 1-butenyl, 2-butenyl, 3-butenyl, 1-pentenyl, 2-pentenyl, 3-pentenyl, 4-pentenyl, 2-propenyloxy, 2-butenyloxy and 2-pentenyloxy. Most preferred $R^1$ is hydroxymethyl, 2-hydroxyethyl, 3-hydroxypropyl, 4-hydroxybutyl, 5-hydroxypentyl, 6-hydroxyhexyl, methyl, ethyl, propyl, butyl, pentyl, hexyl, heptyl, octyl, methoxy, ethoxy, propoxy, butoxy, pentyloxy, hexyloxy, heptyloxy, vinyl, 1-propenyl, 2-propenyl, 1-butenyl, 2-butenyl, 3-butenyl, 1-pentenyl, 2-pentenyl, 3-pentenyl and 4-pentenyl.

Then, α and β are independently cyclohexane-1,3,5-triyl or benzene-1,3,5-triyl, and in the rings, —$CH_2$— may be replaced by —O—, —S— or —$SiH_2$—, —CH— may be replaced by —N—, and —$(CH_2)_2$— may be replaced by —CH═CH—, and in the rings, at least one of hydrogen may be replaced by fluorine, chlorine, —$CF_3$, —$CHF_2$, —$CH_2F$, —$OCF_3$, —$OCHF_2$ or —$OCH_2F$.

Preferred α and β are cyclohexane-1,3,5-triyl or benzene-1,3,5-triyl, and 2,4,6-trifluorobenzene-1,3,5-triyl. Further preferred $A^{11}$, $A^{21}$ and $A^{22}$ are cyclohexane-1,3,5-triyl or benzene-1,3,5-triyl. Most preferred $A^{11}$, $A^{21}$ and $A^{22}$ are benzene-1,3,5-triyl.

Z is a single bond or unbranched alkylene having 1 to 4 carbons, and in the alkylene, at least one of —$CH_2$— may be replaced by —O—, —CO—, —S— or —$SiH_2$—, at least one of —$(CH_2)_2$— may be replaced by —CH═CH— or —C≡C—, and at least one of hydrogen may be replaced by fluorine.

Preferred Z is a single bond, —$(CH_2)_2$—, —COO—, —OCO—, —$CH_2O$—, —$OCH_2$—, —$CF_2O$—, —$OCF_2$—, —CH═CH—, —CF═CF—, —C≡C—, —$(CH_2)_2COO$—, —$OCO(CH_2)_2$—, —$(CH_2)_2CF_2O$—, —$OCF_2(CH_2)_2$—, —$(CH_2)_3O$—, —$O(CH_2)_3$— or —$(CH_2)_4$—. With regard to a configuration of a double bond of a bonding group such as —CH═CH—, trans is preferred to cis.

Further preferred Z is a single bond, —$(CH_2)_2$—, —$CH_2O$—, —$OCH_2$—, —$CF_2O$—, —$OCF_2$—, —C≡C— or —CH═CH—. Most preferred Z is a single bond, —$(CH_2)_2$—, —$CH_2O$—, —$OCH_2$—, —C≡C— or —CH═CH—.

In formula (II), Sp is a single bond or unbranched alkylene having 1 to 10 carbons, and in the alkylene, at least one of —$CH_2$— may be replaced by —O—, —S—, —CO— or —$SiH_2$—, and at least one of —$(CH_2)_2$— may be replaced by —CH═CH— or —C≡C—.

Preferred Sp is a single bond or alkylene having 1 to 10 carbons, and alkylene having 1 to 9 carbons and containing one oxygen atom or alkylene having 1 to 8 carbons and containing two oxygen atoms. In the alkylene, the number of carbons is preferably 2 to 10, further preferably, 2 to 8. When the number of carbons is 1 in oxyalkyleneoxy, acetal is formed, and chemical stability tends to be decreased.

Ra is independently fluorine, chlorine, or unbranched alkyl having 1 to 10 carbons, and in the alkyl, at least one of —$CH_2$— may be replaced by —O—, —S—, —CO— or —$SiH_2$—, and at least one of —$(CH_2)_2$— may be replaced by —CH=CH— or —C≡C—.

Preferred Ra is chlorine, fluorine, alkyl, alkenyl, alkoxy, alkoxyalkyl, alkenyloxy, polyfluoroalkyl, polyfluoroalkoxy and polyfluoroalkenyl each having 2 to 10 carbons. In the groups, a straight chain is preferred to a branched chain. Even branched-chain $R^1$ and $R^2$ are preferred in a case where $R^1$ and $R^2$ are optically active. Further preferred $R^1$ or $R^2$ is alkyl, alkenyl, alkoxy, alkoxyalkyl or alkenyloxy each having 2 to 10 carbons. Most preferred $R^1$ or $R^2$ is alkyl, alkoxy or alkenyl each having 2 to 10 carbons.

A preferred configuration of —CH=CH— in alkenyl depends on a position of a double bond. In alkenyl such as 1-propenyl, 1-butenyl, 1-pentenyl, 1-hexenyl, 3-pentenyl or 3-hexenyl, a trans configuration is preferred. In alkenyl such as 2-butenyl, 2-pentenyl or 2-hexenyl, a cis configuration is preferred.

Specific examples of Ra include methyl, ethyl, propyl, butyl, pentyl, hexyl, heptyl, octyl, methoxy, ethoxy, propoxy, butoxy, pentyloxy, hexyloxy, heptyloxy, methoxymethyl, methoxyethyl, methoxypropyl, ethoxymethyl, ethoxyethyl, ethoxypropyl, propoxymethyl, butoxymethyl, pentoxymethyl, vinyl, 1-propenyl, 2-propenyl, 1-butenyl, 2-butenyl, 3-butenyl, 1-pentenyl, 2-pentenyl, 3-pentenyl, 4-pentenyl, 2-propenyloxy, 2-butenyloxy, 2-pentenyloxy, —$CH_2F$, —$CHF_2$, —$CF_3$, —$(CH_2)_2F$, —$CF_2CH_2F$, —$CF_2CHF_2$, —$CH_2CF_3$, —$CF_2CF_3$, —$(CH_2)_3F$, —$(CF_2)_2CF_3$, —$CF_2CHFCF_3$, —$CHFCF_2CF_3$, —$OCF_3$, —$OCHF_2$, —$OCH_2F$, —$OCF_2CF_3$, —$OCF_2CHF_2$, —$OCF_2CH_2F$, —$OCF_2CF_2CF_3$, —$OCF_2CHFCF_3$, —$OCHFCF_2CF_3$, —CH=CHF, —CH=$CF_2$, —CF=CHF, —CH=$CHCH_2F$, —CH=$CHCF_3$ and —$(CH_2)_2CH$=$CF_2$.

Further preferred Ra is fluorine, ethyl, propyl, butyl, pentyl, hexyl, heptyl, octyl, methoxy, ethoxy, propoxy, butoxy, pentyloxy, hexyloxy, heptyloxy, methoxymethyl, methoxyethyl, methoxypropyl, ethoxymethyl, ethoxyethyl, ethoxypropyl, propoxymethyl, butoxymethyl, pentoxymethyl, vinyl, 1-propenyl, 2-propenyl, 1-butenyl, 2-butenyl, 3-butenyl, 1-pentenyl, 2-pentenyl, 3-pentenyl, 4-pentenyl, 2-propenyloxy, 2-butenyloxy and 2-pentenyloxy. Most preferred $R^1$ or $R^2$ is ethyl, propyl, butyl, pentyl, hexyl, heptyl, octyl, methoxy, ethoxy, propoxy, butoxy, pentyloxy, hexyloxy, heptyloxy, vinyl, 1-propenyl, 2-propenyl, 1-butenyl, 2-butenyl, 3-butenyl, 1-pentenyl, 2-pentenyl, 3-pentenyl and 4-pentenyl.

$A^1$, $A^2$, $A^3$ and $A^4$ are independently 1,4-cyclohexylene, 1,4-phenylene, cyclohexene-1,4-diyl, decahydronaphthalene-2,6-diyl, 1,2,3,4-tetrahydronaphthalene-2,6-diyl or naphthalene-2,6-diyl, and in the rings, one of —$CH_2$— may be replaced by —O—, —S—, —CO— or —$SiH_2$—, and at least one of —$(CH_2)_2$— may be replaced by —CH=CH—, and in the rings, at least one of hydrogen may be replaced by fluorine, chlorine, —$CF_3$, —$CHF_2$, —$CH_2F$, —$OCF_3$, —$OCHF_2$ or —$OCH_2F$:

Preferred $A^1$, $A^2$, $A^3$ or $A^4$ is 1,4-cyclohexylene, 1,4-phenylene, cyclohexene-1,4-diyl, 2-fluoro-1,4-phenylene, 2,3-difluoro-1,4-phenylene, 3,5-difluoro-1,4-phenylene decahydronaphthalene-2,6-diyl, 1,2,3,4-tetrahydronaphthalene-2,6-diyl or naphthalene-2,6-diyl. Further preferred $A^1$, $A^2$, $A^3$ or $A^4$ is 1,4-cyclohexylene, 1,4-phenylene, cyclohexene-1,4-diyl, 2-fluoro-1,4-phenylene, 3-fluoro-1,4-phenylene, 2,3-difluoro-1,4-phenylene or 3,5-difluoro-1,4-phenylene. Most preferred $A^1$, $A^2$, $A^3$ or $A^4$ is 1,4-cyclohexylene, 1,4-phenylene 2-fluoro-1,4-phenylene, 3-fluoro-1,4-phenylene, 2,3-difluoro-1,4-phenylene or 3,5-difluoro-1,4-phenylene.

$Z^1$, $Z^2$, $Z^3$ and $Z^4$ are independently a single bond or alkylene having 1 to 4 carbons, and in the alkylene, at least one of —$CH_2$— may be replaced by —O—, —S—, —CO— or —$SiH_2$—, at least one of —$(CH_2)_2$— may be replaced by —CH=CH— or —C≡C—, and at least one of hydrogen may be replaced by fluorine.

Preferred $Z^1$, $Z^2$, $Z^4$ or $Z^5$ is a single bond, —$(CH_2)_2$—, —COO—, —OCO—, —$CH_2O$—, —$OCH_2$—, —$CF_2O$—, —$OCF_2$—, —CH=CH—, —CF=CF—, —C≡C—, —$(CH_2)_2COO$—, —$OCO(CH_2)_2$—, —$(CH_2)_2CF_2O$—, —$OCF_2(CH_2)_2$—, —$(CH_2)_3O$—, —$O(CH_2)_3$— or —$(CH_2)_4$—. With regard to a configuration of a double bond of a bonding group such as —CH=CH—, trans is preferred to cis.

Further preferred $Z^1$, $Z^2$, $Z^4$ or $Z^5$ is a single bond, —$(CH_2)_2$—, —$CH_2O$—, —$OCH_2$—, —$CF_2O$—, —$OCF_2$— or —CH=CH—. Most preferred $Z^1$, $Z^2$, $Z^4$ or $Z^5$ is a single bond, —$CH_2O$—, —$OCH_2$—, —$CF_2O$—, —$OCF_2$— or —CH=CH—.

Item 2. The compound according to item 1, wherein, in formula (I), $R^1$ is fluorine, alkyl having 1 to 10 carbons, alkenyl having 2 to 10 carbons, alkoxy having 1 to 9 carbons, alkoxyalkyl having 2 to 9 carbons, alkenyloxy having 3 to 9 carbons, polyfluoroalkyl having 1 to 10 carbons, polyfluoroalkoxy having 1 to 9 carbons, polyfluoroalkenyl having 2 to 10 carbons, or hydroxy-terminated alkyl having 1 to 10 carbons; α and β are independently cyclohexane-1,3,5-triyl, 1,3,5-trioxane-2,4,6-triyl, benzene-1,3,5-triyl or 1,3,5-triazine-2,4,6-triyl; Z is a single bond, —$(CH_2)_2$—, —$CH_2O$—, —$OCH_2$—, —$CF_2O$—, —$OCF_2$—, —CH=CH—, —CF=CF—, —C≡C—, —COO—, —OCO—, —$CH_2SiH_2$—, —$SiH_2CH_2$—, —$(CH_2)_2COO$—, —OCO$(CH_2)_2$—, —$(CH_2)_2CF_2O$—, —$OCF_2(CH_2)_2$—, —$(CH_2)_3O$—, —$O(CH_2)_3$— or —$(CH_2)_4$—; and in formula (II), Sp is a single bond, unbranched alkylene having 1 to 10 carbons, alkenylene having 1 to 10 carbons, alkynylene having 1 to 10 carbons, oxyalkylene having 2 to 10 carbons, alkyleneoxy having 2 to 10 carbons or oxyalkyleneoxy having 3 to 10 carbons; Ra is independently fluorine, alkyl having 1 to 10 carbons, alkenyl having 2 to 10 carbons, alkoxy having 1 to 9 carbons, alkoxyalkyl having 2 to 9 carbons, alkenyloxy having 3 to 9 carbons, polyfluoroalkyl having 1 to 10 carbons, polyfluoroalkoxy having 1 to 9 carbons or polyfluoroalkenyl having 2 to 10 carbons; $A^1$, $A^2$, $A^3$ and $A^4$ are independently 1,4-cyclohexylene, 1,4-phenylene, cyclohexene-1,4-diyl, decahydronaphthalene-2,6-diyl, 1,2,3,4-tetrahydronaphthalene-2,6-diyl or naphthalene-2,6-diyl, and at least one of hydrogen may be replaced by fluorine, chlorine, —$CF_3$ or —$CHF_2$; $Z^1$, $Z^2$ and $Z^4$ are independently a single bond, —$(CH_2)_2$—, —COO—, —OCO—, —$CH_2O$—, —$OCH_2$—, —$CF_2O$—, —$OCF_2$—, —CH=CH—, —CF=CF—, —C≡C—, —$CH_2CO$—, —$COCH_2$—, —$CH_2SiH_2$—, —$SiH_2CH_2$—, —$(CH_2)_2COO$—, —OCO$(CH_2)_2$—, —$(CH_2)_2CF_2O$—, —$OCF_2(CH_2)_2$—, —$(CH_2)_3O$—, —$O(CH_2)_3$— or —$(CH_2)_4$—; and m, n, q and r are independently 0 or 1, and a sum of m, n, q and r is 2, 3 or 4.

Item 3. The compound according to item 1, wherein, in formula (I), $R^1$ is fluorine, alkyl having 1 to 6 carbons, alkenyl having 2 to 6 carbons, alkoxy having 2 to 6 carbons, alkoxyalkyl having 2 to 6 carbons, alkenyloxy having 3 to 6 carbons, polyfluoroalkyl having 1 to 6 carbons, polyfluoroalkoxy having 1 to 6 carbons, polyfluoroalkenyl having 2 to 6 carbons or hydroxy-terminated alkyl having 1 to 6 carbons; α and β are benzene-1,3,5-triyl; Z is a single bond, —(CH$_2$)$_2$—, —CH$_2$O—, —OCH$_2$—, —CF$_2$O—, —OCF$_2$—, —CH=CH—, —CF=CF—, —C≡C—, —COO— or —OCO—; and in formula (II), Sp is a single bond, unbranched alkylene having 1 to 10 carbons, alkenylene having 1 to 10 carbons, alkynylene having 1 to 10 carbons, oxyalkylene having 2 to 10 carbons, alkyleneoxy having 2 to 10 carbons or oxyalkyleneoxy having 3 to 10 carbons; Ra is independently fluorine, alkyl having 1 to 6 carbons, alkenyl having 2 to 6 carbons, alkoxy having 1 to 6 carbons, polyfluoroalkyl having 1 to 6 carbons, polyfluoroalkoxy having 2 to 6 carbons or polyfluoroalkenyl having 2 to 6 carbons; $A^1$, $A^2$, $A^3$ and $A^4$ are independently 1,4-cyclohexylene, 1,4-phenylene, cyclohexene-1,4-diyl, 2-fluoro-1,4-phenylene, 2,3-difluoro-1,4-phenylene, 3,5-difluoro-1,4-phenylene, 2,5-difluoro-1,4-phenylene, 2-fluoro-3-trifluoromethyl-1,4-phenylene or 2-fluoro-3-difluoromethyl-1,4-phenylene; $Z^1$, $Z^2$ and $Z^4$ are independently a single bond, —(CH$_2$)$_2$—, —CH$_2$O—, —OCH$_2$—, —CF$_2$O—, —OCF$_2$—, —CH=CH—, —CF=CF—, —C≡C—, —(CH$_2$)$_2$CF$_2$O—, —OCF$_2$(CH$_2$)$_2$—, —(CH$_2$)$_3$O—, —O(CH$_2$)$_3$— or —(CH$_2$)$_4$—; and m, n, q and r are independently 0 or 1, and a sum of m, n, q and r is 2, 3 or 4.

Item 4. The compound according to item 2, represented by formula (I-1):

Formula 5

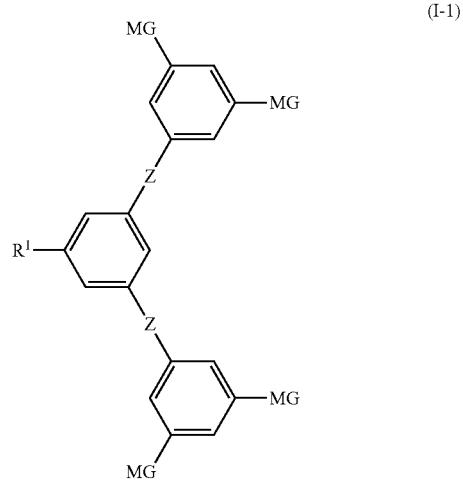

(I-1)

wherein, in formula (I-1), $R^1$ is fluorine, alkyl having 1 to 6 carbons, alkenyl having 2 to 6 carbons, alkoxy having 2 to 6 carbons, alkoxyalkyl having 2 to 6 carbons, alkenyloxy having 3 to 6 carbons, polyfluoroalkyl having 1 to 6 carbons, polyfluoroalkoxy having 1 to 6 carbons, polyfluoroalkenyl having 2 to 6 carbons or hydroxy-terminated alkyl having 1 to 6 carbons; Z is independently a single bond, —(CH$_2$)$_2$—, —CH$_2$O—, —OCH$_2$—, —CF$_2$O—, —OCF$_2$—, —CH=CH—, —CF=CF— or —C≡C—; and MG is represented by formula (II-1):

Formula 6

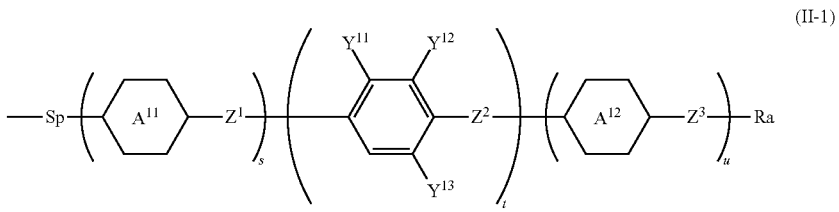

(II-1)

wherein, in formula (II-1), Sp is a single bond, unbranched alkylene having 1 to 10 carbons, alkenylene having 2 to 10 carbons, alkynylene having 2 to 10 carbons, oxyalkylene having 1 to 9 carbons, alkyleneoxy having 1 to 9 carbons or oxyalkyleneoxy having 1 to 8 carbons; Ra is independently fluorine, alkyl having 1 to 6 carbons, alkenyl having 2 to 6 carbons, alkoxy having 1 to 5 carbons, polyfluoroalkyl having 1 to 6 carbons, polyfluoroalkoxy having 1 to 5 carbons or polyfluoroalkenyl having 2 to 6 carbons; $A^{11}$ and $A^{12}$ are 1,4-cyclohexylene or 1,4-phenylene; $Y^{11}$, $Y^{12}$ and $Y^{13}$ are independently hydrogen, fluorine, —CF$_3$ or —CF$_2$H; $Z^1$, $Z^2$ and $Z^4$ are independently a single bond, —(CH$_2$)$_2$—, —CH$_2$O—, —OCH$_2$—, —CF$_2$O—, —OCF$_2$—, —CH=CH—, —CF=CF— or —C≡C—; and s, t and u are independently 0, 1 or 2, and a sum of s, t and u is 2, 3 or 4, but t is 1 without fail.

Item 5. The compound according to item 4, wherein, in formula (I-1), $R^1$ is alkyl having 1 to 3 carbons, alkenyl having 2 to 3 carbons, alkoxy having 2 to 3 carbons or hydroxy-terminated alkyl having 1 to 3 carbons; and Z is a single bond, —(CH$_2$)$_2$—, —CH$_2$O—, —OCH$_2$—, —CH=CH— or —C≡C—.

Item 6. The compound according to item 5, wherein, in formula (II-1), Sp is a single bond, unbranched alkylene having 1 to 8 carbons, alkenylene having 2 to 8 carbons, alkynylene having 2 to 8 carbons, oxyalkylene having 1 to 7 carbons, alkyleneoxy having 1 to 7 carbons or oxyalkyleneoxy having 1 to 6 carbons; Ra is independently fluorine, polyfluoroalkyl having 1 to 6 carbons, polyfluoroalkoxy having 2 to 6 carbons or polyfluoroalkenyl having 2 to 6 carbons; $A^{11}$ and $A^{12}$ are 1,4-cyclohexylene or 1,4-phenylene; $Y^{11}$ is hydrogen, $Y^{12}$ and $Y^{13}$ are independently hydrogen or fluorine, but at least one is fluorine; $Z^1$, $Z^2$ and $Z^3$ are independently a single bond, —(CH$_2$)$_2$—, —CF$_2$O—, —CH=CH—, —CF=CF— or —C≡C—; and a sum of s, t and u is 2 or 3.

Item 7. The compound according to item 5, wherein, in formula (II-1), Sp is a single bond, unbranched alkylene having 1 to 8 carbons, alkenylene having 2 to 8 carbons, alkynylene having 2 to 8 carbons, oxyalkylene having 1 to 7 carbons, alkyleneoxy having 1 to 7 carbons or oxyalkyleneoxy having 1 to 6 carbons; Ra is independently alkyl having 1 to 6 carbons, alkenyl having 2 to 6 carbons or alkoxy having 1 to 5 carbons; $A^{11}$ and $A^{12}$ are 1,4-cyclohexylene or 1,4- phenylene; $Y^{11}$ and $Y^{12}$ are fluorine and $Y^{13}$ is hydrogen; $Z^1$, $Z^2$ and $Z^3$ are independently a single bond, —(CH$_2$)$_2$—, —CH$_2$O—, —OCH$_2$—, —CH═CH—, —CF═CF— or —C≡C—; and a sum of s, t and u is 2 or 3.

Item 8. The compound according to item 5, wherein, in formula (I-1), Sp is a single bond, unbranched alkylene having 1 to 8 carbons, alkenylene having 2 to 8 carbons, alkynylene having 2 to 8 carbons, oxyalkylene having 1 to 7 carbons, alkyleneoxy having 1 to 7 carbons or oxyalkyleneoxy having 1 to 6 carbons; Ra is independently alkyl having 1 to 6 carbons, alkenyl having 2 to 6 carbons or alkoxy having 1 to 5 carbons; $A^{11}$ and $A^{12}$ are 1,4-cyclohexylene or 1,4-phenylene; $Y^{11}$ and $Y^{13}$ are independently hydrogen or fluorine, and $Y^{12}$ is hydrogen; $Z^1$, $Z^2$ and $Z^4$ are independently a single bond, —(CH$_2$)$_2$—, —CH═CH—, —CF═CF— or —C≡C—; and a sum of s, t and u is 2 or 3.

Item 9. The compound according to item 5, wherein, in formula (I-1), MG is represented by formula (II-1-1-1) to formula (II-1-1-16):

Formula 7

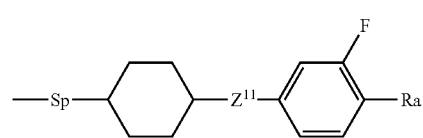
(II-1-1-1)

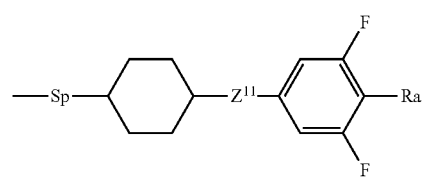
(II-1-1-2)

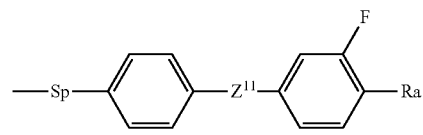
(II-1-1-3)

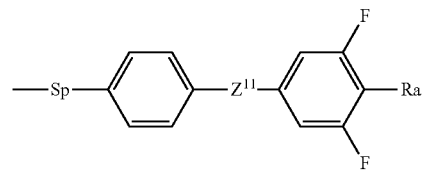
(II-1-1-4)

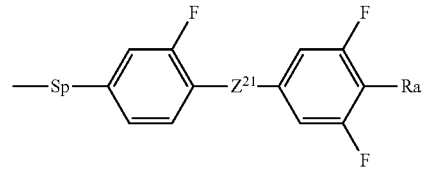
(II-1-1-5)

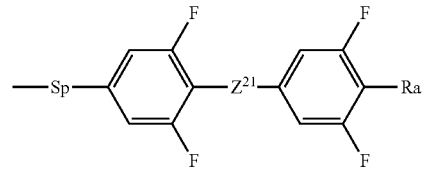
(II-1-1-6)

-continued

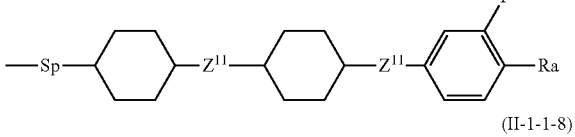
(II-1-1-7)

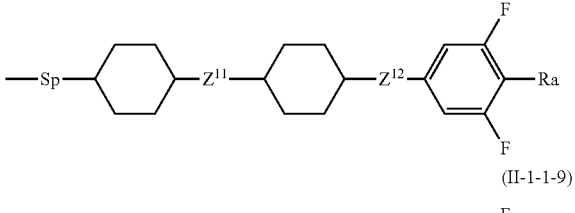
(II-1-1-8)

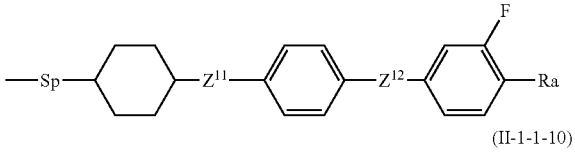
(II-1-1-9)

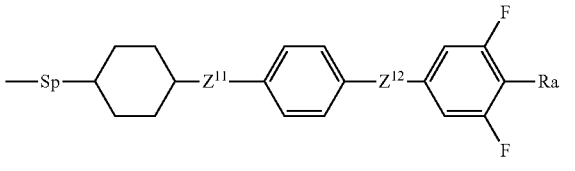
(II-1-1-10)

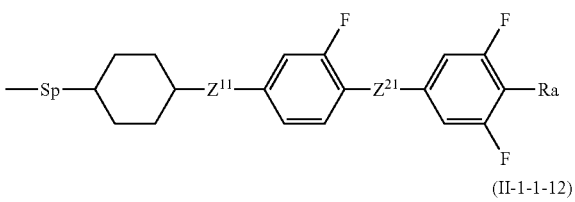
(II-1-1-11)

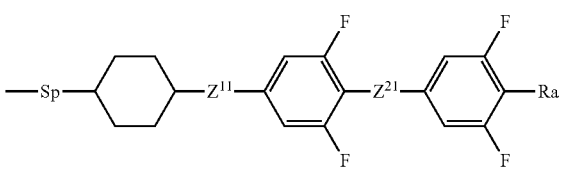
(II-1-1-12)

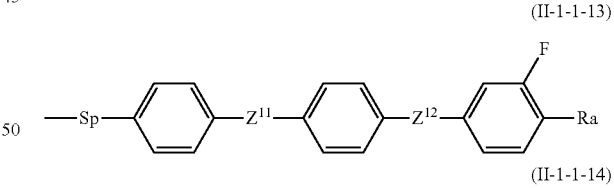
(II-1-1-13)

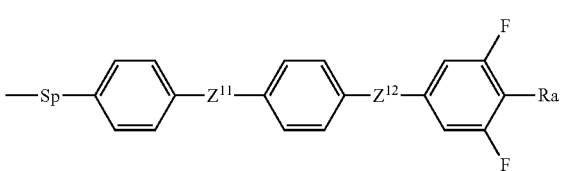
(II-1-1-14)

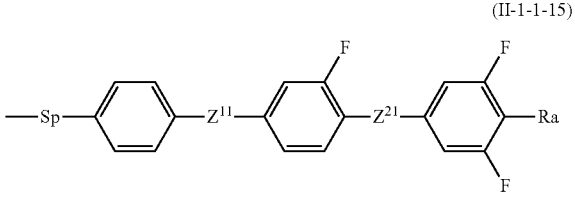
(II-1-1-15)

-continued (II-1-1-16)
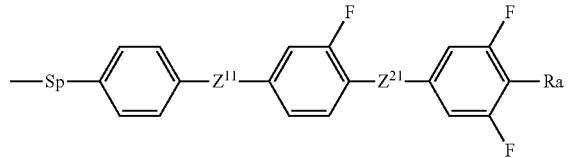

wherein, in formula (II-1-1-1) to formula (II-1-1-16), Sp is a single bond, unbranched alkylene having 1 to 8 carbons, alkenylene having 2 to 8 carbons, alkynylene having 2 to 8 carbons, oxyalkylene having 1 to 7 carbons, alkyleneoxy having 1 to 7 carbons or oxyalkyleneoxy having 1 to 6 carbons; Ra is independently fluorine, —CF$_3$, —CF$_2$H or —OCF$_3$; and Z$^{11}$, Z$^{12}$ and Z$^{21}$ are independently a single bond, —(CH$_2$)$_2$—, —CF$_2$O—, —CH=CH—, —CF=CF— or —C≡C—.

Item 10. The compound according to item 5, wherein, in formula (I-1), MG is represented by formula (II-1-2-1) to formula (II-1-2-14):

Formula 8

(II-1-2-1)

(II-1-2-2)
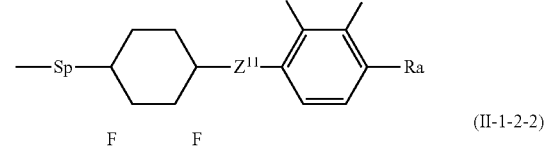

(II-1-2-3)
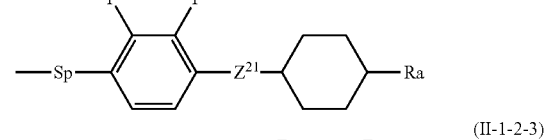

(II-1-2-4)
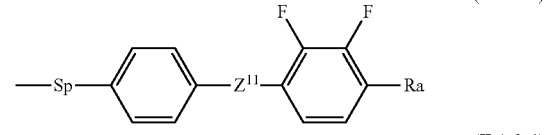

(II-1-2-5)
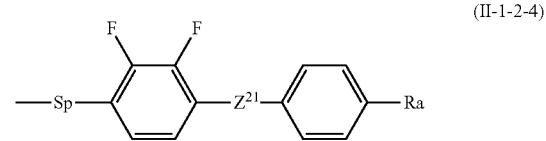

(II-1-2-6)
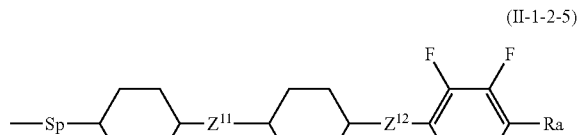

(II-1-2-7)
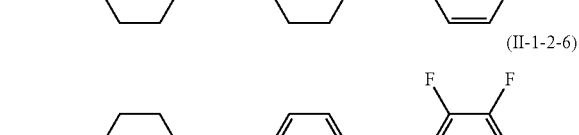

(II-1-2-8)
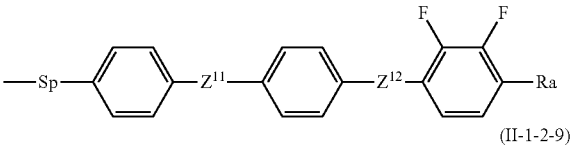

(II-1-2-9)
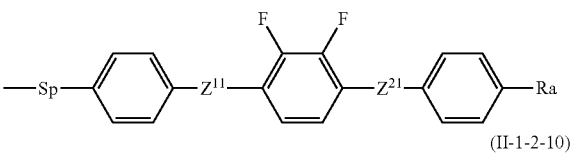

(II-1-2-10)
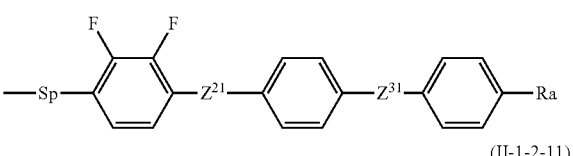

(II-1-2-11)
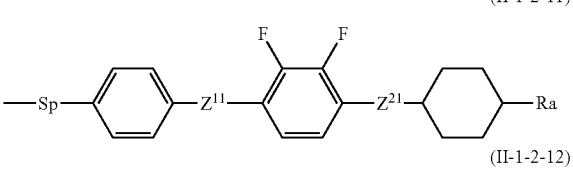

(II-1-2-12)

(II-1-2-13)
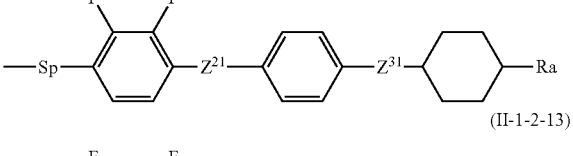

(II-1-2-14)
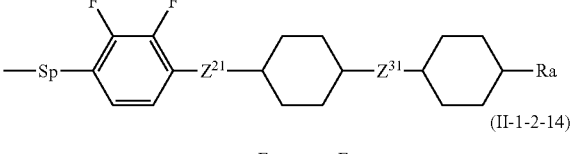

wherein, in formula (II-1-2-1) to formula (II-1-2-14), Sp is a single bond, unbranched alkylene having 1 to 8 carbons, alkenylene having 2 to 8 carbons, alkynylene having 2 to 8 carbons, oxyalkylene having 2 to 6 carbons, alkyleneoxy having 2 to 6 carbons or oxyalkyleneoxy having 3 to 6 carbons; Ra is independently alkyl having 1 to 6 carbons, alkenyl having 2 to 6 carbons or alkoxy having 1 to 6 carbons; and Z$^{11}$, Z$^{12}$, Z$^{21}$ and Z$^{31}$ are independently a single bond, —(CH$_2$)$_2$—, —CH$_2$O—, —OCH$_2$—, —CH=CH—, —CF=CF— or —C≡C—.

Item 11. The compound according to item 5, wherein, in formula (I-1), MG is represented by formula (II-1-3-1) to formula (II-1-3-17):

Formula 9

(II-1-3-1)
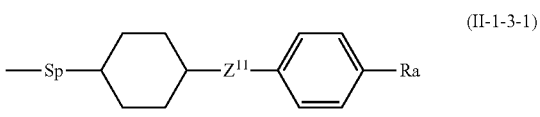

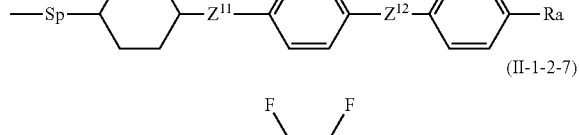
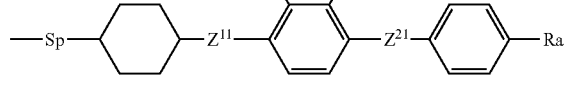
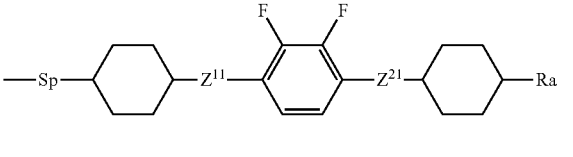

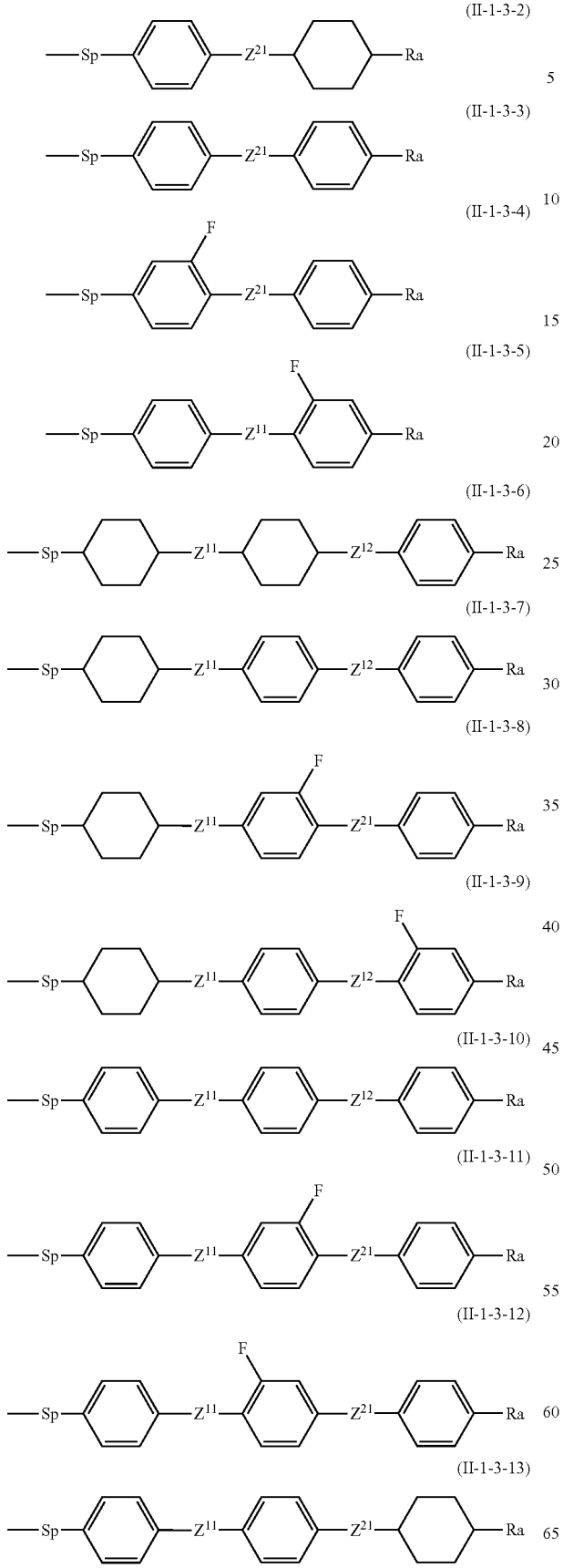

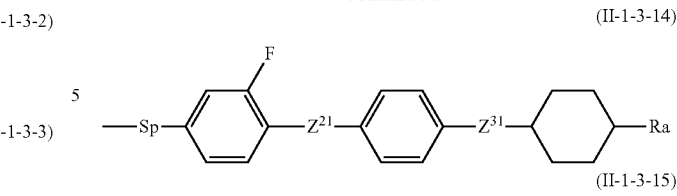

Item 12. A liquid crystal composition containing at least one compound according to any one of items 1 to 11. At least one compound according to any one of items 1 to 11 is referred to as "compound (1)" herein. More specifically, item 12 refers to a liquid crystal composition containing at least one compound (1) according to any one of items 1 to 11.

Item 13. The liquid crystal composition according to item 12, containing at least one of compound (1) and at least one compound represented by formula (2), (3) or (4):

Formula 10

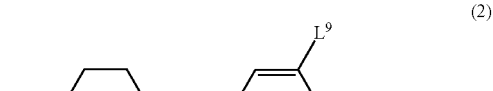 (2)

 (3)

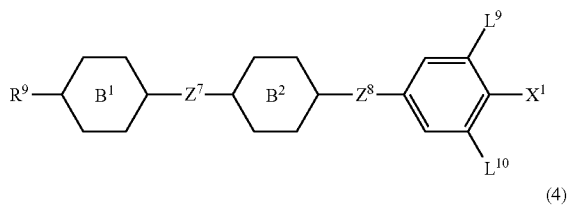 (4)

wherein, in formulas (2) to (4), $R^9$ is independently alkyl having 1 to 10 carbons or alkenyl having 2 to 10 carbons, and in the alkyl and the alkenyl, at least one of hydrogen may be replaced by fluorine, and at least one of —$CH_2$— may be replaced by —O—; $X^1$ is fluorine, chlorine, —$OCF_3$, —$OCHF_2$, —$CF_3$, —$CHF_2$, —$CH_2F$, —$OCF_2CHF_2$ or —$OCF_2CHFCF_3$; ring $B^1$, ring $B^2$ and ring $B^3$ are independently 1,4-cyclohexylene, 1,3-dioxane-2,5-diyl, pyrimidine-2,5-diyl, 1-tetrahydropyran-2,5-diyl, 1,4-phenylene, 2-fluoro-1,4-phenylene, 3-fluoro-1,4-phenylene or 3,5-difluoro-1,4-phenylene; $Z^7$ and $Z^8$ are independently —$(CH_2)_2$—, —$(CH_2)_4$—, —COO—, —$CF_2O$—, —$OCF_2$—, —CH=CH—, —C≡C—, —$CH_2O$— or a single bond; and $L^9$ and $L^{10}$ are independently hydrogen or fluorine.

Item 14. The liquid crystal composition according to item 12, containing at least one of compound (1) and at least one compound represented by formula (5):

Formula 9

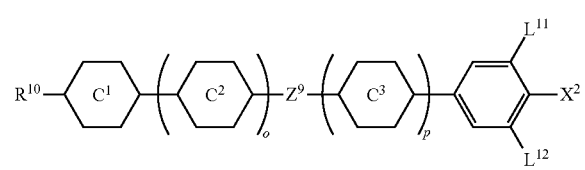

(5)

wherein, in formula (5), $R^{10}$ is alkyl having 1 to 10 carbons or alkenyl having 2 to 10 carbons, and in the alkyl and the alkenyl, at least one of hydrogen may be replaced by fluorine, and at least one of —$CH_2$— may be replaced by —O—; $X^2$ is —C≡N or —C≡C—C≡N;
ring $C^1$, ring $C^2$ and ring $C^3$ are independently 1,4-cyclohexylene, 1,4-phenylene in which at least one of hydrogen may be replaced by fluorine, 1,3-dioxane-2,5-diyl, 1-tetrahydropyran-2,5-diyl or pyrimidine-2,5-diyl; $Z^9$ is —$(CH_2)_2$—, —COO—, —$CF_2O$—, —$OCF_2$—, —C≡C—, —$CH_2O$— or a single bond; $L^{11}$ and $L^{12}$ are independently hydrogen or fluorine; and o is 0, 1 or 2, p is 0 or 1, and a sum of o and p is 0, 1, 2 or 3.

Item 15. The liquid crystal composition according to item 12, containing at least one of compound (1) and at least one compound represented by any one of formulas (6) to (11):

Formula 12

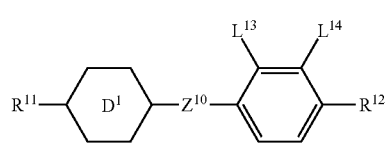

(6)

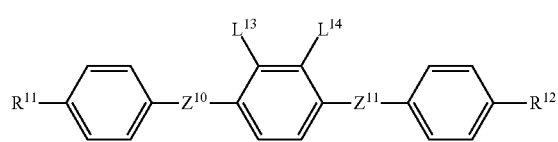

(8)

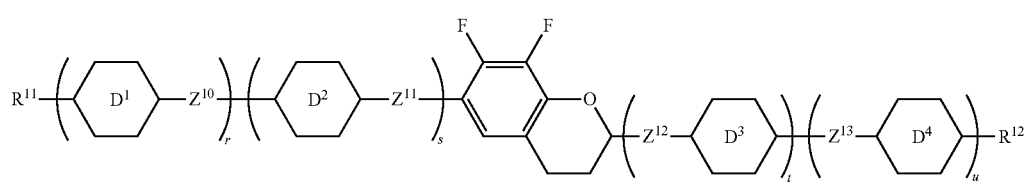

(10)

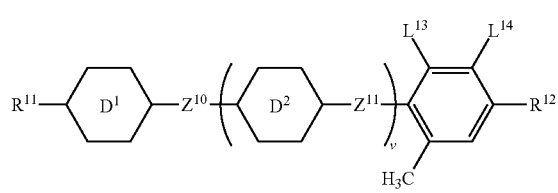

wherein, in formulas (6) to (11), $R^{11}$ and $R^{12}$ are independently alkyl having 1 to 10 carbons or alkenyl having 2 to 10 carbons, and in the alkyl and the alkenyl, at least one of hydrogen may be replaced by fluorine, and at least one of —$CH_2$— may be replaced by —O—; ring $D^1$, ring $D^2$, ring $D^3$ and ring $D^4$ are independently 1,4-cyclohexylene, 1,4-cyclohexenylene, 1,4-phenylene in which at least one of hydrogen may be replaced by fluorine, 6-tetrahydropyran-2,5-diyl or decahydro-2,6-naphthalene; $Z^{10}$, $Z^{11}$, $Z^{12}$ and $Z^{13}$ are independently —$(CH_2)_2$—, —COO—, —$CH_2O$—, —$OCF_2$—, —$OCF_2(CH_2)_2$— or a single bond; $L^{13}$ and $L^{14}$ are independently fluorine or chlorine; and q, r, s, t, u and v are independently 0 or 1, and a sum of r, s, t and u is 1 or 2.

Item 16. The liquid crystal composition according to item 12, containing at least one of compound (1) and at least one of compounds represented by formula (12), (13) or (14):

Formula 13

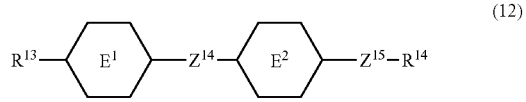

(12)

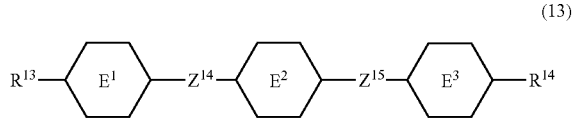

(13)

-continued

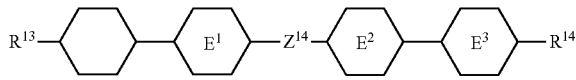
(14)

wherein, in formulas (12) to (14), $R^{13}$ and $R^{14}$ are independently alkyl having 1 to 10 carbons or alkenyl having 2 to 10 carbons, and in the alkyl and the alkenyl, at least one of —$CH_2$— may be replaced by —O—;

ring $E^1$, ring $E^2$ and ring $E^3$ are independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and $Z^{14}$ and $Z^{15}$ are independently —C≡C—, —COO—, —($CH_2$)$_2$—, —CH=CH— or a single bond.

Item 17. The liquid crystal composition according to item 13, further containing at least one compound represented by formula (5) according to item 15.

Item 18. The liquid crystal composition according to item 13, further containing at least one compound represented by formula (12), (13) or (14) according to item 16.

Item 19. The liquid crystal composition according to item 14, further containing at least one compound represented by formula (12), (13) or (14) according to item 16.

Item 20. The liquid crystal composition according to item 15, further containing at least one compound represented by formula (12), (13) or (14) according to item 16.

Item 21. The liquid crystal composition according to any one of items 12 to 20, further containing at least one optically active compound and/or at least one polymerizable compound.

Item 22. The liquid crystal composition according to any one of items 12 to 21, further containing at least one antioxidant and/or at least one ultraviolet light absorber.

Item 23. A liquid crystal display device including the liquid crystal composition according to any one of items 12 to 22.

Advantageous Effects of Invention

A compound of the invention has stability to heat, light and so forth and a suitable optical anisotropy, and threshold voltage of the compound per se is low. Then, the compound has an excellent compatibility with fluorine-based compounds or the like used for a liquid crystal composition for display. Consequently, the compound of the invention can be used as a liquid crystal material suitable for various display operations. A liquid crystal composition containing the compound according to the invention has a low threshold voltage, stability to heat, light and so forth, and a nematic phase maintained in a wide temperature range to exhibit a suitable optical anisotropy. A liquid crystal display device using such a liquid crystal composition according to the invention can be operated in a wide temperature range, has a short response time, a large contrast ratio and a low driving voltage, and is suitable for a small-sized portable terminal that has recently attracted attention.

DESCRIPTION OF EMBODIMENTS

Usage of terms herein is as described below. A liquid crystal compound is a generic term for a compound having a liquid crystal phase such as a nematic phase or a smectic phase, and a compound having no liquid crystal phase but being useful as a component of a liquid crystal composition. "Liquid crystal compound," "liquid crystal composition" and "liquid crystal display device" may be occasionally abbreviated as "compound," "composition" and "device," respectively. The liquid crystal display device is a generic term for a liquid crystal display panel and a liquid crystal display module. A maximum temperature of the nematic phase is a phase transition temperature between the nematic phase and an isotropic phase, and may be occasionally abbreviated simply as the maximum temperature. A minimum temperature of the nematic phase may be occasionally abbreviated simply as "minimum temperature." "Compound represented by formula (I)" may be occasionally abbreviated as "compound (I)." The abbreviation may occasionally apply to a compound represented by formula (II) or the like. In formula (I), formula (II), and formula (2) to formula (14), a symbol $A^1$, $A^2$ or the like corresponds to ring $A^1$, ring $A^2$, ring E, ring M or the like, respectively. A ratio (percentage) of a component or liquid crystal compound is expressed in terms of "weight percent (% by weight)" based on the total weight of the liquid crystal compound. Hereinafter, the invention will be further explained.

First, compound (I) of the invention will be further explained. Compound (I) is a compound having a dendrimeric structure. The compound is physically and chemically stable under conditions in which a device is ordinarily used, and has a good compatibility with other liquid crystal compounds. A composition containing the compound is stable under the conditions in which the device is ordinarily used. Even when the composition is stored at a low temperature, the compound does not precipitate as a crystal (or a smectic phase). The compound has general physical properties necessary for the compound, a suitable optical anisotropy, and a suitable dielectric anisotropy.

When a terminal group, a ring and a bonding group of compound (I) are suitably selected, physical properties such as optical anisotropy can be arbitrarily adjusted. An effect of kinds of terminal groups $R^1$, α, β, $Z^{11}$, Sp and Ra, rings $A^1$, $A^2$, $A^3$ and $A^4$, and bonding group $Z^1$, $Z^2$, $Z^3$ and $Z^4$ on the physical properties of compound (I) will be explained below.

When $R^1$ is a hydroxyl-terminated alkyl group, a liquid crystal phase temperature range is wide and $k_{22}$ is smaller. When $R^1$ is alkenyl, a preferred configuration depends on a position of a double bond.

When rings α and β are benzene-1,3,5-triyl, the optical anisotropy is large, and when the rings are triazine-1,3,5-triyl, the optical anisotropy is larger. When the rings are cyclohexane-1,3,5-triyl, the optical anisotropy is small.

When bonding group Z is a single bond, —($CH_2$)$_2$—, —$CH_2O$—, —$OCH_2$—, —$CF_2O$—, —$OCF_2$—, —CH=CH—, —CF=CF— or —($CH_2$)$_4$—, the viscosity is small. When the bonding group is a single bond, —($CH_2$)$_2$—, —CF=CF— or —CH=CH—, the viscosity is smaller. When the bonding group is —CH=CH—, —C≡C—, the temperature range of the liquid crystal phase is wide and the optical anisotropy is large.

When Sp is oxyalkylene, the temperature range of the liquid crystal phase is wide, and when Sp is oxyalkyleneoxy, the temperature range of the liquid crystal phase is wider. Then, when Sp is alkylene, the viscosity is small.

When Ra is alkenyl, a preferred configuration depends on a position of a double bond. An alkenyl compound having a preferred configuration has a high maximum temperature or a wide temperature range of the liquid crystal phase. A detailed description is found in Mol. Cryst. Liq. Cryst., 1985, 131, 109 and Mol. Cryst. Liq. Cryst., 1985, 131, 327.

When rings $A^1$ to $A^4$ are 1,4-phenylene or 2-fluoro-1,4-phenylene, the optical anisotropy is large. When rings $A^1$ to $A^4$ are 1,4-cyclohexylene, the optical anisotropy is small.

When at least two rings are 1,4-cyclohexylene, the maximum temperature is high, the optical anisotropy is small, and the viscosity is small. When at least one ring is 1,4-phenylene, the optical anisotropy is relatively large and an orientational order parameter is large.

When rings $A^1$ to $A^4$ are 1,4-phenylene in which at least one of hydrogen is replaced by halogen, or 1,3-dioxane-2,5-diyl, the dielectric anisotropy is positively large. When rings $A^1$ to $A^4$ are 2,3-difluoro-1,4-phenylene, the dielectric anisotropy is negatively large. When rings $A^1$ to $A^4$ are 2-(trifluoromethyl)-3-fluoro-1,4-phenylene, 2-(difluoromethyl)-3-fluoro-1,4-phenylene or 2-fluoro-3-(difluoromethyl)-1,4-phenylene, the dielectric anisotropy is negatively larger. When rings $A^1$ to $A^4$ are 1,4-phenylene in which at least one of hydrogen may be replaced by halogen, the optical anisotropy is large. When rings $A^1$ to $A^4$ are 1,4-cyclohexylene, 1,4-cyclohexenylene or 1,3-dioxane-2,5-diyl, the optical anisotropy is small.

When rings $A^1$ to $A^4$ are cyclohexene-1,4-diyl, a melting point is low. Moreover, when rings $A^1$ to $A^4$ simultaneously have cyclohexene-1,4-diyl and 1,4-phenylene simultaneously, the optical anisotropy is large.

When bonding group $Z^1$, $Z^2$, $Z^4$ or $Z^5$ is a single bond, —(CH$_2$)$_2$—, —CH$_2$O—, —OCH$_2$—, —CF$_2$O—, —OCF$_2$—, —CH=CH—, —CF=CF— or —(CH$_2$)$_4$—, the viscosity is small. When the bonding group is a single bond, —(CH$_2$)$_2$—, —CF=CF— or —CH=CH—, the viscosity is smaller. When the bonding group is —CH=CH—, the temperature range of the liquid crystal phase is wide. When the bonding group is —C≡C—, the optical anisotropy is large.

When MG represented by formula (II) in compound (I) is bicyclic, the compatibility with other liquid crystal compounds is high, and the viscosity is low. When MG has three rings or four rings, the temperature range of the liquid crystal phase is wide, and the maximum temperature is high. As described above, when kinds of terminal groups, rings and bonding groups, and the number of rings are suitably selected, a compound having objective physical properties can be obtained.

Compound (I) is prepared by suitably combining techniques in synthetic organic chemistry. Methods for introducing objective terminal groups, rings and bonding groups into a starting material are described in books such as Organic Syntheses (John Wiley & Sons, Inc.), Organic Reactions (John Wiley & Sons, Inc.), Comprehensive Organic Synthesis (Pergamon Press) and New Experimental Chemistry Course (Shin Jikken Kagaku Koza, in Japanese) (Maruzen Co., Ltd.).

With regard to one example of a method for forming bonding group $Z^1$, $Z^2$, $Z^4$ or $Z^5$, a scheme is first shown, and then the scheme will be explained in sections (i) to (xi). MSG$^1$ or MSG$^2$ is a monovalent organic group having at least one ring. Organic groups represented by a plurality of MSG$^1$ (or MSG$^2$) may be identical or different. Compounds (1A) to (1K) correspond to compound (I).

Formula 14

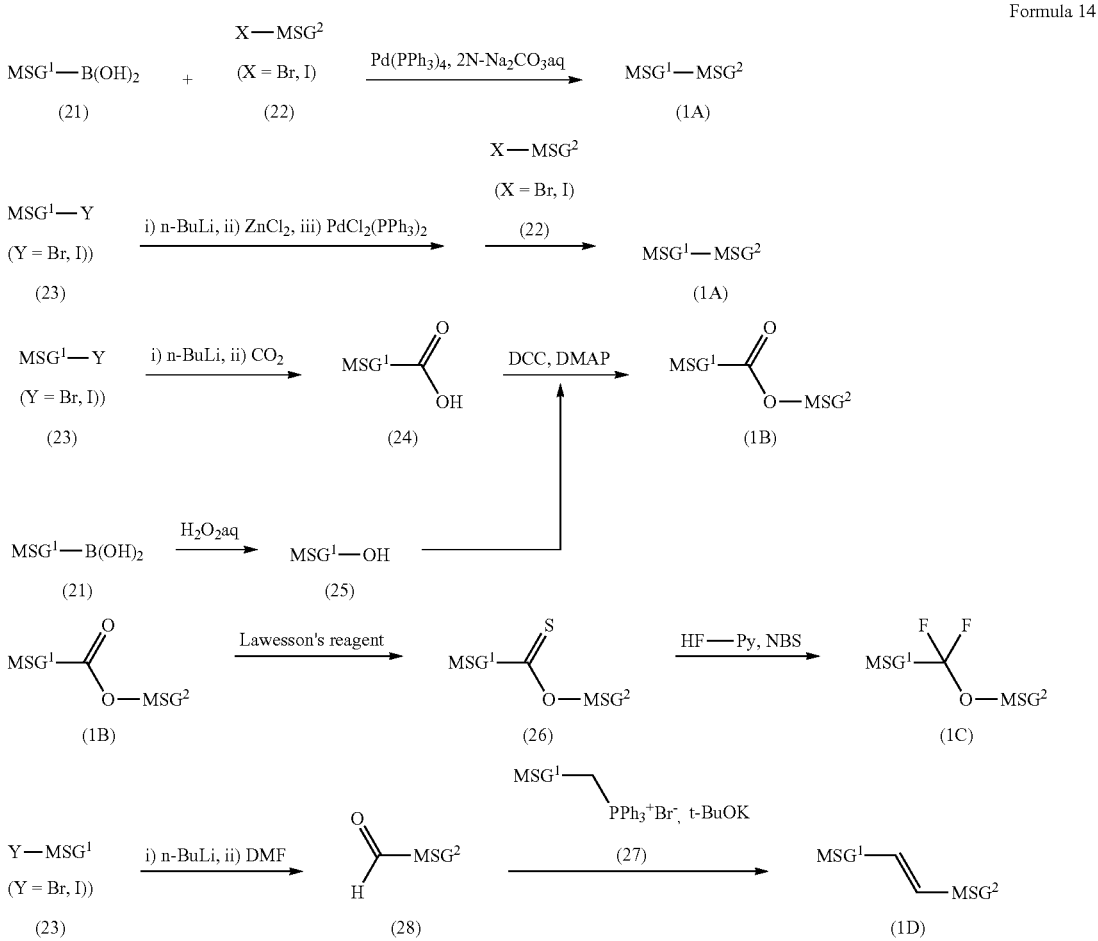

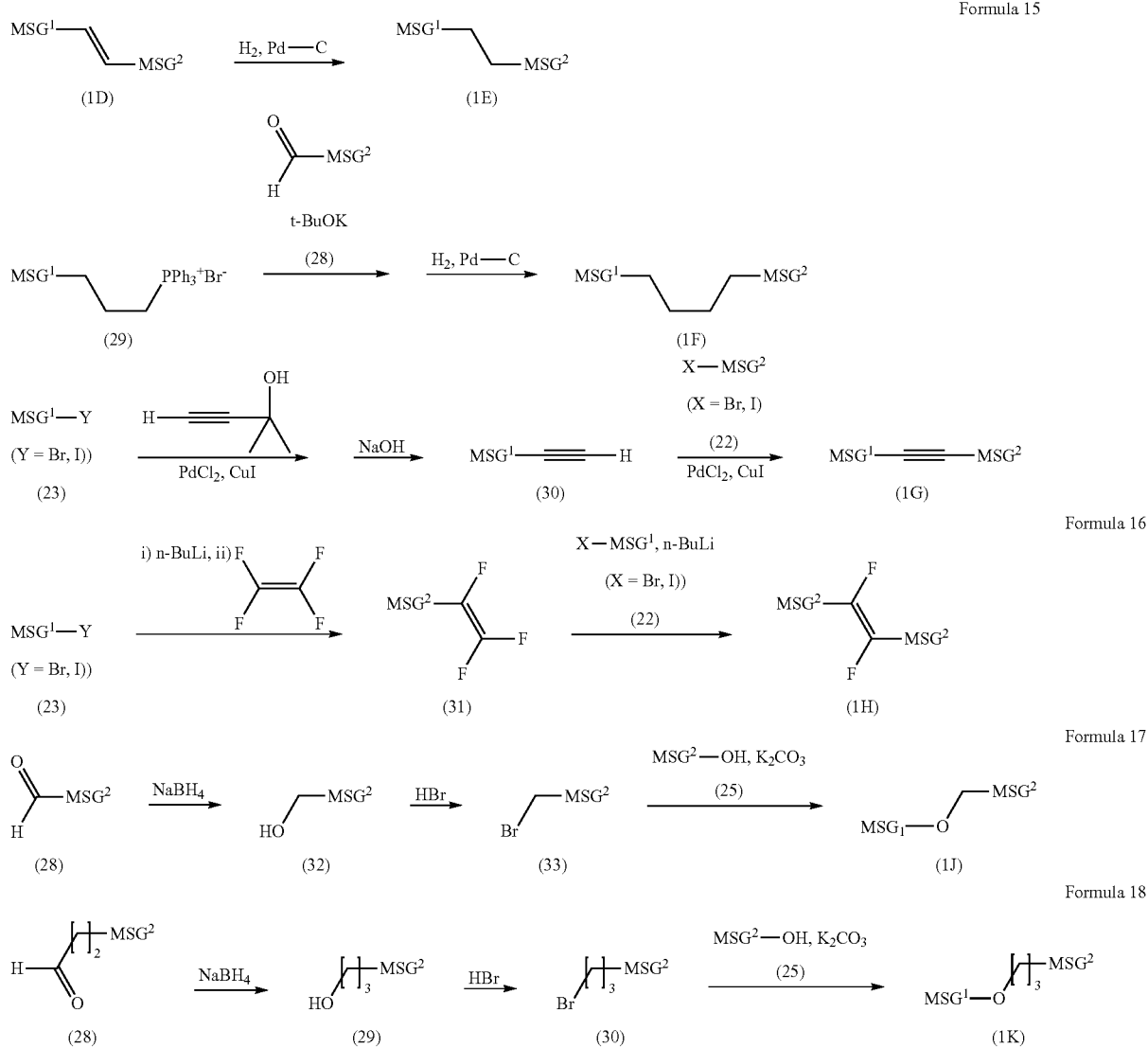

(i) Formation of a Single Bond

Compound (1A) is prepared by allowing aryl boronic acid (21) to react, in the presence of an aqueous solution of carbonate and a catalyst such as tetrakis(triphenylphosphine)palladium, with compound (22) prepared according to a known method. Compound (1A) is also prepared by allowing compound (23) prepared according to a known method to react with n-butyllithium and subsequently with zinc chloride, and further with compound (22) in the presence of a catalyst such as dichlorobis(triphenylphosphine)palladium.

(ii) Formation of —COO— or —OCO—

Carboxylic acid (24) is obtained by allowing compound (23) to react with n-butyllithium and subsequently with carbon dioxide. Compound (1B) having —COO— is prepared by dehydrating, in the presence of 1,3-dicyclohexylcarbodiimide (DCC) and 4-dimethylaminopyridine (DMAP), carboxylic acid (24) and phenol (25) prepared according to a known method. A compound having —OCO— is also prepared according to the method.

(iii) Formation of —CF$_2$O or OCF$_2$

Compound (26) is obtained by treating compound (1B) with a thiation reagent such as Lawesson's reagent. Compound (1C) having —CF$_2$O— is prepared by fluorinating compound (26) with a hydrogen fluoride-pyridine complex and N-bromosuccinimide (NBS). See M. Kuroboshi et al., Chem. Lett., 1992, 827 as a literature of oxidative desulfuration-fluorination. Compound (1C) is also prepared by fluorinating compound (26) with (diethylamino)sulfurtrifluoride (DAST). See W. H. Bunnelle et al., J. Org. Chem. 1990, 55, 768. A compound having —OCF$_2$— is also prepared according to the method. The bonding groups can also be formed according to the method described in Peer. Kirsch et al., Angew. Chem. Int. Ed. 2001, 40, 1480.

(iv) Formation of —CH═CH—

Aldehyde (28) is obtained by treating compound (23) with n-butyllithium and then allowing a treated product to react with formamide such as N,N-dimethylformamide (DMF). Compound (1D) is prepared by allowing aldehyde (28) to react with phosphorus ylide generated by treating with a base such as potassium tert-butoxide phosphonium salt (27) prepared according to a known method. A cis form may be generated depending on reaction conditions, and therefore the cis form is isomerized into a trans form according to a known method, when necessary.

(v) Formation of —(CH$_2$)$_2$—
Compound (1E) is prepared by hydrogenating compound (1D) in the presence of a catalyst such as palladium on carbon.
(vi) Formation of —(CH$_2$)$_4$—
Phosphonium salt (29) is used in place of phosphonium salt (27), and a compound having —(CH$_2$)$_2$—CH═CH— is obtained in accordance with the method of section (iv). Compound (1F) is prepared by catalytically hydrogenating the compound.
(vii) Formation of —C≡C—
Compound (30) is obtained by allowing compound (23) to react with 2-methyl-3-butyn-2-ol in the presence of a catalyst of dichloropalladium and copper halide, and then deprotecting the reacted product under basic conditions. Compound (1G) is prepared by allowing compound (30) to react with compound (22) in the presence of a catalyst of dichloropalladium and copper halide
(viii) Formation of —CF═CF—
Compound (31) is obtained by treating compound (23) with n-butyllithium, and then allowing the treated product to react with tetrafluoroethylene. Compound (1H) is prepared by treating compound (22) with n-butyllithium, and then allowing the treated product to react with compound (31).
(ix) Formation of —CH$_2$O— or —OCH$_2$—
Compound (32) is obtained by reducing compound (28) with a reducing agent such as sodium boron hydride. Compound (33) is obtained by halogenating compound (32) with hydrobromic acid or the like. Compound (1J) is prepared by allowing compound (33) to react with compound (25) in the presence of potassium carbonate or the like.
(x) Formation of —(CH$_2$)$_3$O— or —O(CH$_2$)$_3$—
Compound (29) is used in place of compound (32), and compound (1K) is prepared according to the method described in section (ix).
(xi) Formation of —(CF$_2$)$_2$—
A compound having —(CF$_2$)$_2$— is obtained by fluorinating diketone (—COCO—), in the presence of a hydrogen fluoride catalyst, with sulfur tetrafluoride according to the method described in J. Am. Chem. Soc., 2001, 123, 5414 with regard to the liquid crystal compound having —(CF$_2$)$_2$—.

Liquid Crystal Composition

Hereinafter, a liquid crystal composition of the invention will be explained. A component of the liquid crystal composition is characterized by containing at least one compound (I). The composition may contain two or more of compound (I), or may be formed of only compound (I). Moreover, when the liquid crystal composition of the invention is prepared, for example, components can also be selected by taking the dielectric anisotropy of compound (1) into consideration. The liquid crystal composition prepared by selecting the components has a low viscosity, a suitable dielectric anisotropy and a low threshold voltage, and also has a high maximum temperature of the nematic phase, and a low minimum temperature of the nematic phase.

Liquid Crystal Composition (1)

The liquid crystal composition of the invention is required to contain, as component A, compound (I). The liquid crystal composition of the invention may be a composition consisting essentially of the component A, or a composition containing component A and any other component whose name is not described herein, but when a component selected from the group of components B, C, D and E described below is added to component A, a liquid crystal composition having a variety of characteristics can be provided.

As a component to be added to component A, a mixture of component B containing at least one compound selected from the group of compounds represented by formulas (2), (3) and (4), and/or component C containing at least one kind of compound selected from the group of compound represented by formula (5), and/or component D containing at least one kind of compound selected from the group of compounds represented by formulas (6), (7), (8), (9), (10) and (11) is preferred. Furthermore, when component E containing at least one kind of compound selected from the group of compounds represented by formulas (12), (13) and (14) is mixed, the threshold voltage, the temperature range of the liquid crystal phase, the refractive index anisotropy, the dielectric anisotropy, the viscosity or the like can be adjusted.

Moreover, each component of the liquid crystal composition used for the invention has no significant difference in physical characteristics, even when each component is an analog including an isotopic element of each element.

Among types of component B above, suitable examples of compounds represented by formula (2) include compounds (2-1) to (2-16), suitable examples of compounds represented by formula (3) include compounds (3-1) to (3-112), and suitable examples of compounds represented by formula (4) include compounds (4-1) to (4-54).

Formula 19

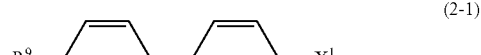
(2-1)

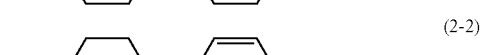
(2-2)

(2-3)

(2-4)

(2-5)

(2-6)

(2-7)

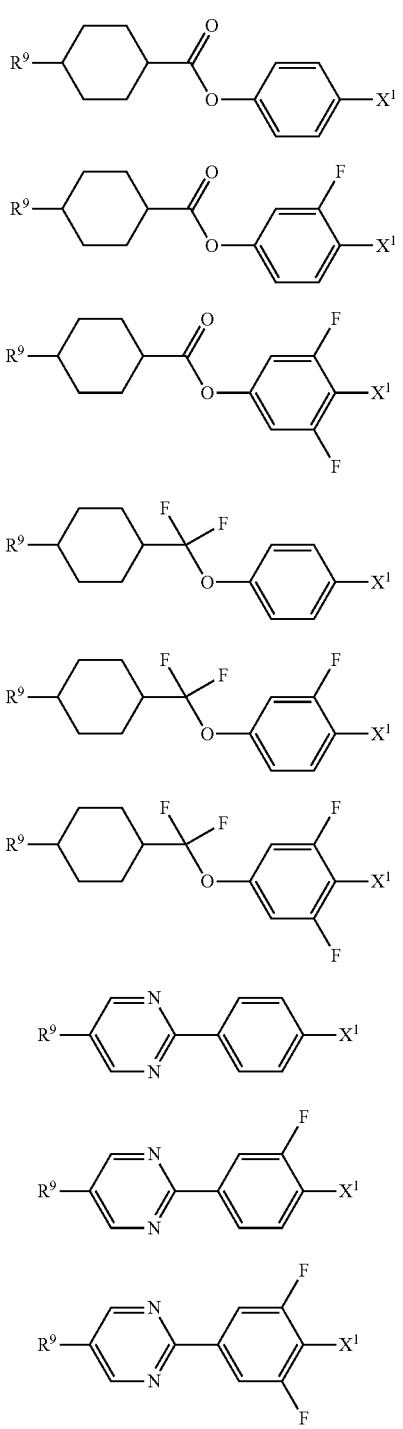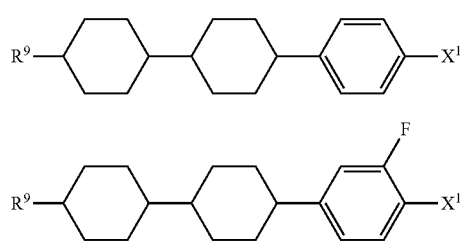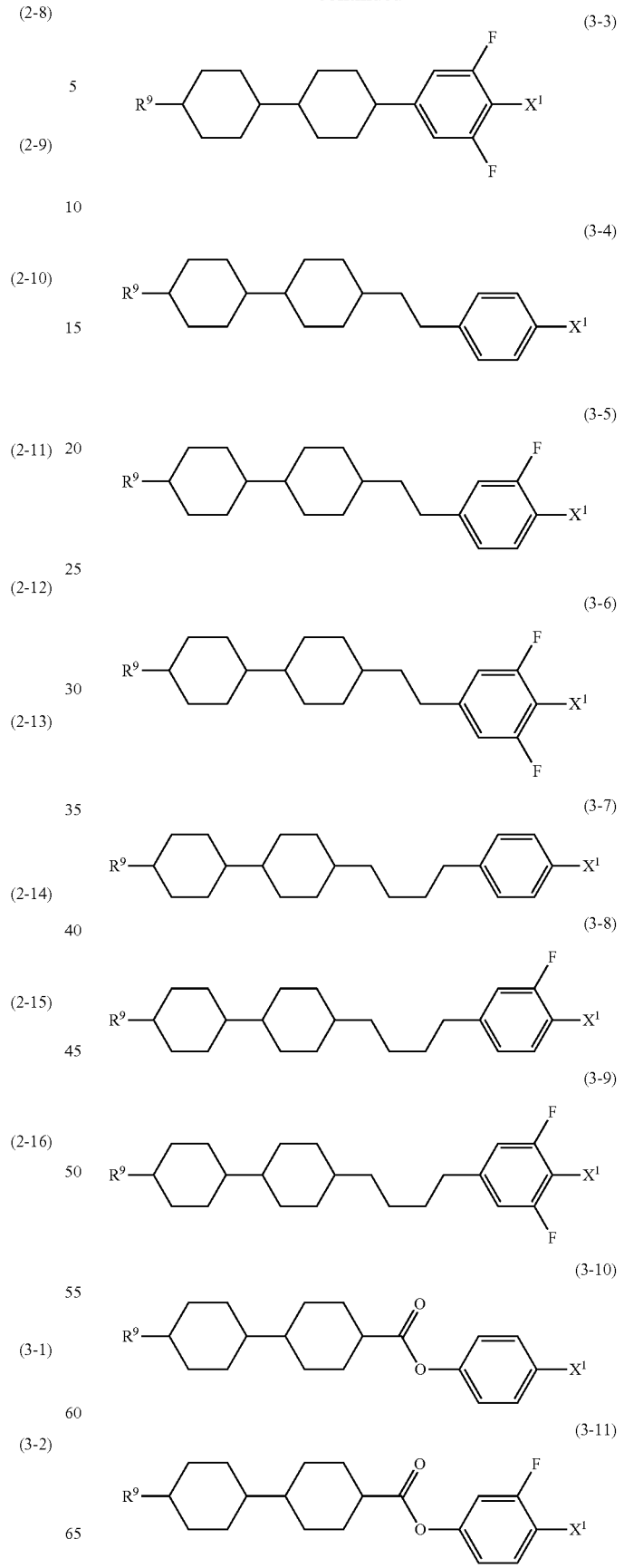

(3-12)
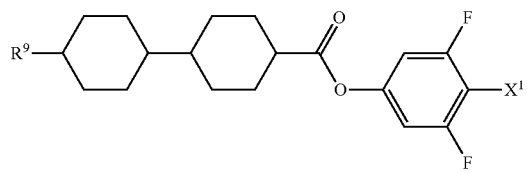
(3-13)
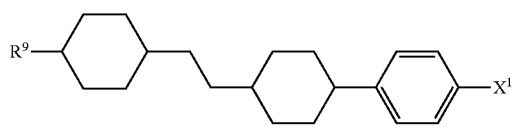
(3-14)
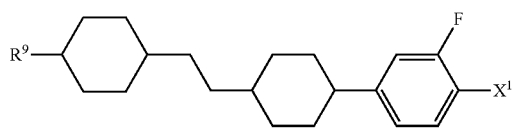
(3-15)
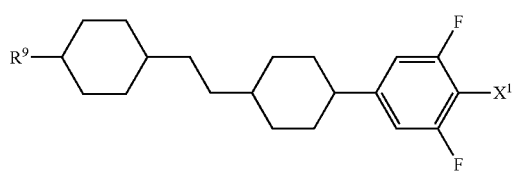
(3-16)
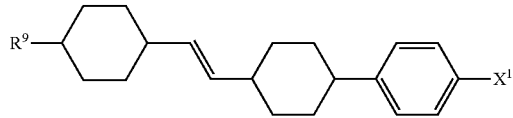
(3-17)
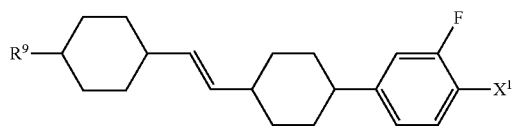
(3-18)
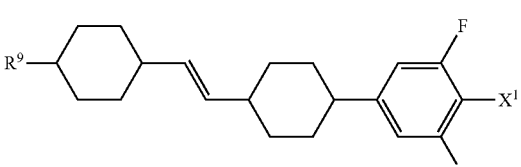
(3-19)
(3-20)
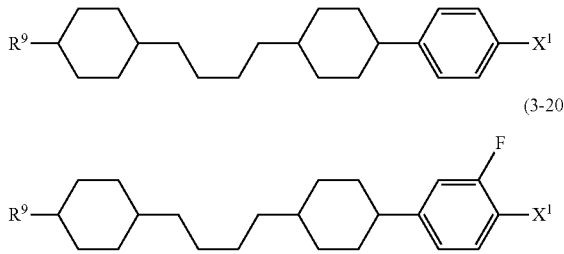
(3-21)
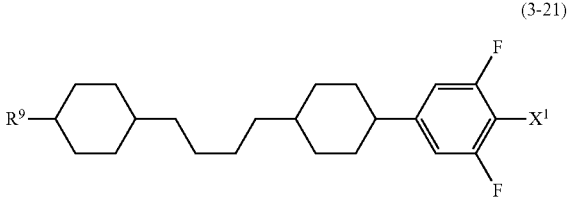
(3-22)
(3-23)
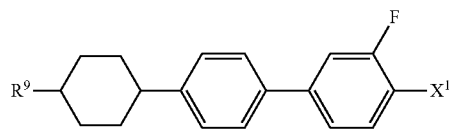
(3-24)
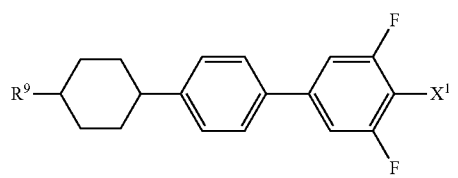
Formula 21
(3-25)
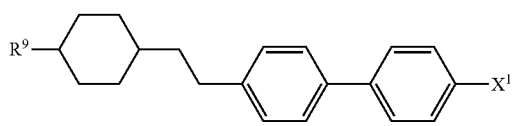
(3-26)
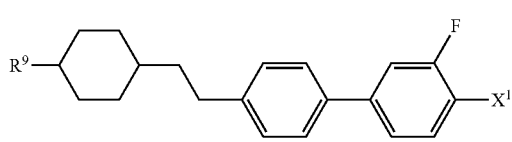
(3-27)
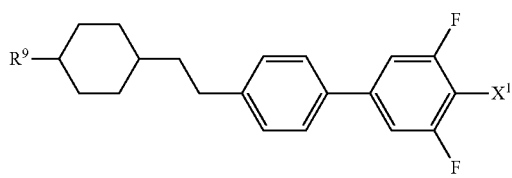
(3-28)
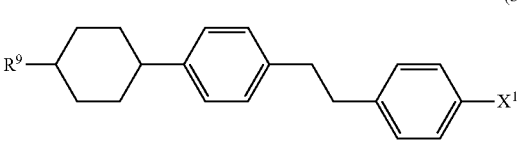
(3-29)
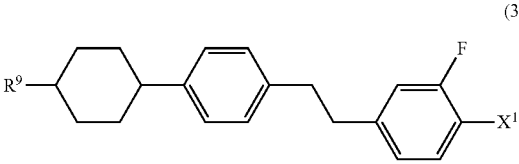

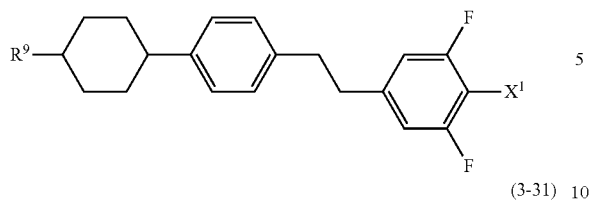
(3-30)
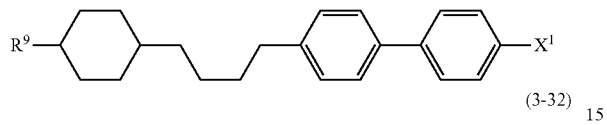
(3-31)
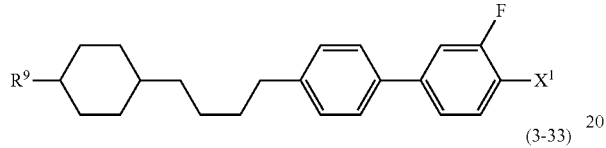
(3-32)
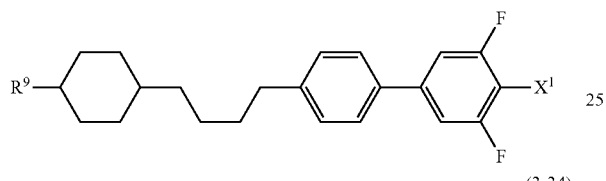
(3-33)
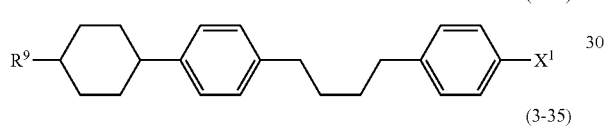
(3-34)
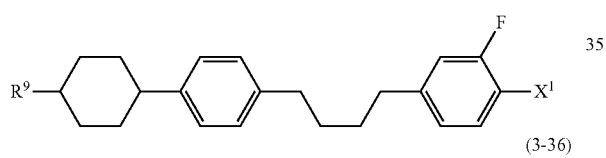
(3-35)
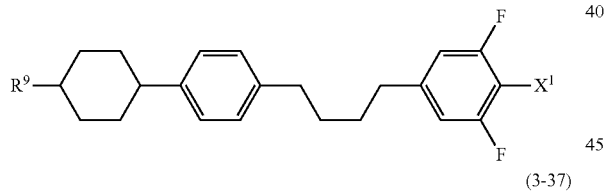
(3-36)
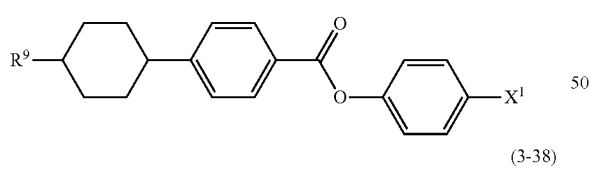
(3-37)
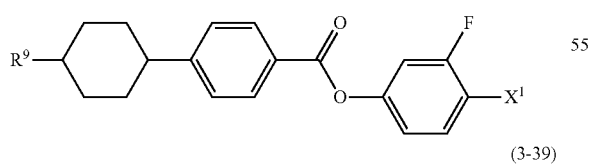
(3-38)
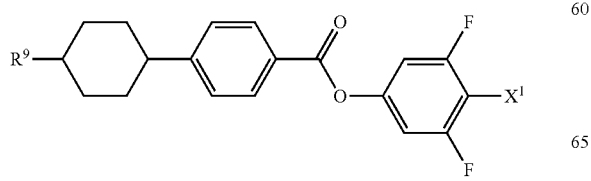
(3-39)
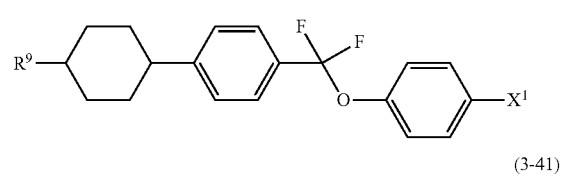
(3-40)
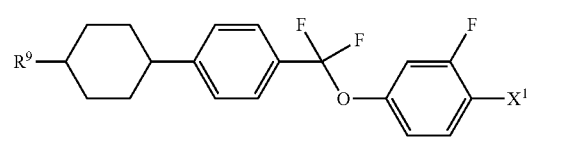
(3-41)
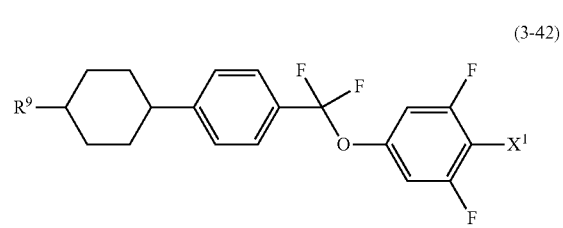
(3-42)
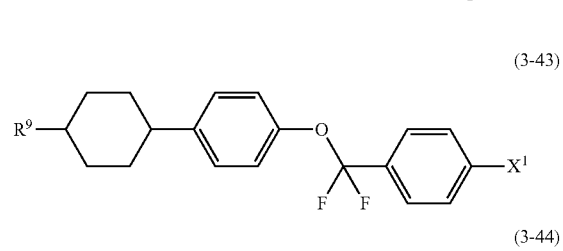
(3-43)
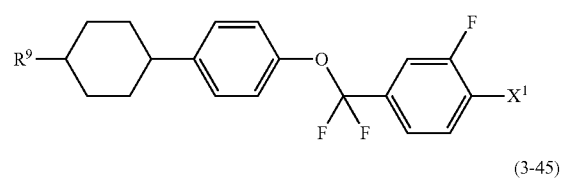
(3-44)
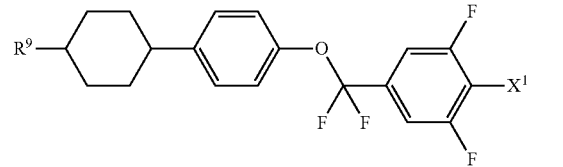
(3-45)
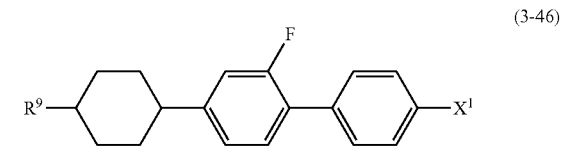
(3-46)
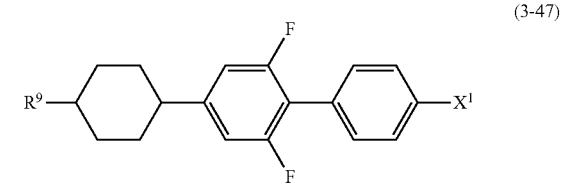
(3-47)
(3-48)

(3-49)
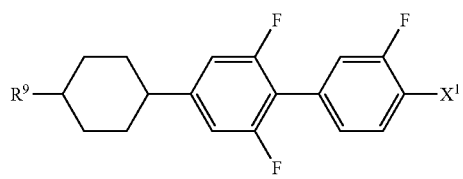
(3-50)
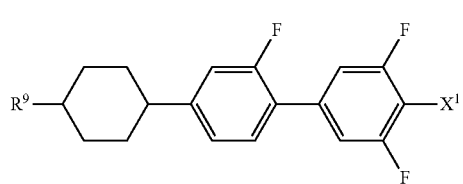
(3-51)
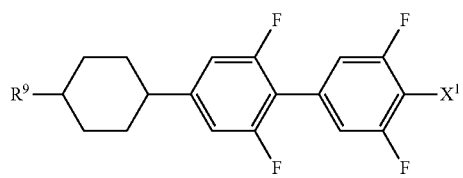
Formula 22
(3-52)
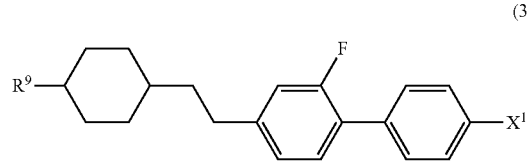
(3-53)
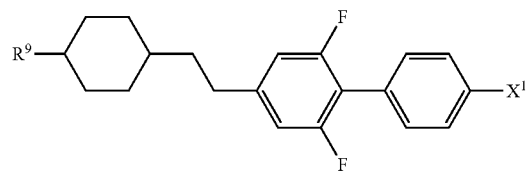
(3-54)
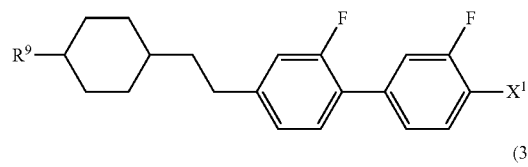
(3-55)
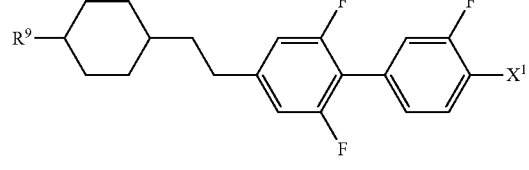
(3-56)
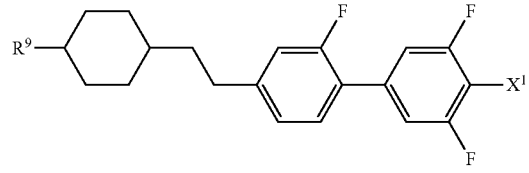
(3-57)
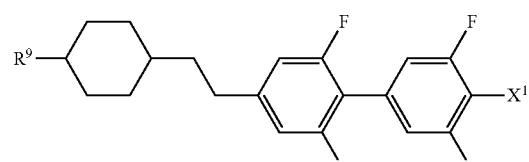
(3-58)
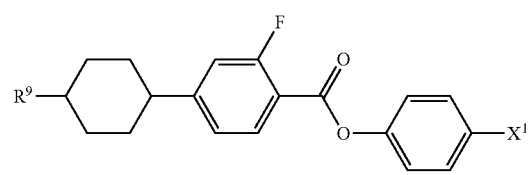
(3-59)
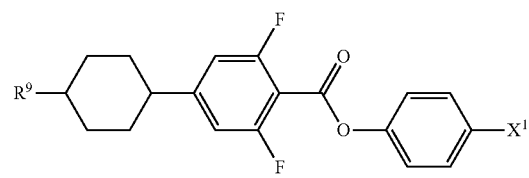
(3-60)
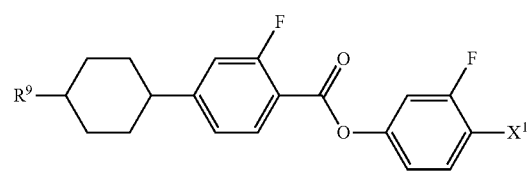
(3-61)
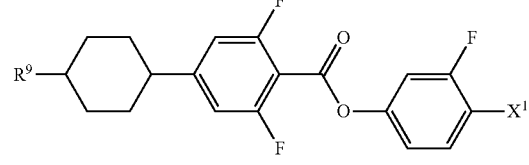
(3-62)
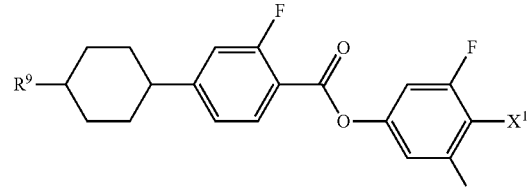
(3-63)
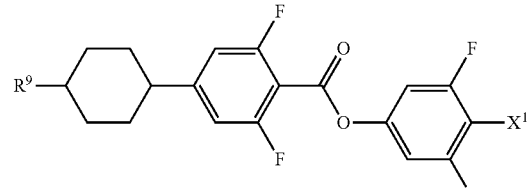
(3-64)
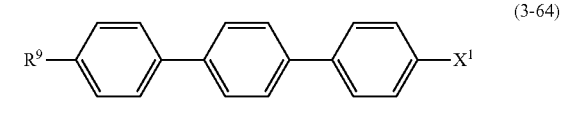

(3-65) 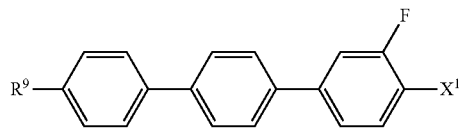
(3-66) 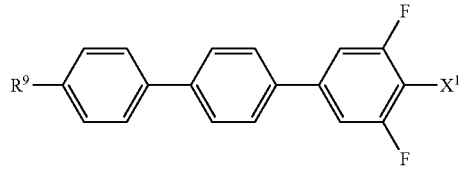
(3-67) 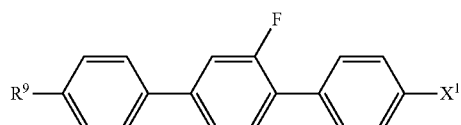
(3-68) 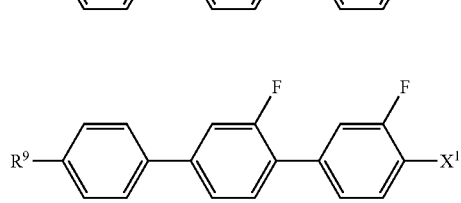
(3-69) 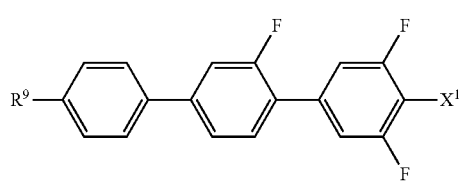
(3-70) 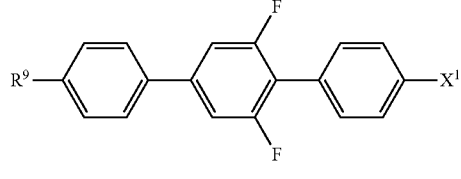
(3-71) 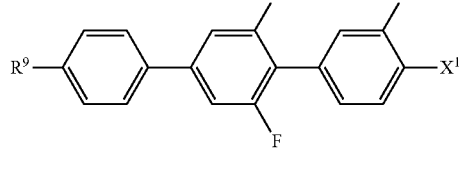
(3-72) 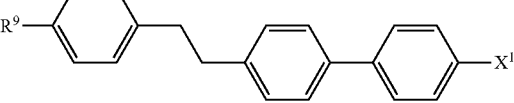
(3-73) 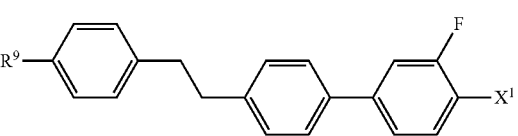
(3-74) 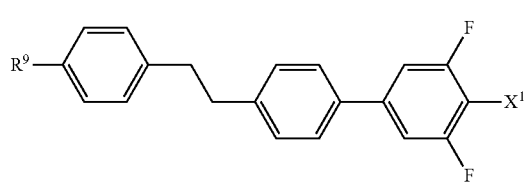
(3-75) 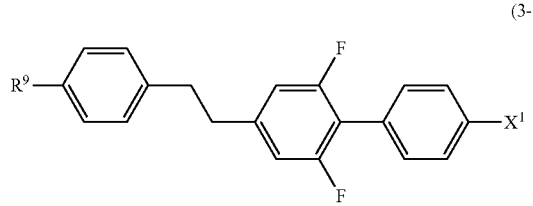
(3-76) 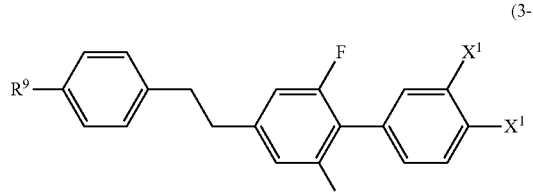
Formula 23
(3-77) 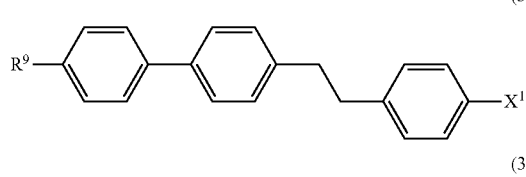
(3-78) 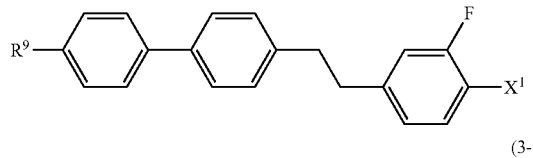
(3-79) 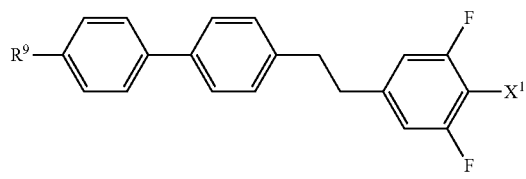
(3-80) 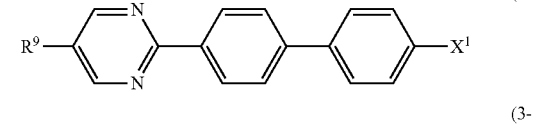
(3-81) 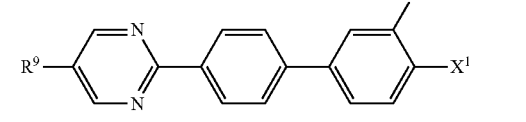
(3-82) 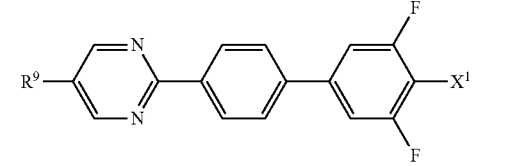

(3-83) 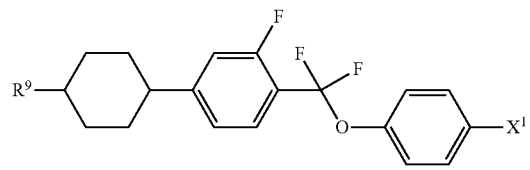
(3-84) 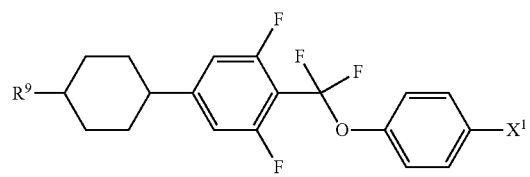
(3-85) 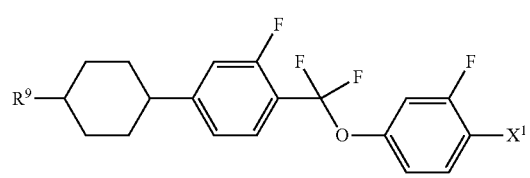
(3-86) 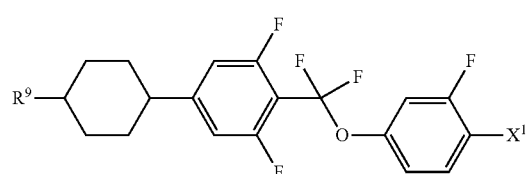
(3-87) 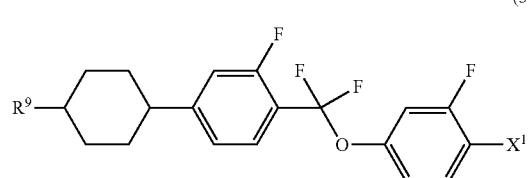
(3-88) 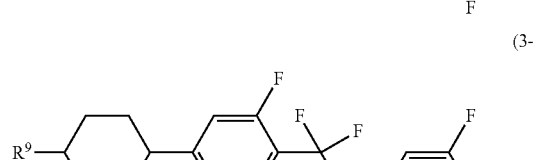
(3-89) 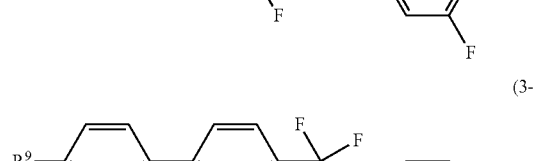
(3-90) 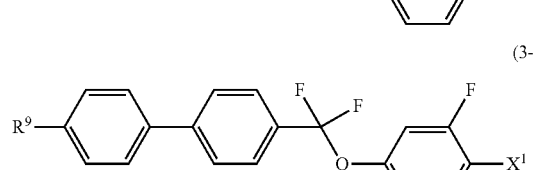
(3-91) 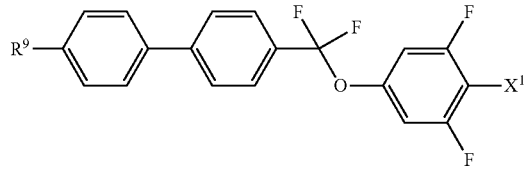
(3-92) 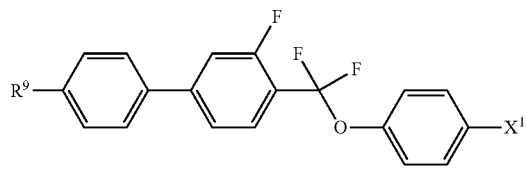
(3-93) 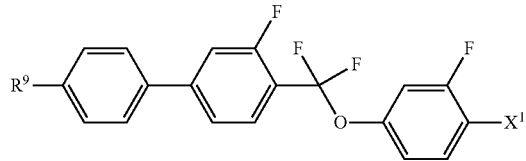
(3-94) 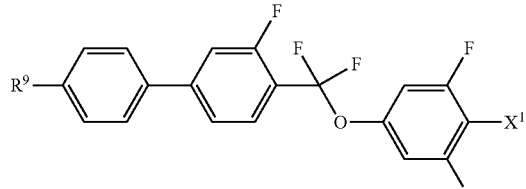
(3-95) 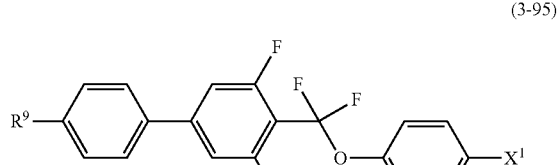
(3-96) 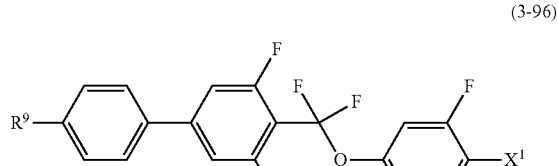
(3-97) 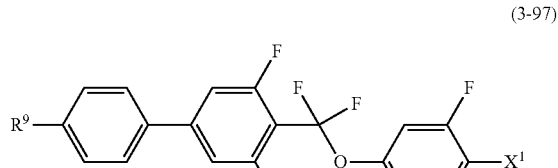
(3-98) 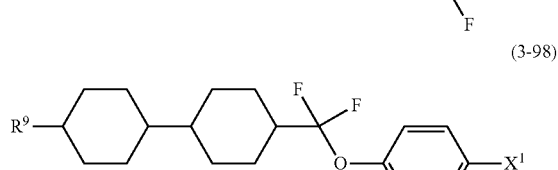

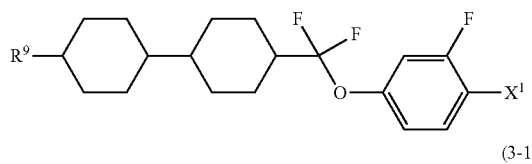
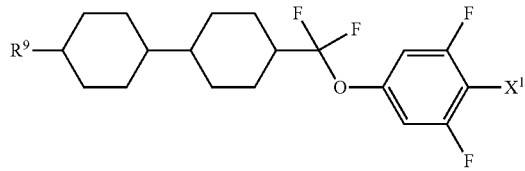
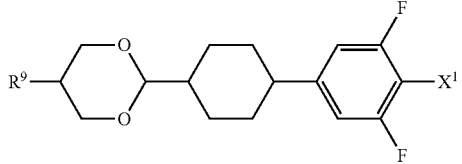
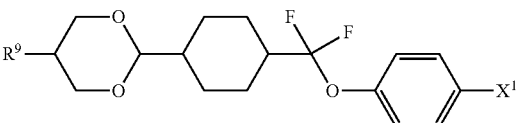

(4-6) 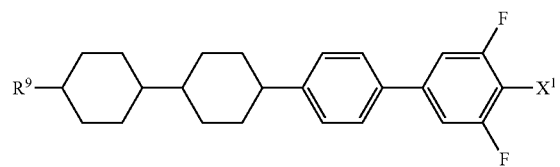
(4-7) 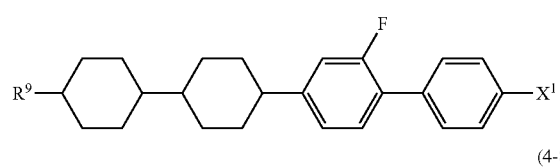
(4-8) 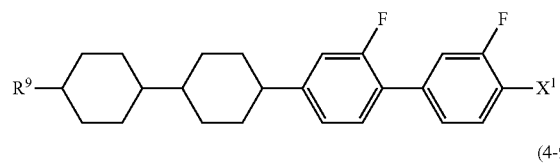
(4-9) 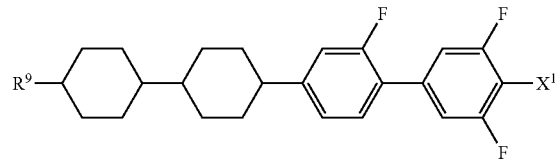
(4-10) 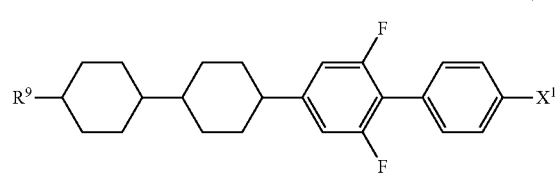
(4-11) 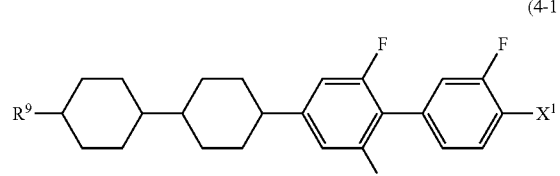
(4-12) 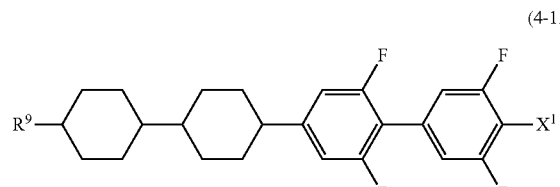
(4-13) 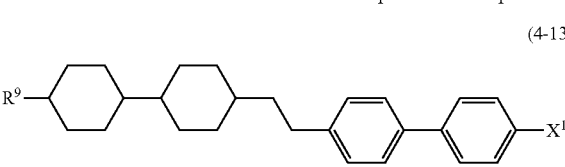
(4-14) 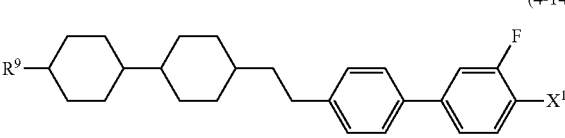
(4-15) 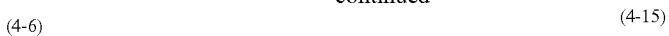
(4-16) 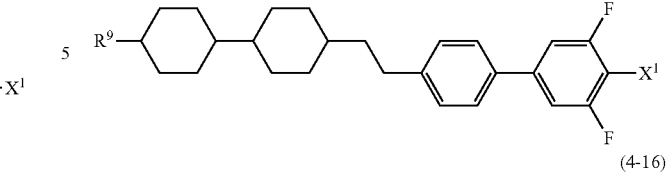
(4-17) 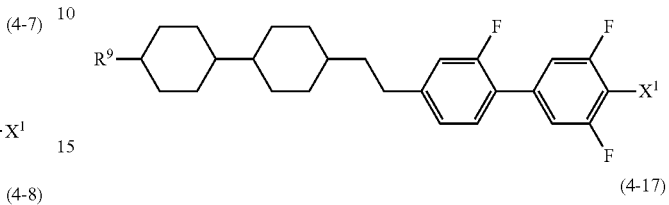
(4-18) 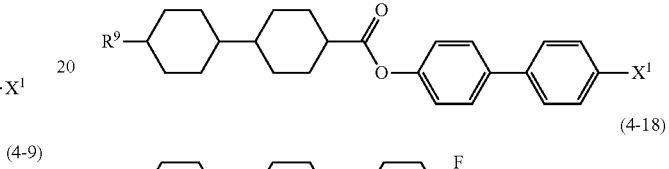
(4-19) 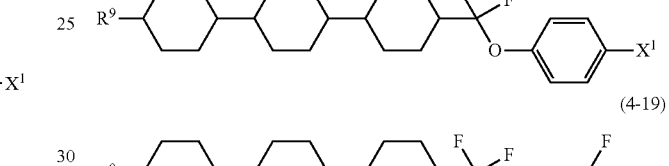
(4-20) 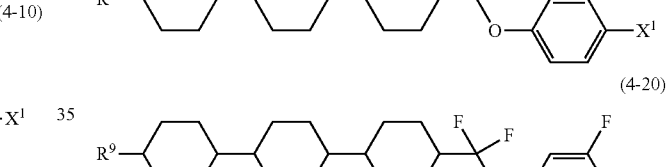
(4-21) 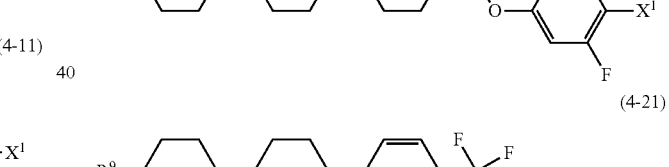
(4-22) 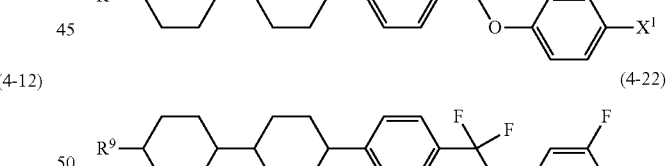
(4-23) 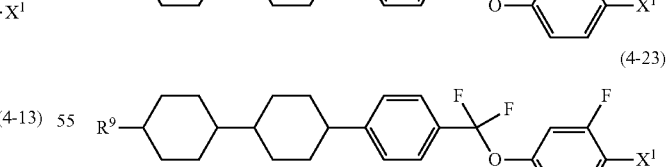
(4-24) 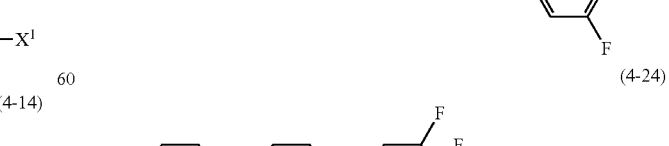
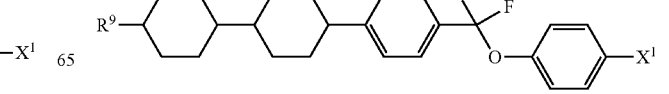

-continued
(4-25)
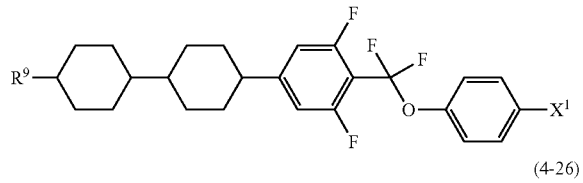
(4-26)
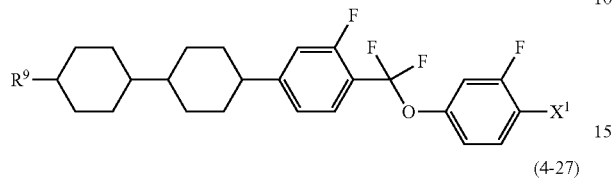
(4-27)
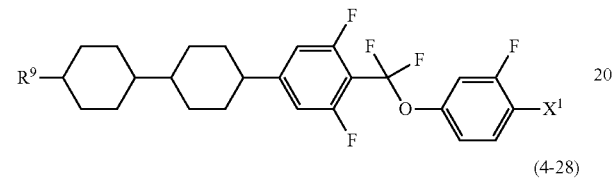
(4-28)
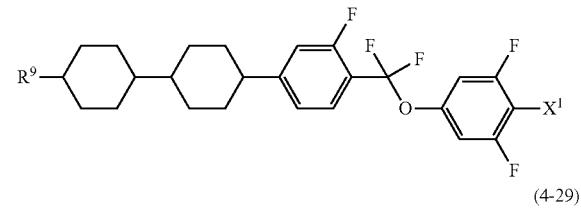
(4-29)
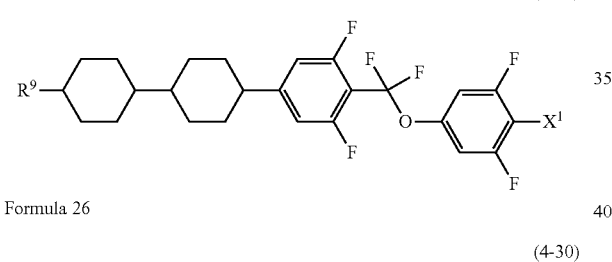
Formula 26
(4-30)
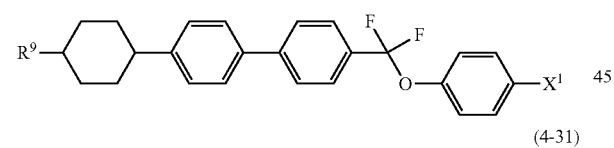
(4-31)
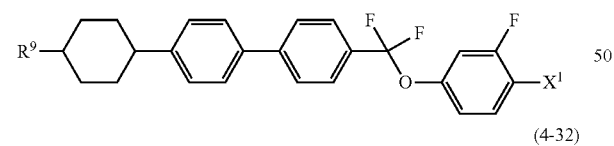
(4-32)
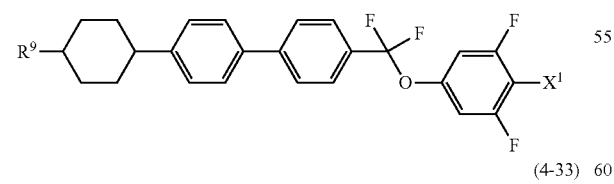
(4-33)
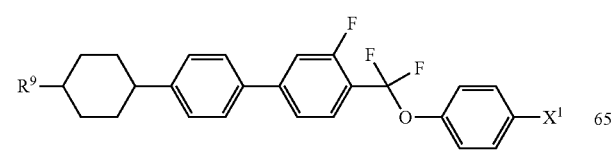
-continued
(4-34)
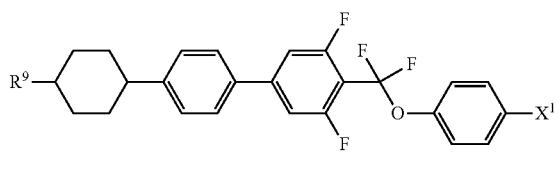
(4-35)
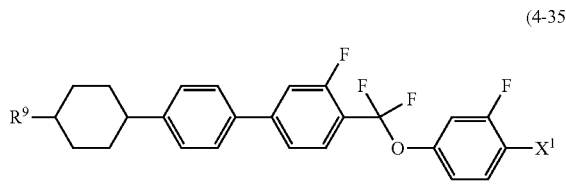
(4-36)
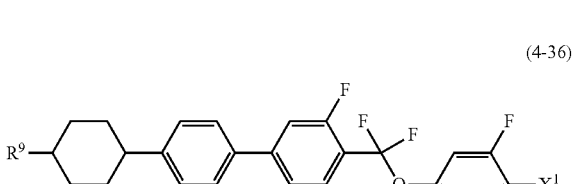
(4-37)
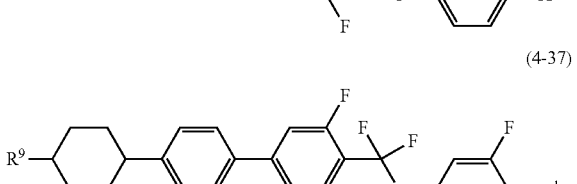
(4-38)
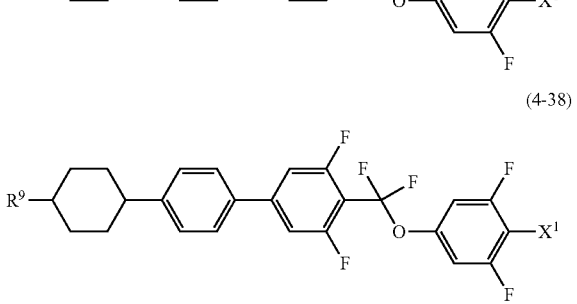
(4-39)
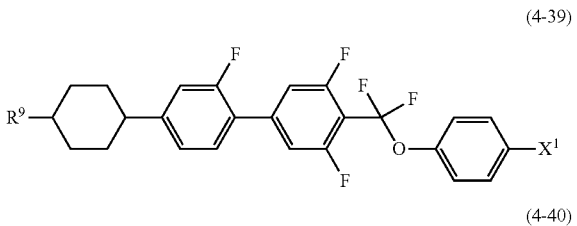
(4-40)
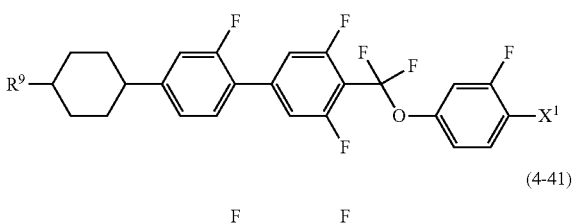
(4-41)
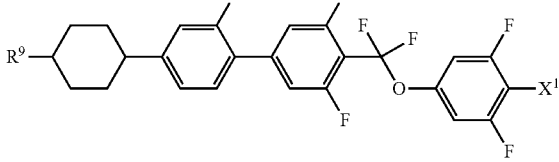

(4-42)
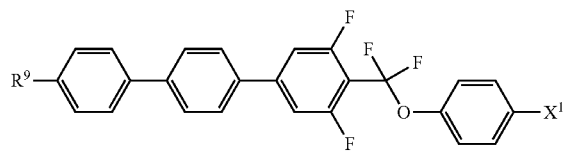

(4-43)
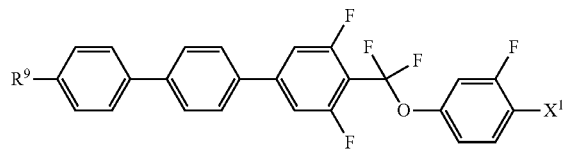

(4-44)
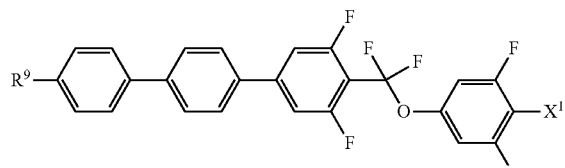

(4-45)
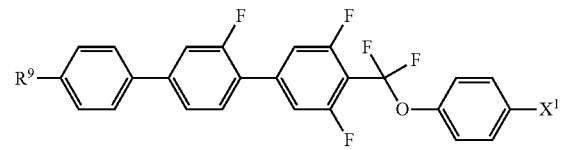

(4-46)
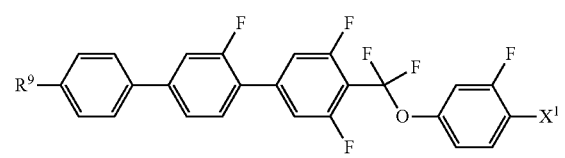

(4-47)
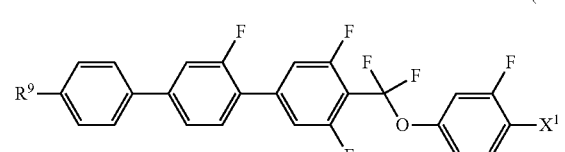

(4-48)
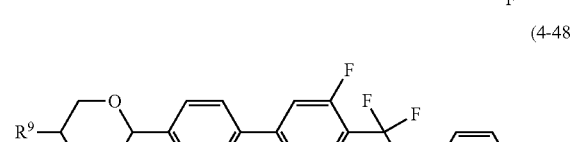

(4-49)
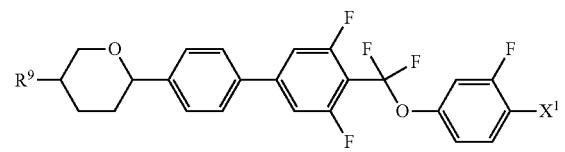

(4-50)
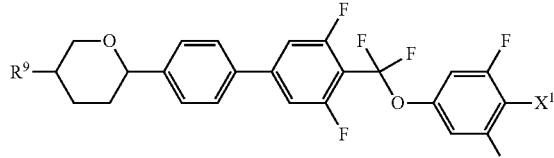

(4-51)
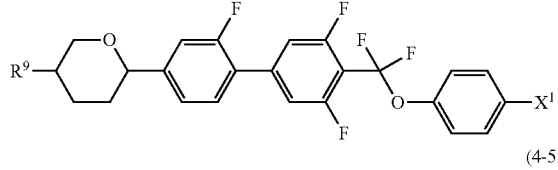

(4-52)
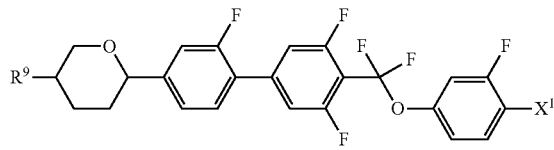

(4-53)
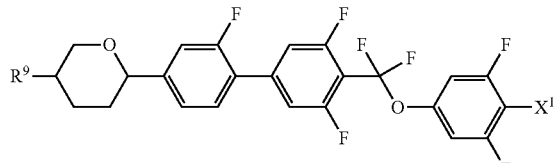

(4-54)
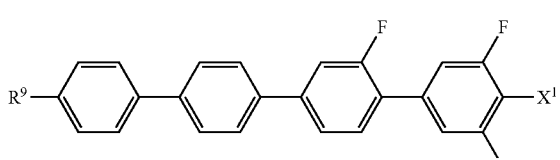

In the formulas, $R^9$ and $X^1$ are defined in a manner identical with the definitions described above.

Compounds (2) to (4), namely, component B, have a positive dielectric anisotropy and a superb thermal stability and chemical stability, and therefore are used for preparing a liquid crystal composition for the TFT mode and the PSA mode. Content of component B in the liquid crystal composition according to the invention is suitably in the range of approximately 1% to approximately 99% by weight, preferably, approximately 10% to approximately 97% by weight, further preferably, approximately 40% to approximately 95% by weight, based on the total weight of the liquid crystal composition. Moreover, the viscosity can be adjusted by further incorporating compounds represented by formulas (12) to (14) (component E) into the composition.

Suitable examples of compounds represented by formula (5), namely, component C, include compounds represented by formulas (5-1) to (5-64).

Formula 27

(5-1)
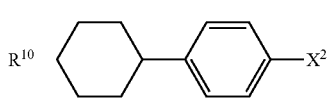

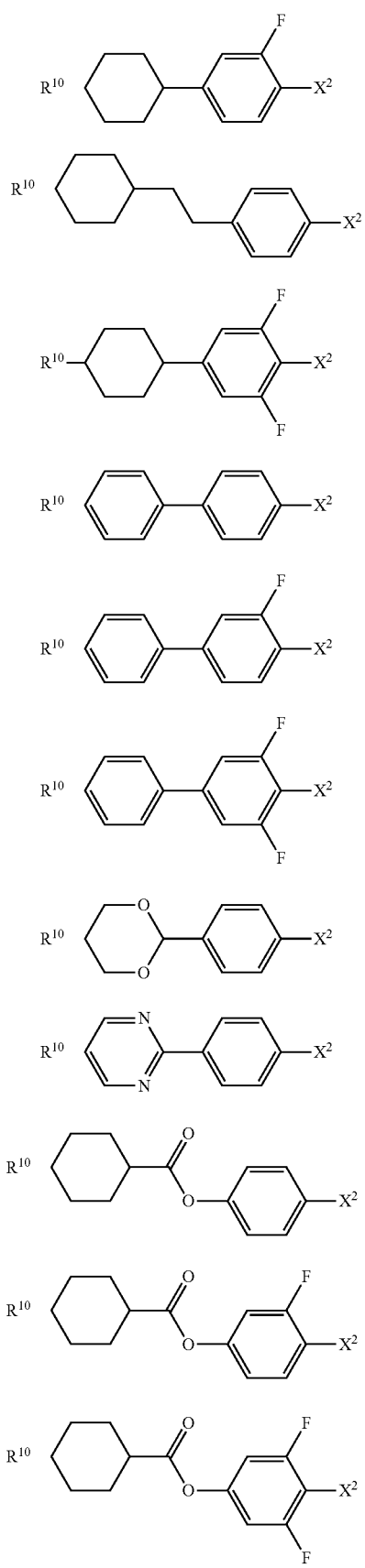
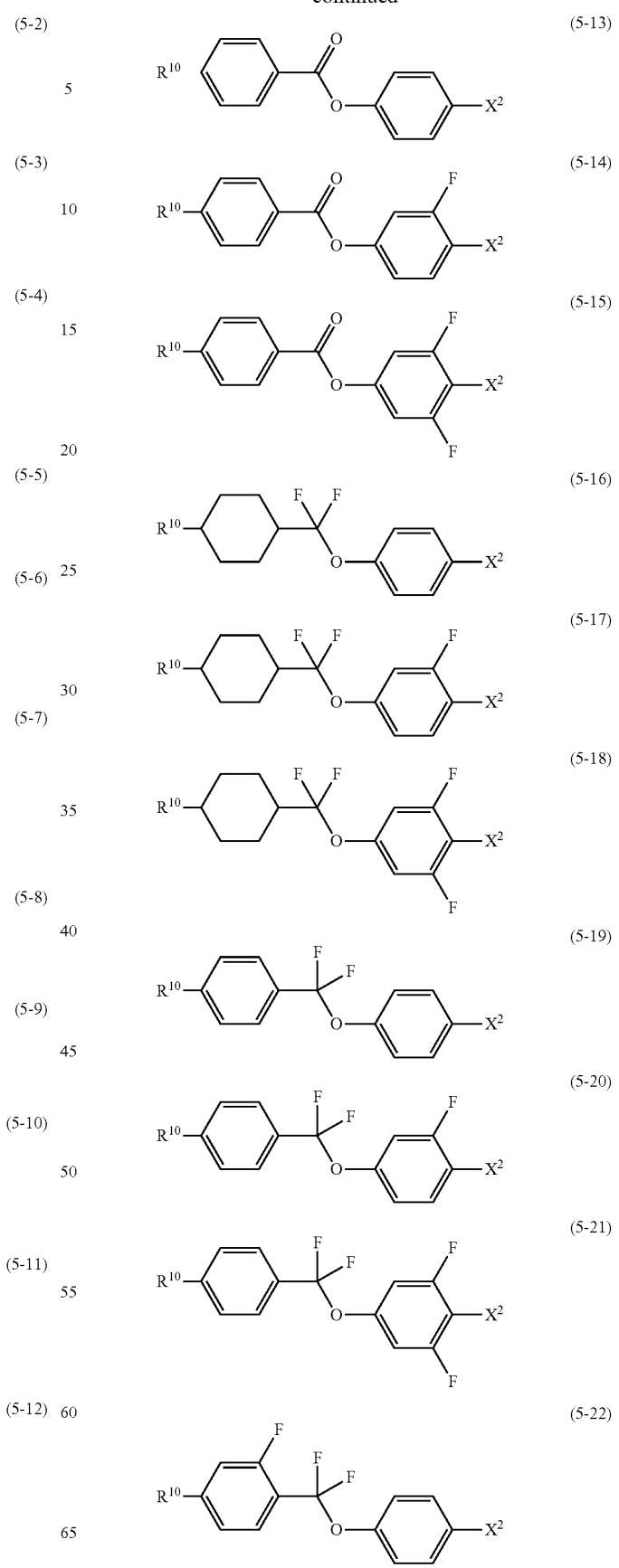

(5-23) 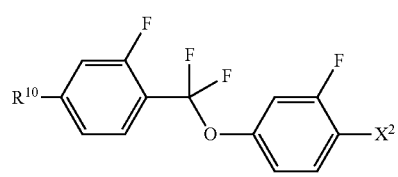
(5-24) 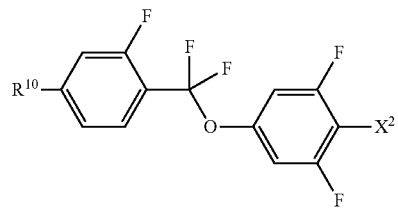
(5-25) 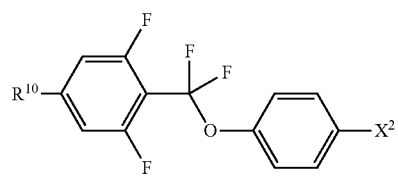
(5-26) 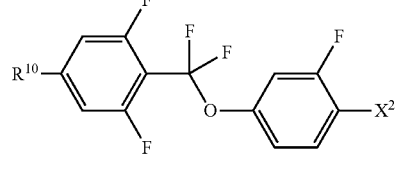
(5-27) 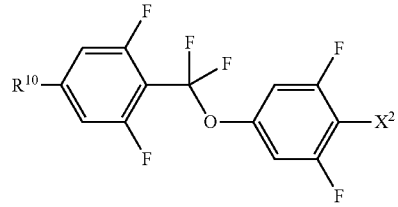
Formula 28
(5-28) 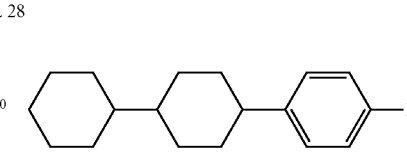
(5-29) 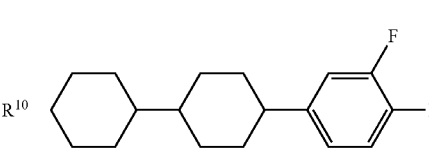
(5-30) 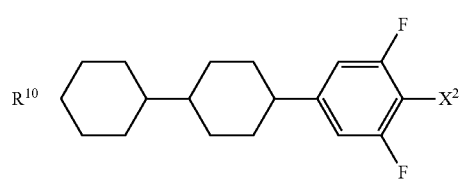
(5-31) 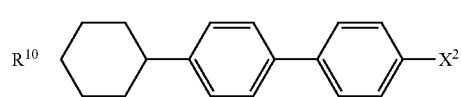
(5-32) 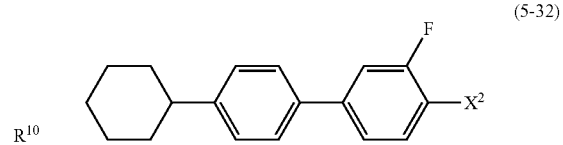
(5-33) 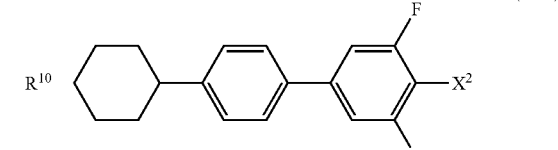
(5-34) 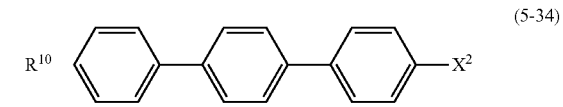
(5-35) 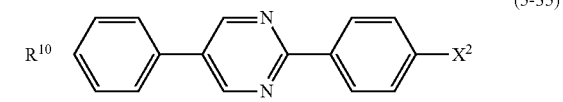
(5-36) 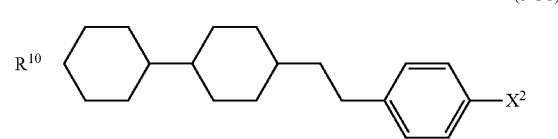
(5-37) 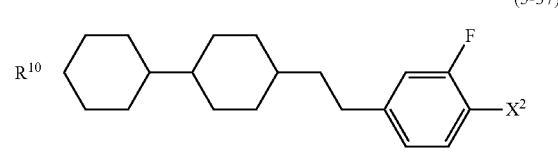
(5-38) 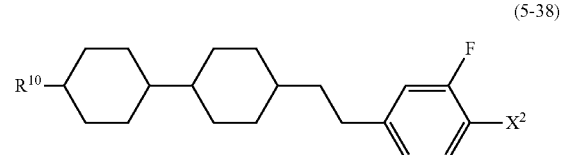
(5-39) 
(5-40) 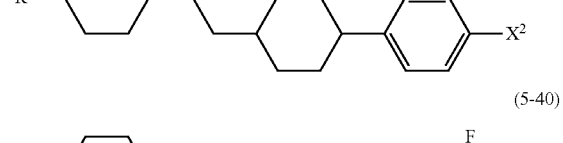
(5-41) 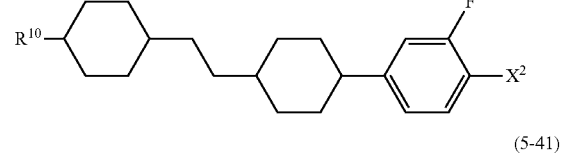

(5-42)
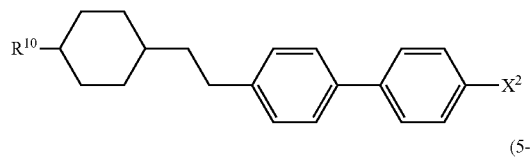
(5-43)
(5-44)
(5-45)
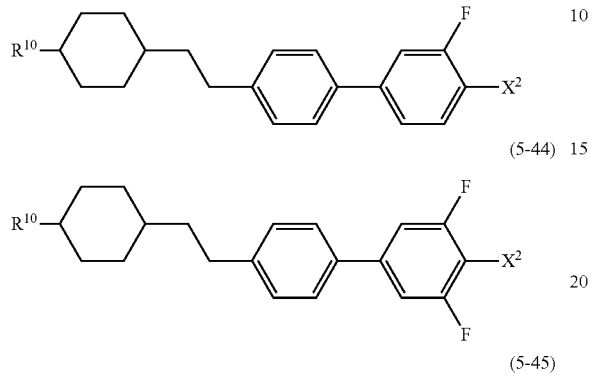
(5-46)
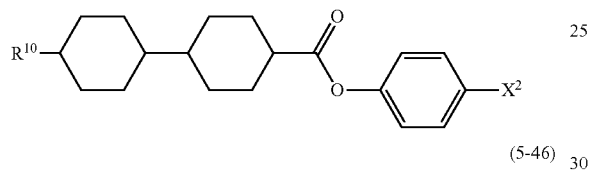
(5-47)
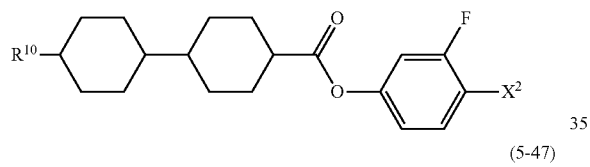
(5-48)
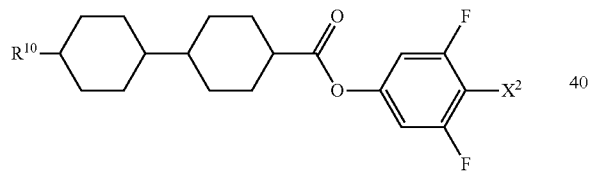
(5-49)
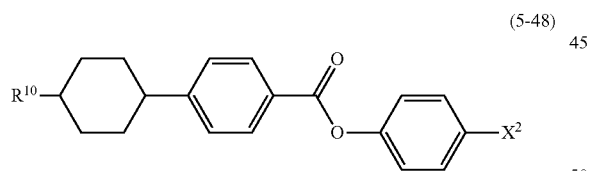
Formula 29
(5-50)
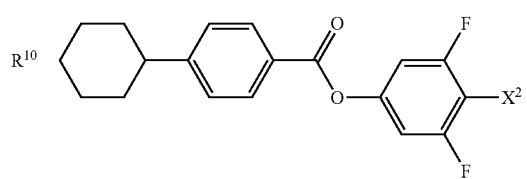
(5-51)
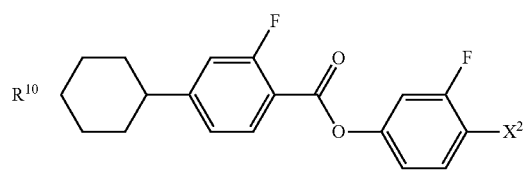
(5-52)
(5-53)
(5-54)
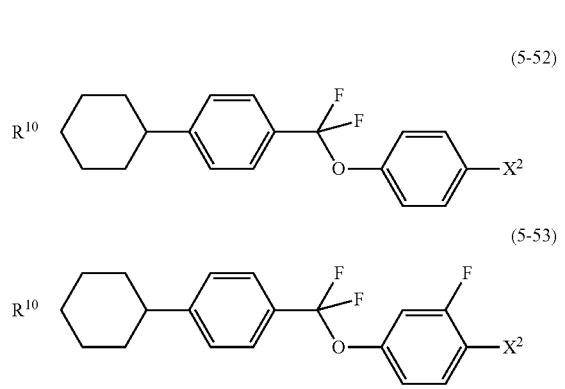
(5-55)
(5-56)
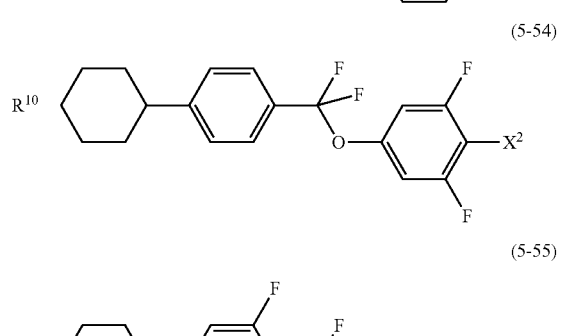
(5-57)
(5-58)
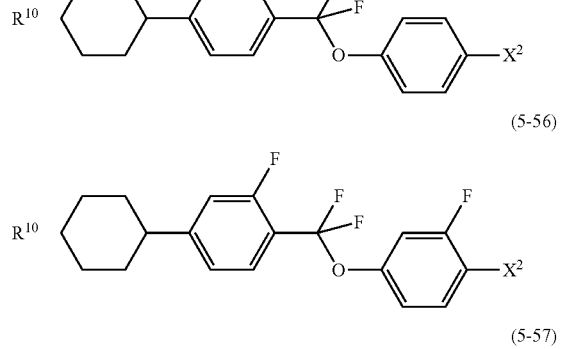

-continued

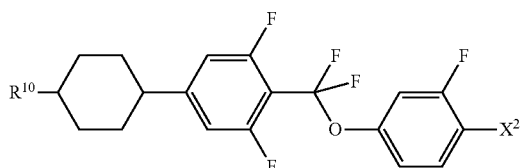 (5-59)

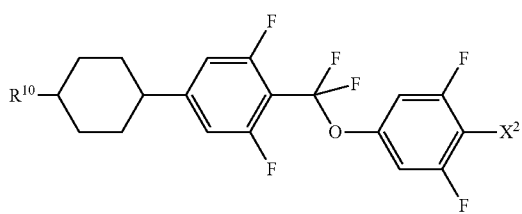 (5-60)

(5-61)

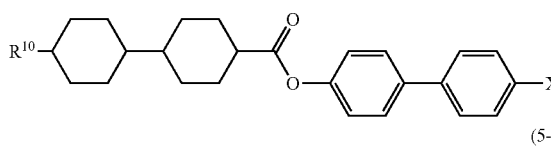 (5-62)

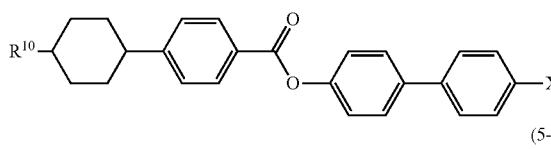 (5-63)

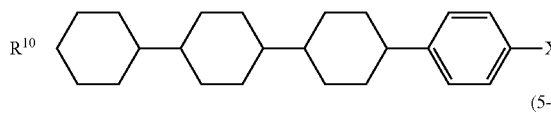 (5-64)

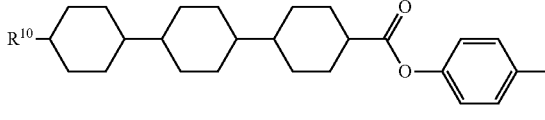

In the formulas, $R^{10}$ and $X^2$ are defined in a manner identical with the definitions described above.

When o is 2 in formula (5), two of ring $C^2$ may be identical or different.

Compounds represented by formula (5), namely, component C, have a very large positive value of dielectric anisotropy, and therefore are mainly used when preparing a liquid crystal composition for STN, TN or PSA. When component C is incorporated into the composition, the threshold voltage of the liquid crystal composition can be decreased, the viscosity can be adjusted, the refractive index anisotropy can be adjusted, and the temperature range of the liquid crystal phase can be extended. Furthermore, component C can also be utilized for improvement in steepness.

When preparing a liquid crystal composition for STN or TN, content of component C can be applied in the range of approximately 0.1 to approximately 99.9% by mass, preferably, in the range of approximately 10 to approximately 97% by mass, further preferably, in the range of approximately 40 to approximately 95% by mass, based on the total mass of the liquid crystal composition. Moreover, when a component as described later is mixed into the composition, the threshold voltage, the temperature range of the liquid crystal phase, the refractive index anisotropy, the dielectric anisotropy, the viscosity or the like can be adjusted.

Component D containing at least one kind of compound selected from the groups of compounds represented by formulas (6) to (11) is suitably used when preparing a liquid crystal composition having a negative dielectric anisotropy to be used for the vertical alignment mode (VA mode) mode, the polymer sustained alignment mode (PSA mode) or the like.

Suitable examples of compounds represented by formulas (6) to (11) (component D) include compounds (6-1) to (6-6), (7-1) to (7-15), (8-1), (9-1) to (9-3), (10-1) to (10-11) and (11-1) to (11-10).

Formula 30

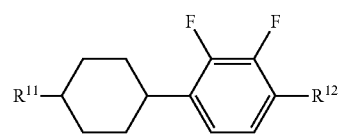 (6-1)

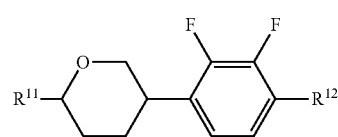 (6-2)

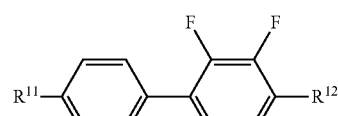 (6-3)

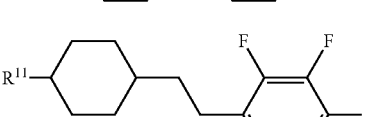 (6-4)

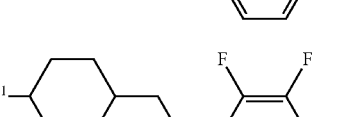 (6-5)

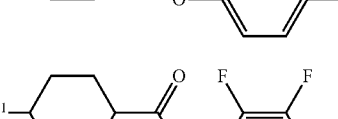 (6-6)

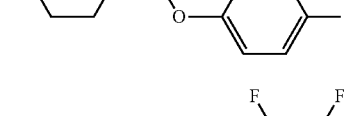 (7-1)

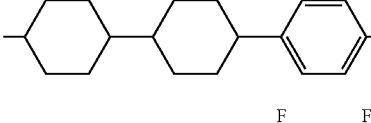 (7-2)

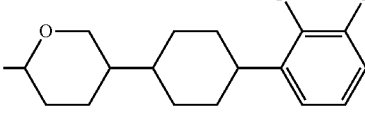 (7-3)

(7-4) 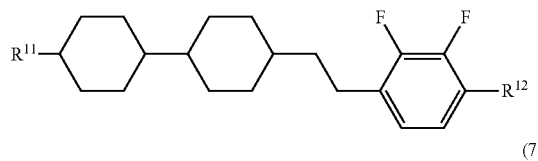
(7-5) 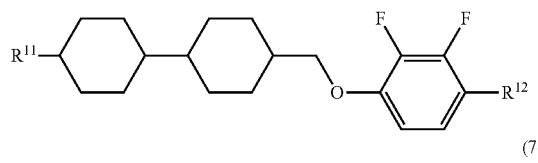
(7-6) 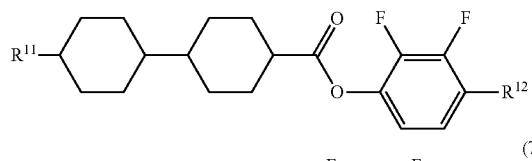
(7-7) 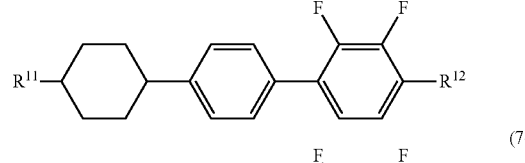
(7-8) 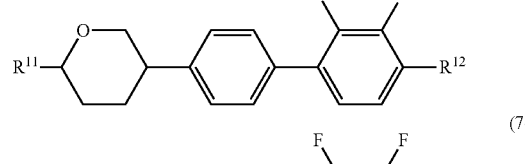
(7-9) 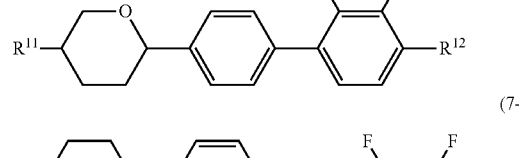
(7-10) 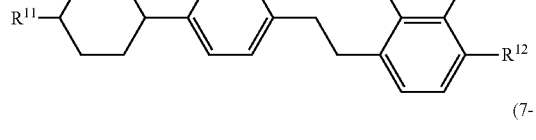
(7-11) 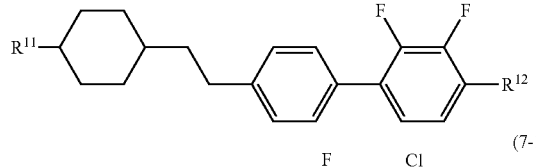
(7-12) 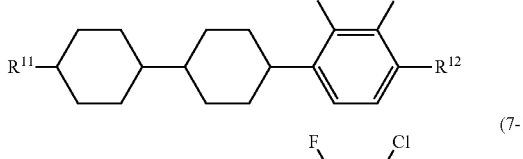
(7-13) 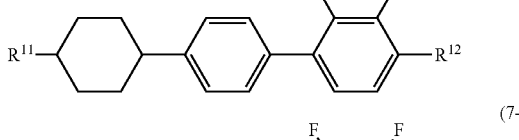
(7-14) 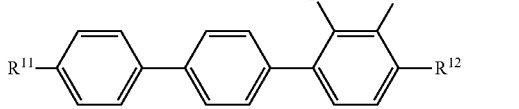
(7-15) 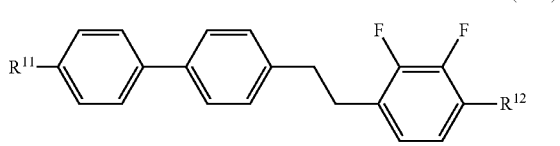
(8-1) 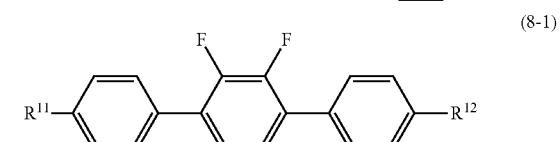
(9-1) 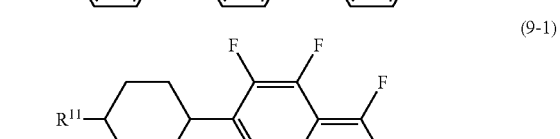
(9-2) 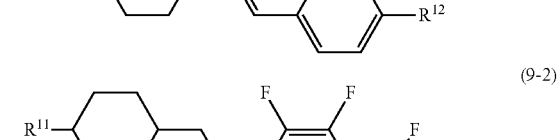
(9-3) 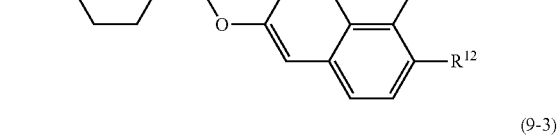
(10-1) 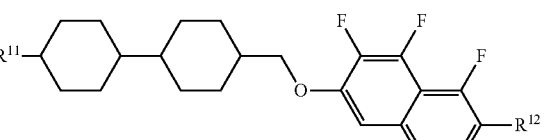
(10-2) 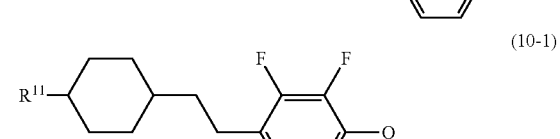
(10-3) 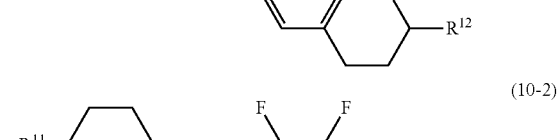
(10-4) 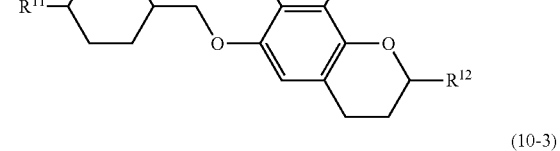

Formula 31
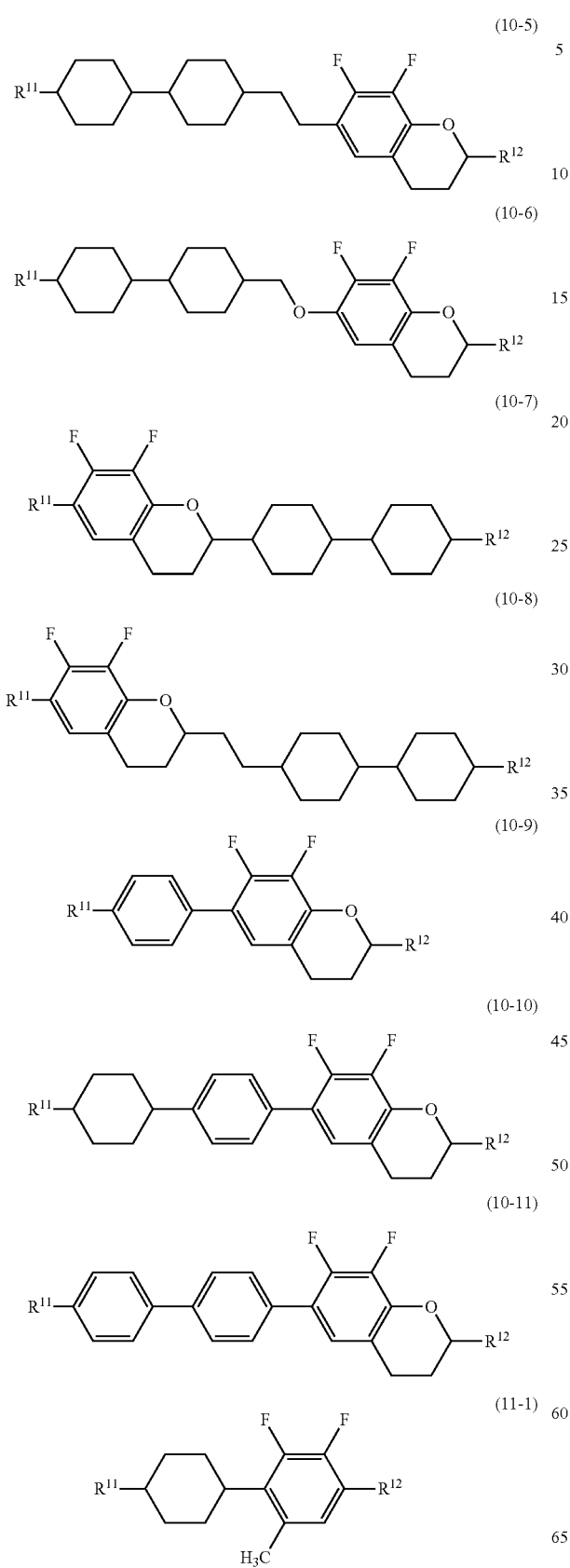
(10-5)
(10-6)
(10-7)
(10-8)
(10-9)
(10-10)
(10-11)
(11-1)
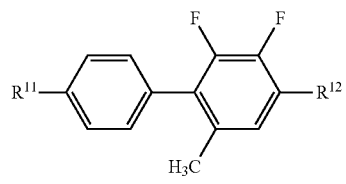
(11-2)
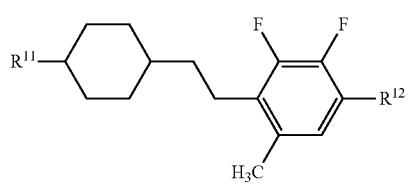
(11-3)
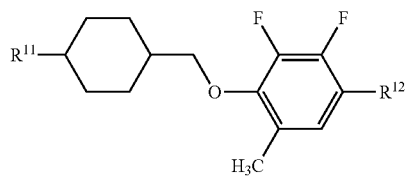
(11-4)
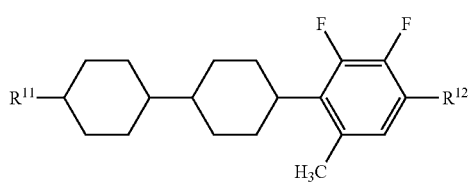
(11-5)
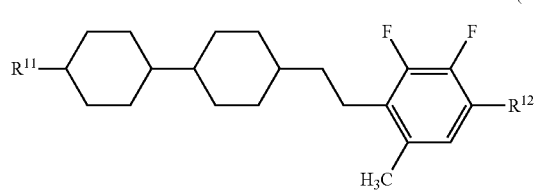
(11-6)
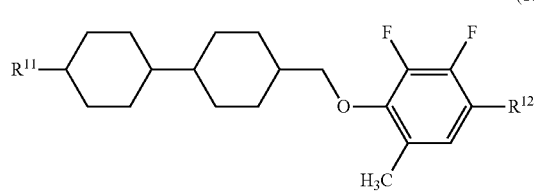
(11-7)
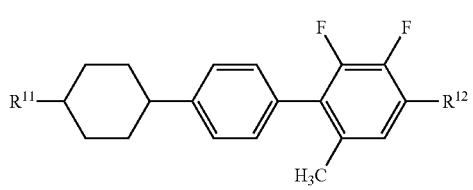
(11-8)
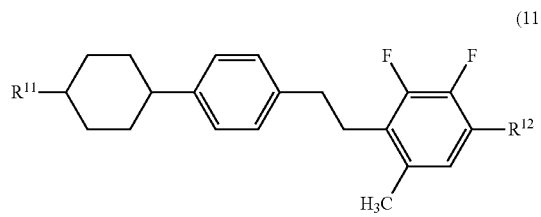
(11-9)

-continued (11-10)

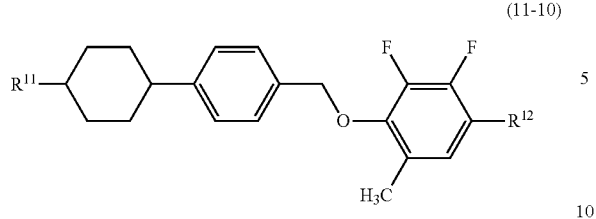

In the formulas, $R^{11}$ and $R^{12}$ are defined in a manner identical with the definitions described above.

The compounds of component D are mainly used for a liquid crystal composition having a negative dielectric anisotropy for use in the VA mode or the PSA mode. When the content thereof is increased, the threshold voltage of the composition decreases but the viscosity increases. Accordingly, the content is preferably minimized as long as requirements of the threshold voltage are satisfied. However, an absolute value of dielectric anisotropy is approximately 5, and therefore the content is preferably approximately 40% by weight or more to allow sufficient voltage driving.

Among types of component D, the compounds represented by formula (6) are a bicyclic compound and therefore effective mainly in adjusting the threshold voltage, adjusting the viscosity and adjusting the refractive index anisotropy. Moreover, the compounds represented by formulas (7) and (8) are a tricyclic compound, and therefore effective in increasing the clearing point, increasing a nematic phase range, decreasing the threshold voltage, increasing the refractive index anisotropy or the like. Moreover, compounds represented by formulas (9), (10) and (11) are effective in decreasing the threshold voltage.

Content of component D when preparing a composition for the VA mode or PSA mode is preferably in the range of approximately 40% by weight or more, further preferably, in the range of approximately 50 to approximately 95% by weight, based on the total weight of the liquid crystal composition. Moreover, when component D is mixed with the composition, an elastic constant can be controlled and a voltage-transmittance curve of the composition can be controlled. When component D is mixed with the composition having a positive dielectric anisotropy, the content is preferably approximately 30% by weight or less based on the total weight of the composition.

Suitable examples of compounds represented by formulas (12), (13) and (14) (component E) include compounds represented by formulas (12-1) to (12-11), (13-1) to (13-19) and (14-1) to (14-6).

Formula 32

(12-1)

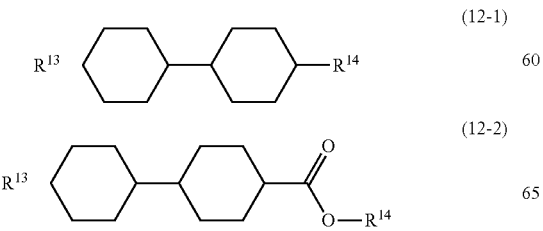

(12-2)

-continued (12-3)
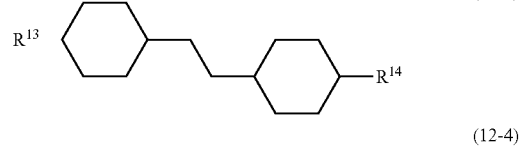

(12-4)
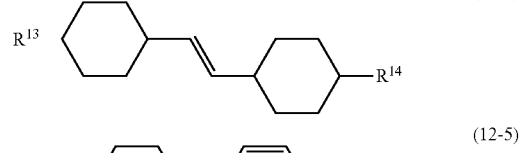

(12-5)
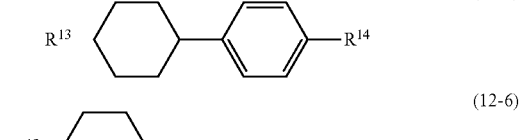

(12-6)
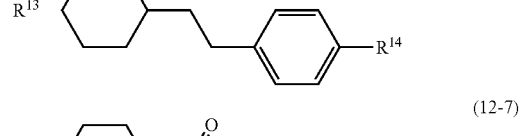

(12-7)
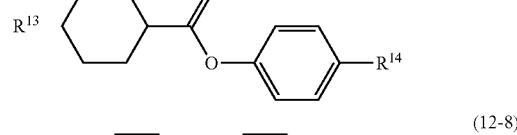

(12-8)
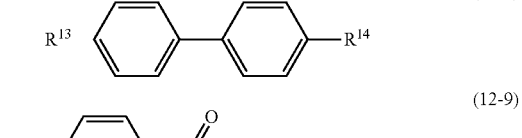

(12-9)
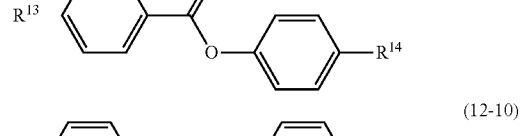

(12-10)
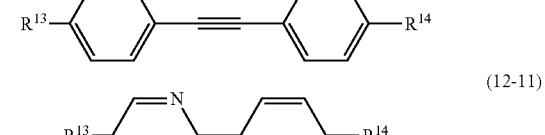

(12-11)

(13-1)
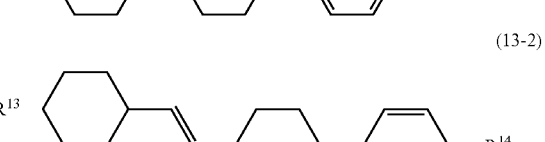

(13-2)
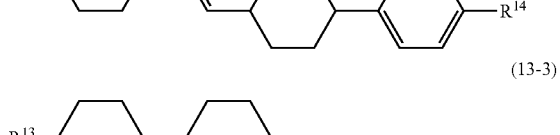

(13-3)

(13-4)

(13-5)
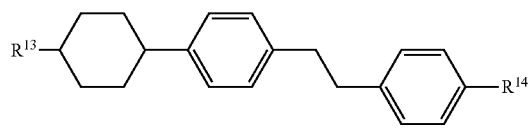
(13-6)
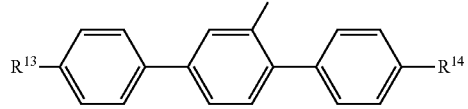
(13-7)
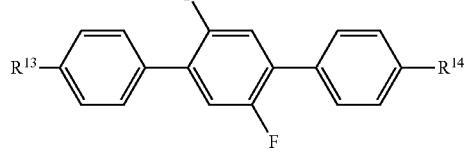
(13-8)
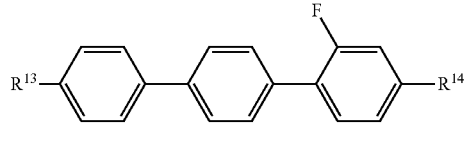
(13-9)
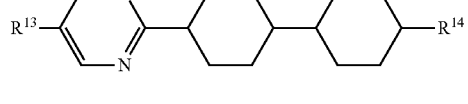
(13-10)
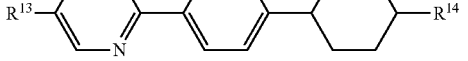
(13-11)
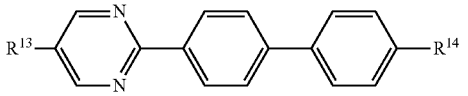
(13-12)
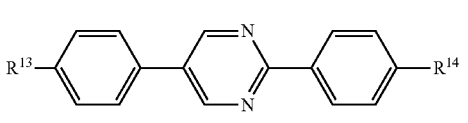
(13-13)
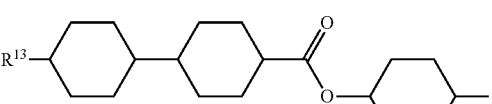
(13-14)
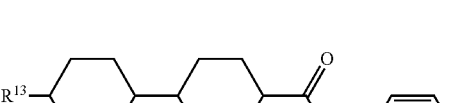
(13-15)
(13-16)
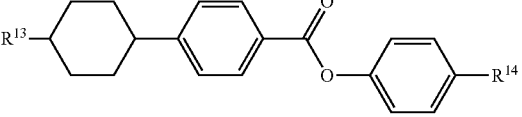
(13-17)
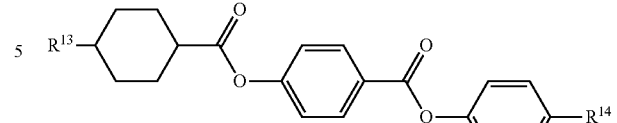
(13-18)
(13-19)
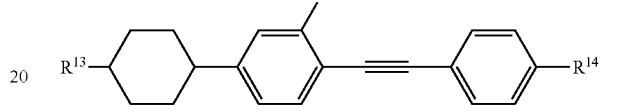
Formula 33
(14-1)
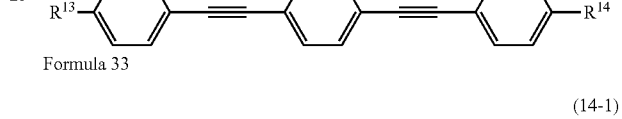
(14-2)
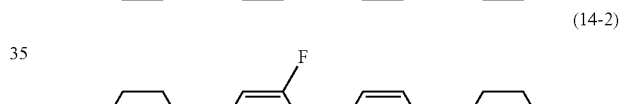
(14-3)
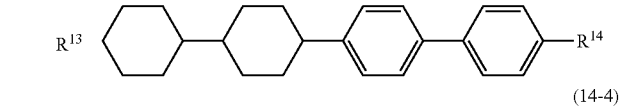
(14-4)
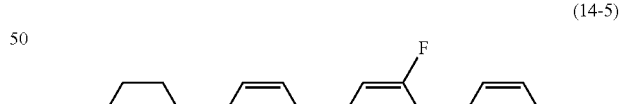
(14-5)
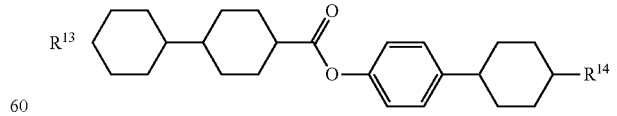
(14-6)
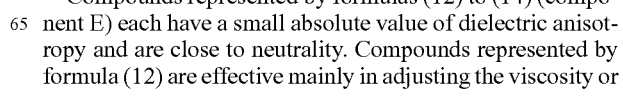
In the formulas, $R^{13}$ and $R^{14}$ are defined in a manner identical with the definitions described above.
Compounds represented by formulas (12) to (14) (component E) each have a small absolute value of dielectric anisotropy and are close to neutrality. Compounds represented by formula (12) are effective mainly in adjusting the viscosity or the refractive index anisotropy. Compounds represented by formulas (13) and (14) are effective in extending the temperature of the nematic phase, such as increasing the clearing point, or adjusting the refractive index anisotropy.

When content of the compound represented by component E is increased, the threshold voltage of the liquid crystal composition increases and the viscosity decreases. Accordingly, the content is desirably high as long as requirements of the threshold voltage of the liquid crystal composition are satisfied. When a liquid crystal composition for the TFT mode or the PSA mode is prepared, the content of component E is preferably approximately 30% by weight or more, further preferably, approximately 50% by weight or more, based on the total weight of the composition. When a liquid crystal composition for the TN mode, the STN mode or the PSA mode is prepared, the content of component E is preferably approximately 30% by weight or more, further preferably, approximately 40% by weight or more, based on the total weight of the composition.

The liquid crystal composition of the invention preferably contains at least one kind of compound (1) in a ratio of approximately 0.1% to approximately 99% by weight for developing excellent characteristics.

The liquid crystal composition of the invention is generally prepared according to a publicly known method such as dissolving necessary components with each other at a high temperature. Moreover, an additive well-known to those skilled in the art is added according to an application, and thus, for example, a liquid crystal composition containing the optically active compound, the polymerizable compound or the polymerization initiator, or a liquid crystal composition for a guest host (GH) mode in which a dye is added as described below can be prepared. The additive is ordinarily well known to those skilled in the art, and is described in literatures or the like in detail.

The liquid crystal composition of the invention may further contain at least one optically active compound in the liquid crystal composition. As the optically active compound, a publicly known chiral dopant can be added. The chiral dopant is effective in inducing a helical structure in liquid crystals to adjust a necessary twist angle and to prevent an inverted twist. Specific examples of the chiral dopants include the optically active compounds (Op-1) to (Op-13) below.

Formula 34

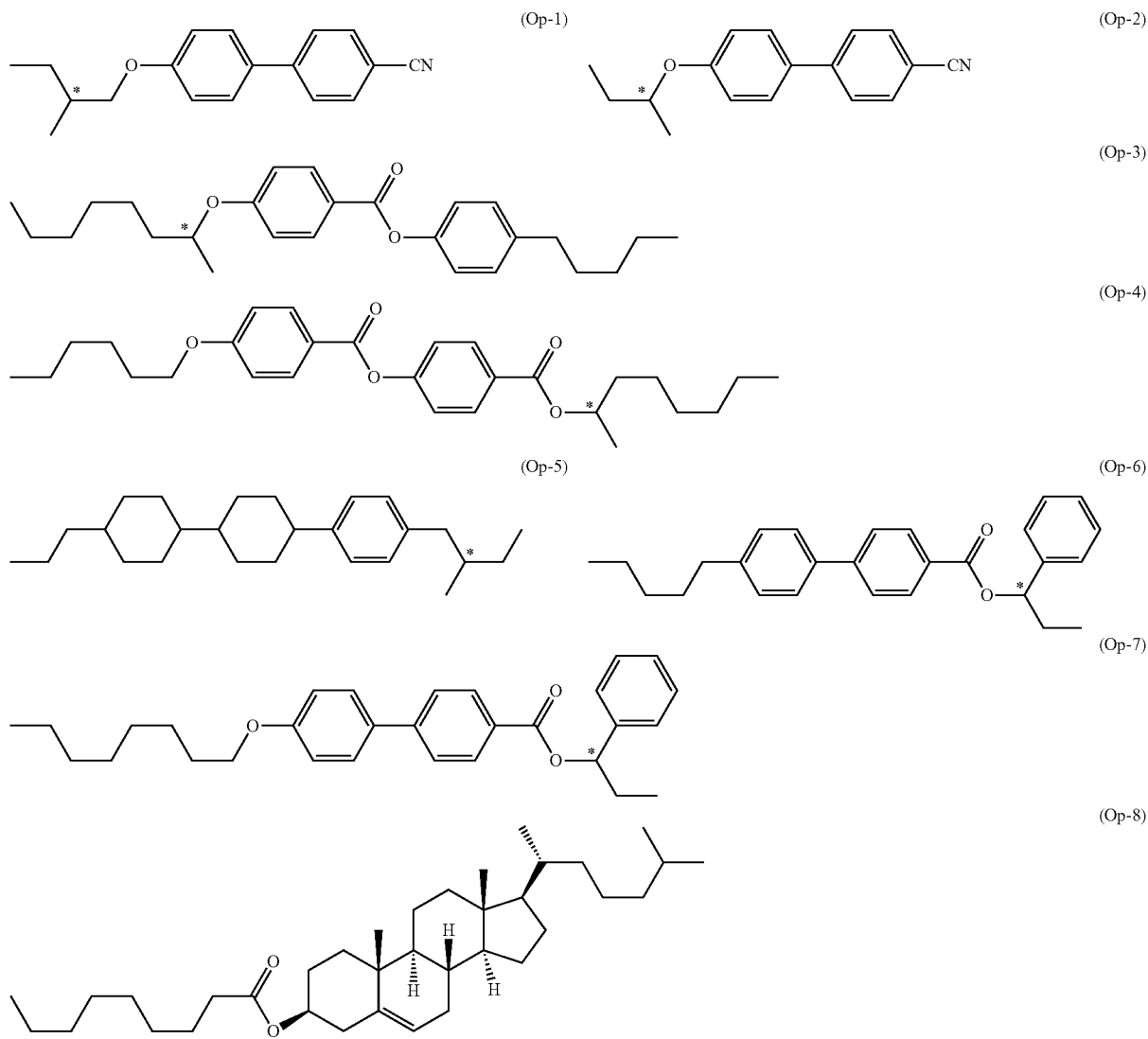

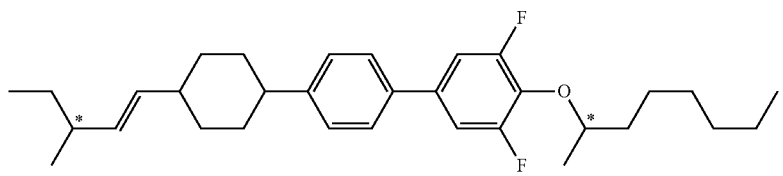
(Op-9)

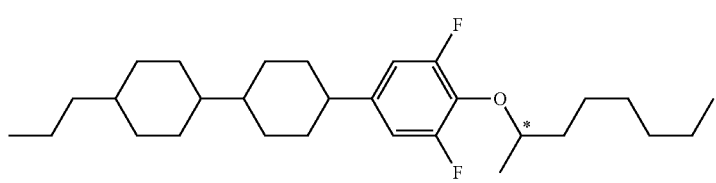
(Op-10)

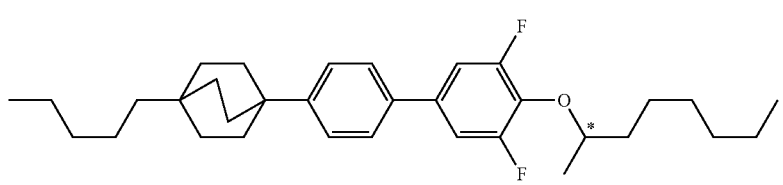
(Op-11)

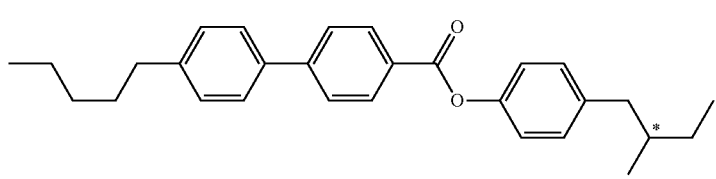
(Op-12)

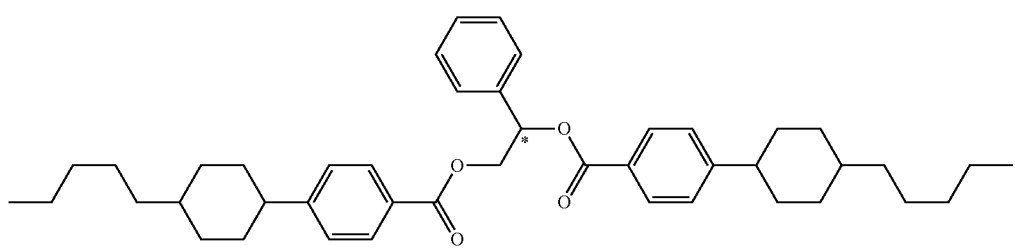
(Op-13)

The helical pitch of the liquid crystal composition according to the invention can be adjusted by addition of the optically active compound. The helical pitch is preferably adjusted into the range of approximately 40 micrometers to approximately 200 micrometers in a liquid crystal composition for the TFT mode and the TN mode. The helical pitch is preferably adjusted into the range of approximately 6 micrometers to approximately 20 micrometers in a liquid crystal composition for the STN mode. The helical pitch is preferably adjusted into the range of approximately 1.5 micrometers to approximately 4 micrometers in a liquid crystal composition for a bistable TN mode. Two or more optically active compounds may be added for the purpose of adjusting temperature dependence of the helical pitch.

The liquid crystal composition of the invention can be used for a GH mode by addition of a dichroic dye such as a merocyanine, stylyl, azo, azomethine, azoxy, quinophthalone, anthraquinone or tetrazine dye.

The liquid crystal composition of the invention can be used for NCAP prepared by microencapsulating nematic liquid crystals, and for a polymer distributed liquid crystal display device (PDLCD) prepared by forming a three-dimensional network polymer in liquid crystals, such as a polymer network liquid crystal display device (PNLCD), and also for an electrically controlled birefringence (ECB) mode or a DS mode.

The liquid crystal composition of the invention can be used as a liquid crystal composition for the polymer sustained alignment (PSA) mode by addition of a polymerizable compound. Examples of the polymerizable compound include compounds having a polymerizable group such as acrylate, methacrylate, vinyl, vinyloxy, propenylether, epoxy, vinylketone and oxetane. The polymerizable compound is preferably polymerized by irradiation with ultraviolet light or the like in the presence of a suitable initiator such as a photopolymerization initiator. Suitable conditions for polymerization, suitable types of the initiator and suitable amounts thereof are known to those skilled in the art and are described in literatures. For example, Irgacure 651 (registered trade name), Irgacure 184 (registered trade name) or Darocure 1173 (registered trade name) (Ciba Japan K. K.), each being a photopolymerization initiator, is suitable for radical polymerization.

Method for Preparing Liquid Crystal Composition

When a compound constituting each component in the liquid crystal composition according to the invention is a liquid, for example, the liquid crystal composition can be prepared by mixing each of the compounds. When a compound contains a solid, the liquid crystal composition can be prepared by mixing each of the compounds, converting each of the compounds into a liquid by heating and melting the compounds, and then shaking the compounds. Moreover, the liquid crystal composition of the invention can also be prepared according to other publicly known methods.

Characteristics of Liquid Crystal Composition

In the liquid crystal composition of the invention, the maximum temperature of the nematic phase can be adjusted to 70° C. or higher and the minimum temperature of the nematic phase can be adjusted to −20° C. or lower, and thus the temperature range of the nematic phase is wide. Accordingly, the liquid crystal display device including the liquid crystal composition can be used in a wide temperature range.

When the composition or the like is suitably adjusted in the liquid crystal composition of the present invention, the optical anisotropy can be adjusted to an arbitrary range, for example to the range of approximately 0.10 to approximately 0.13, or to the range of approximately 0.05 to approximately 0.18.

In the liquid crystal composition of the invention, a liquid crystal composition having dielectric anisotropy ordinarily in the range of can approximately −5.0 to approximately −2.0, preferably in the range of approximately −4.5 to approximately −2.5 can be obtained. The liquid crystal composition having the dielectric anisotropy in the range of approximately −4.5 to approximately −2.5 can be suitably used for a liquid crystal display device to be operated by means of the IPS, the VA mode or the PSA mode.

Liquid Crystal Display Device

The liquid crystal composition of the invention can be used not only for a liquid crystal display device having an operating mode such as the PC, TN, STN, OCB or PSA mode to be driven by means of an AM mode, but also for a liquid crystal display device having an operating mode such as the PC, TN, STN, OCB, VA or IPS mode to be driven by means of a passive matrix (PM) mode.

The liquid crystal display devices having the AM and PM modes can be applied to any of liquid crystal displays and so forth of a reflective type, a transmissive type or a transflective type.

Moreover, the liquid crystal composition of the invention can also be used for a dynamic scattering (DS) mode device using a liquid crystal composition prepared by adding a conducting agent, a nematic curvilinear aligned phase (NCAP) device prepared by microencapsulating the liquid crystal composition, or a polymer dispersed (PD) device having a three-dimensional network polymer formed in the liquid crystal composition, for example, a polymer network (PN) device.

Above all, the liquid crystal composition of the invention has the characteristics described above, and therefore can be suitably used for a liquid crystal display device utilizing the liquid crystal composition having a negative dielectric anisotropy to be driven by means of an operating mode such as the VA, IPS or PSA mode according to the AM mode, and particularly suitably for a liquid crystal display device to be driven by means of the VA mode according to the AM mode.

In addition, a direction of an electric field is perpendicular to a direction of a liquid crystal layer in a liquid crystal display device to be driven by means of the TN mode, the VA mode or the like. On the other hand, the direction of the electric field is parallel to the direction of the liquid crystal layer in a liquid crystal display device to be driven by means of the IPS mode or the like. A structure of the liquid crystal display device to be driven by means of the VA mode is reported by K. Ohmuro, S. Kataoka, T. Sasaki and Y. Koike, SID '97 Digest of Technical Papers, 28, 845 (1997), and a structure of the liquid crystal display device to be driven by means of the IPS mode is reported in WO 1991/10936 A (patent family: U.S. Pat. No. 5,576,867).

Examples of the compounds and the liquid crystal composition according to the invention will be described in detail in Examples described below. The compounds shown below can be prepared by methods similar to synthetic methods described in Examples: compounds (I-1-1-1-1) to (I-1-1-1-4), (I-1-1-2-1) to (I-1-1-2-4), (I-1-1-3-1) to (I-1-1-3-4), (I-1-1-4-1) to (I-1-1-4-5), (I-1-1-5-1) to (I-1-1-5-7), (I-1-1-6-1) to (I-1-1-6-4), (I-1-1-7-1) to (I-1-1-7-4), (I-1-1-8-1) to (I-1-1-8-4), (I-1-1-9-1) to (I-1-1-9-4), (I-1-1-10-1) to (I-1-1-10-4), (I-1-1-11-1) to (I-1-1-11-4), (I-1-1-12-1) to (I-1-1-12-4), (I-1-1-13-1) to (I-1-1-13-4), (I-1-1-14-1) to (I-1-1-14-4), (I-1-1-15-1) to (I-1-1-15-5), (I-1-1-16-1) to (I-1-1-16-6), (I-1-2-1-1) to (I-1-2-1-4), (I-1-2-2-1) to (I-1-2-2-8), (I-1-2-3-1) to (I-1-2-3-8), (I-1-2-4-1) to (I-1-2-4-8), (I-1-2-5-1) to (I-1-2-5-6), (I-1-2-6-1) to (I-1-2-6-6), (I-1-2-7-1) to (I-1-2-7-6), (I-1-2-8-1) to (I-1-2-8-8), (I-1-2-9-1) to (I-1-2-9-6), (I-1-2-10-1) to (I-1-2-10-6), (I-1-2-11-1) to (I-1-2-11-6), (I-1-2-12-1) to (I-1-2-12-6), (I-1-2-13-1) to (I-1-2-13-8), (I-1-2-14-1) to (I-1-2-14-6), (I-1-3-1-1) to (I-1-3-1-4), (I-1-3-2-1) to (I-1-1-8-4), (I-1-1-9-1) to (I-1-1-9-4), (I-1-3-2-1) to (I-1-3-2-6), (I-1-3-3-1) to (I-1-3-3-4), (I-1-3-4-1) to (I-1-3-4-4), (I-1-3-5-1) to (I-1-3-5-4), (I-1-3-6-1) to (I-1-3-6-4), (I-1-3-7-1) to (I-1-3-7-4), (I-1-3-8-1) to (I-1-3-8-4), (I-1-3-9-1) to (I-1-3-9-4), (I-1-3-10-1) to (I-1-3-10-4), (I-1-3-11-1) to (I-1-3-11-6), (I-1-3-12-1) to (I-1-3-12-6), (I-1-3-13-1) to (I-1-3-13-6), (I-1-3-14-1) to (I-1-3-14-6), (I-1-3-15-1) to (I-1-3-15-6), (I-1-3-16-1) to (I-1-3-16-6) and (I-1-3-17-1) to (I-1-3-17-4).

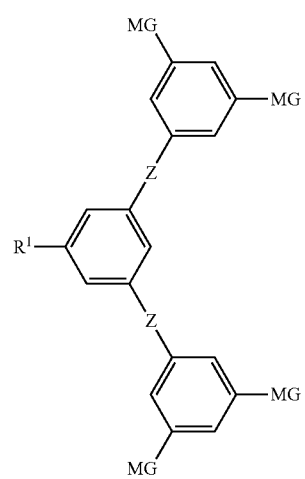

Formula 35

TABLE 1

| No. | R1 | Z | MG |
|---|---|---|---|
| I-1-1-1-1 | HO-CH2-CH2- | -O-CH2- | -O-(CH2)5-O-[cyclohexyl]-[3,4-difluorophenyl] |
| I-1-1-1-2 | CH3- | -O-CH2- | -O-(CH2)5-O-[cyclohexyl]-[3,4-difluorophenyl] |
| I-1-1-1-3 | HO-CH2-CH2- | -O-CH2- | -O-(CH2)5-O-[cyclohexyl]-[3-fluoro-4-(trifluoromethyl)phenyl] |
| I-1-1-1-4 | HO-(CH2)3- | -OCF2- | -O-(CH2)4-[cyclohexyl]-[2-fluoro-4-(trifluoromethyl)phenyl] |
| I-1-1-2-1 | HO-CH2-CH2- | -O-CH2- | -O-(CH2)5-[cyclohexyl]-[3,4,5-trifluorophenyl] |
| I-1-1-2-2 | HO-(CH2)3- | -C≡C- | -O-(CH2)5-O-[cyclohexyl]-[3,4,5-trifluorophenyl] |
| I-1-1-2-3 | CH3- | -C(=O)O- | -O-(CH2)4-[cyclohexyl]-[3,5-difluoro-4-(trifluoromethyl)phenyl] |
| I-1-1-2-4 | CH3-(CH2)4- | -OCF2- | CH3-CH2-CH2-CH=CH-[cyclohexyl]-[3,5-difluoro-4-(trifluoromethyl)phenyl] |
| I-1-1-3-1 | HO-CH2-CH2- | -O-CH2- | -O-(CH2)5-O-[phenyl]-[3,4-difluorophenyl] |
| I-1-1-3-2 | HO-(CH2)3- | -OCF2- | -O-(CH2)6-O-[phenyl]-[3,4-difluorophenyl] |

TABLE 1-continued

| No. | R1 | Z | MG |
|---|---|---|---|
| I-1-1-3-3 | HO-CH2CH2CH2CH2- | -O-CH2- | [structure: -O-(CH2)5-O-C6H4-C6H3(F)-CF3] |
| I-1-1-3-4 | CH3CH2CH2- | -C(F)=C(F)- | [structure: CH3(CH2)6-C6H4-C6H3(F)-OCF3] |

TABLE 2

| No. | R¹ | Z | MG |
|---|---|---|---|
| I-1-1-4-1 | HO-CH2CH2- | -O-CH2- | [structure: -O-(CH2)5-O-C6H4-C6H3(F)2] |
| I-1-1-4-2 | HO-CH2CH2CH2CH2- | -O-CH2- | [structure: -O-(CH2)5-O-C6H4-C6H2(F)3] |
| I-1-1-4-3 | CH3— | —C≡C— | [structure: CH3O-(CH2)4-O-C6H4-C6H2(F)3] |
| I-1-1-4-4 | HO-CH2CH2- | -O-CH2- | [structure: -O-(CH2)5-O-C6H4-C6H3(F)-CF3] |
| I-1-1-4-5 | HO-CH2CH2CH2CH2CH2- | -CF2-O- | [structure: CH3(CH2)6-O-C6H4-C(F)=C(F)-C6H2(F)2-CF3] |
| I-1-1-5-1 | HO-CH2CH2- | -O-CH2- | [structure: -O-(CH2)5-O-C6H3(F)-C6H2(F)3] |
| I-1-1-5-2 | CH3— | -O-CH2- | [structure: -O-(CH2)5-O-C6H3(F)-C6H2(F)3] |

TABLE 2-continued
| No. | R¹ | Z | MG |
|---|---|---|---|
| I-1-1-5-3 |  | 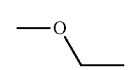 | 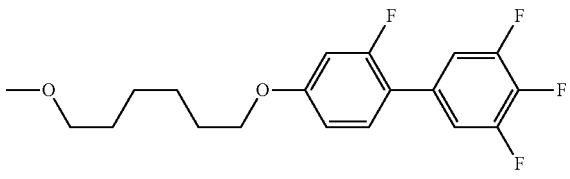 |
| I-1-1-5-4 |  |  | 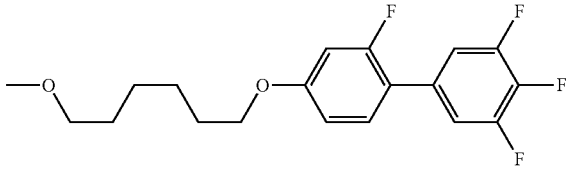 |
| I-1-1-5-5 | 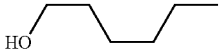 | 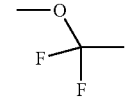 | 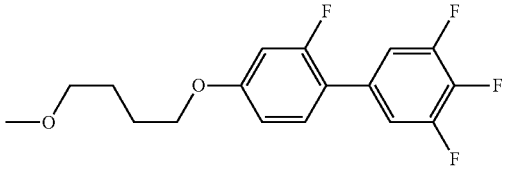 |
| I-1-1-5-6 |  | 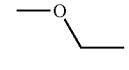 | 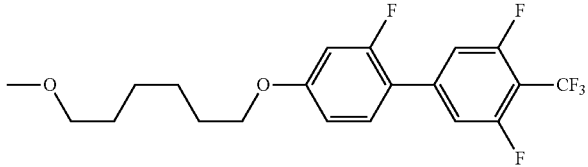 |
| I-1-1-5-7 | 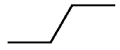 |  | 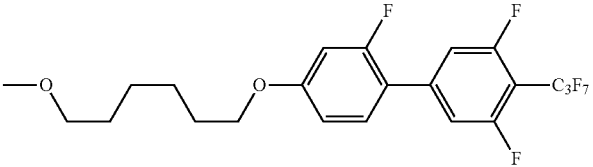 |
TABLE 3
| No. | R¹ | Z | MG |
|---|---|---|---|
| I-1-1-6-1 |  |  | 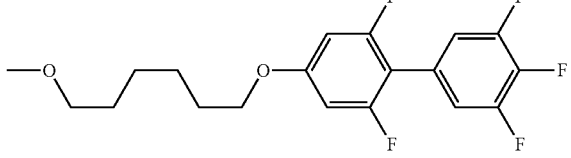 |
| I-1-1-6-2 |  | — | 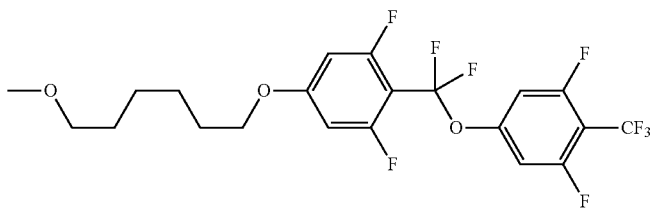 |

TABLE 3-continued
| No. | R¹ | Z | MG |
|---|---|---|---|
| I-1-1-6-3 | 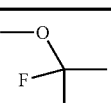 | 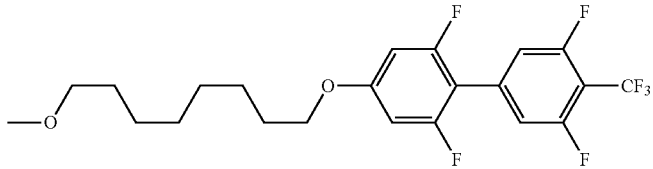 | 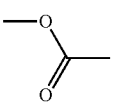 |
| I-1-1-6-4 | CH₃— | 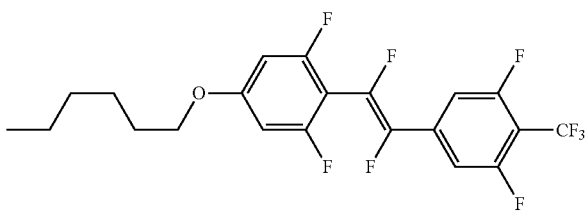 | 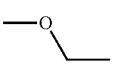 |
| I-1-1-7-1 | 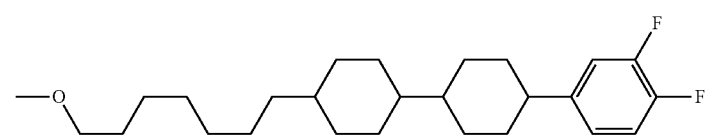 |  | 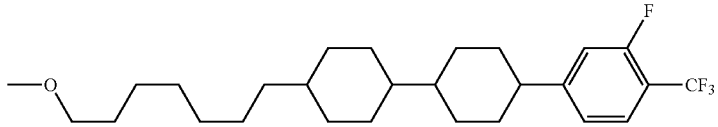 |
| I-1-1-7-2 | CH₃— | — | 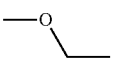 |
| I-1-1-7-3 | 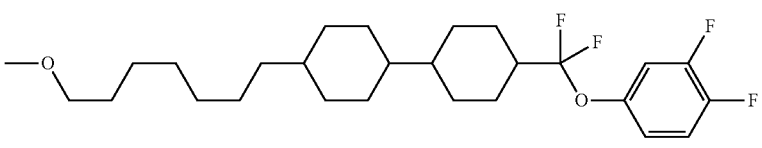 | 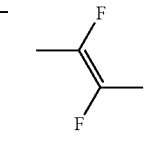 | 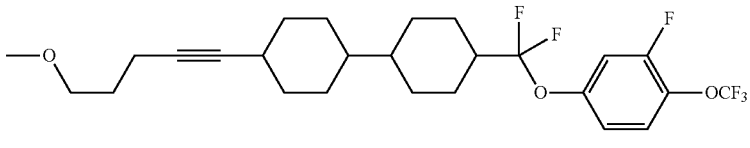 |
| I-1-1-7-4 | 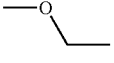 | 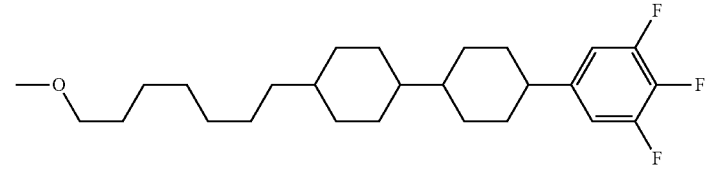 |  |
| I-1-1-8-1 | 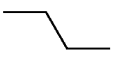 | 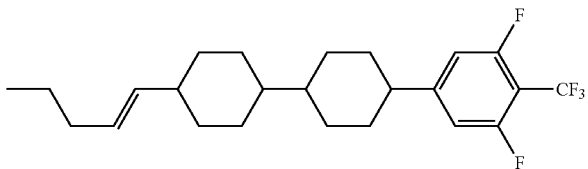 | 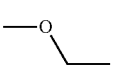 |
| I-1-1-8-2 | 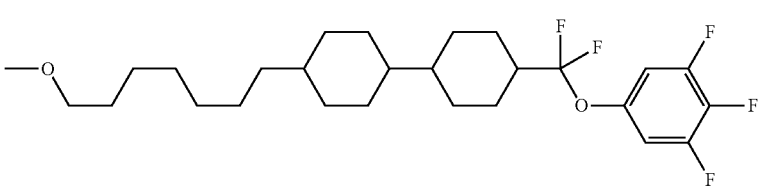 | | |
| I-1-1-8-3 | | | |

TABLE 3-continued
| No. | R¹ | Z | MG |
|---|---|---|---|
| I-1-1-8-4 |  |  | 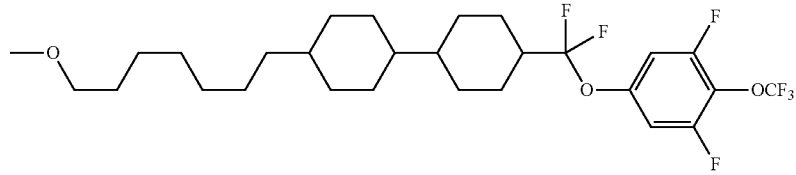 |
TABLE 4
| No. | R¹ | Z | MG |
|---|---|---|---|
| I-1-1-9-1 |  |  | 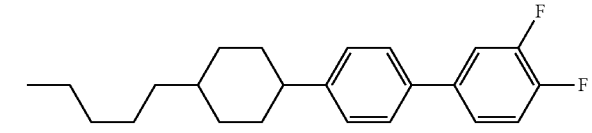 |
| I-1-1-9-2 |  |  | 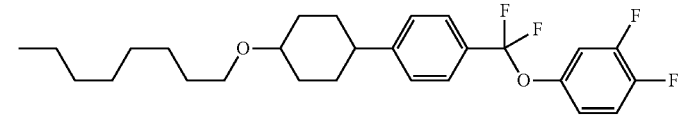 |
| I-1-1-9-3 |  |  | 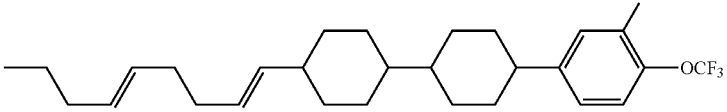 |
| I-1-1-9-4 |  |  | 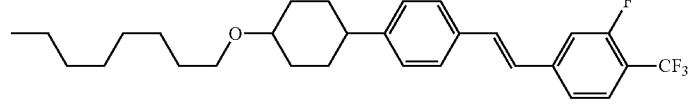 |
| I-1-1-10-1 |  |  | 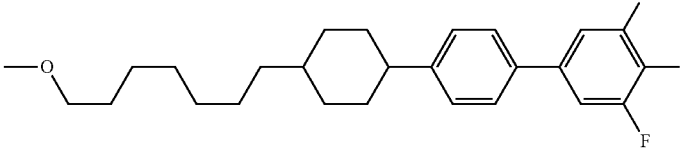 |
| I-1-1-10-2 |  |  | 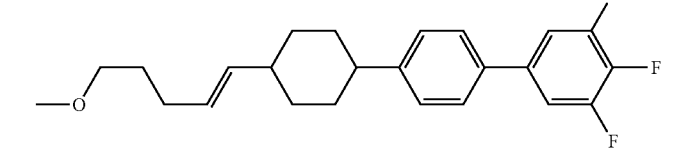 |
| I-1-1-10-3 |  |  | 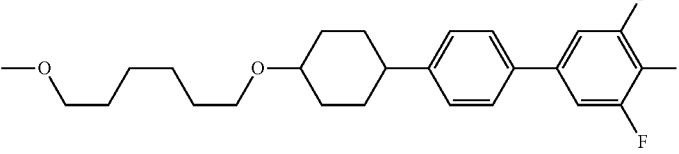 |
| I-1-1-10-4 |  |  | 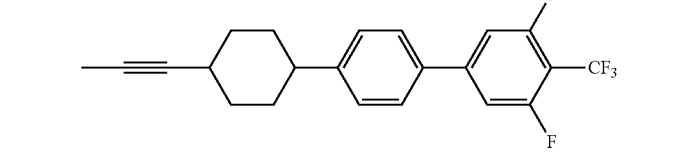 |

TABLE 4-continued

| No. | R¹ | Z | MG |
|---|---|---|---|
| I-1-1-11-1 | HOCH₂CH₂– | –OCH₂– | (structure) |
| I-1-1-11-2 | H₃C–C≡C– | –OCF₂– | (structure) |
| I-1-1-11-3 | CF₂=CF– | –OCH₂– | (structure) |
| I-1-1-11-4 | HO(CH₂)₃– | –C≡C– | (structure) |

TABLES 5

| No. | R¹ | Z | MG |
|---|---|---|---|
| I-1-1-12-1 | HOCH₂CH₂– | –OCH₂– | (structure) |
| I-1-1-12-2 | HO(CH₂)₃– | –CH₂CH₂– | (structure) |
| I-1-1-12-3 | CH₂=CH(CH₂)₄– | –OCF₂– | (structure) |

TABLES 5-continued

| No. | R¹ | Z | MG |
|---|---|---|---|
| I-1-1-12-4 | (pentyl) | –C≡C– | 4-pentylcyclohexyl-2,6-difluorophenyl-CF₂O-3,5-difluoro-4-(CF₃)phenyl |
| I-1-1-13-1 | HO-CH₂-CH₂- | –O-CH₂– | MeO-(CH₂)₅-O-biphenyl-3,4-difluorophenyl |
| I-1-1-13-2 | HO-(CH₂)₃- | –(CH₂)₃– | MeO-(CH₂)₅-O-biphenyl-CF₂O-3,4-difluorophenyl |
| I-1-1-13-3 | (pentyl) | –C≡C– | MeO-(CH₂)₄-O-biphenyl-3-fluoro-4-(CF₃)phenyl |
| I-1-1-13-4 | H₃C–C≡C– | –C(F)=C(F)– | hexyl-O-phenyl-CF₂O-biphenyl-3,4-difluoro |
| I-1-1-14-1 | HO-CH₂-CH₂- | –O-CH₂– | MeO-(CH₂)₅-O-biphenyl-3,4,5-trifluorophenyl |
| I-1-1-14-2 | HO-CH₂-CH₂- | –O-CH₂– | MeO-(CH₂)₅-O-biphenyl-CF₂-O-3,4,5-trifluorophenyl |
| I-1-1-14-3 | HO-(CH₂)₃- | –(CH₂)₃– | MeO-(CH₂)₄-O-biphenyl-3,5-difluoro-4-OCF₃-phenyl |
| I-1-1-14-4 | CH₃– | –O-C(F)₂– | hexyl-O-phenyl-C(F)=C(F)-biphenyl-3,5-difluoro-4-CF₃ |

TABLE 6

| No. | R¹ | Z | MG |
|---|---|---|---|
| I-1-1-15-1 | HO‐CH₂CH₂‐ | ‐O‐CH₂‐ | (structure) |
| I-1-1-15-2 | HO‐(CH₂)₃‐ | ‐O‐CH₂‐ | (structure) |
| I-1-1-15-3 | C₄H₉‐ | ‐C≡C‐ | (structure) |
| I-1-1-15-4 | HO‐CH₂CH₂‐ | ‐O‐CH₂‐ | (structure) |
| I-1-1-15-5 | HO‐(CH₂)₅‐ | ‐(CH₂)₃‐ | (structure) |
| I-1-1-16-1 | HO‐CH₂CH₂‐ | ‐O‐CH₂‐ | (structure) |
| I-1-1-16-2 | CH₃‐ | ‐O‐CH₂‐ | (structure) |
| I-1-1-16-3 | HO‐(CH₂)₃‐ | ‐(CH₂)₂‐ | (structure) |

TABLE 6-continued
| No. | R¹ | Z | MG |
|---|---|---|---|
| I-1-1-16-4 | 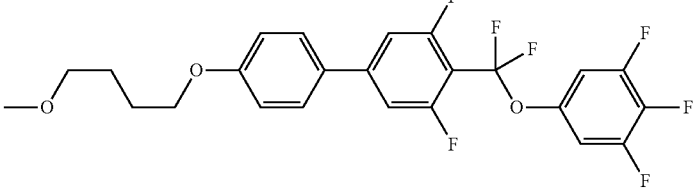 | 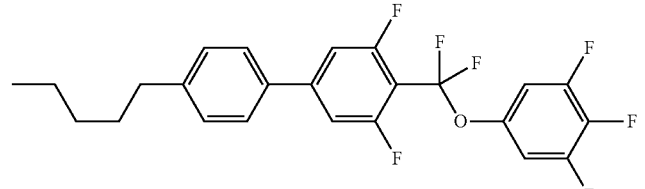 | 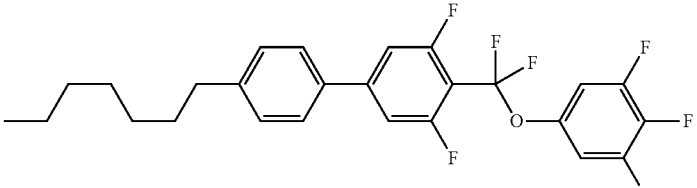 |
| I-1-1-16-5 | 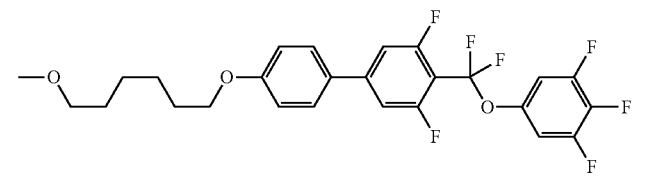 | 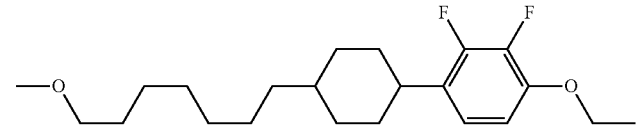 | 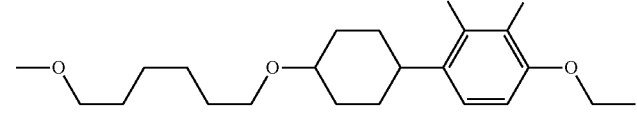 |
| I-1-1-16-6 | 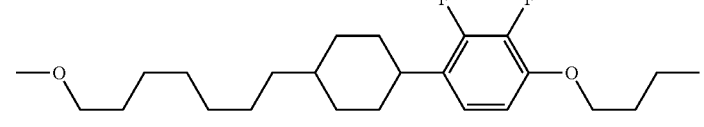 | 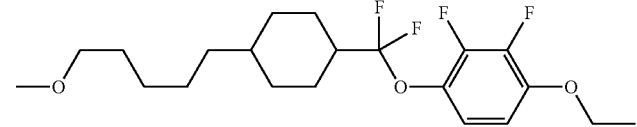 | |
| I-1-1-16-7 | | | |
TABLE 7
| No. | R¹ | Z | MG |
|---|---|---|---|
| I-1-2-1-1 | | | |
| I-1-2-1-2 | CH₃— | | |
| I-1-2-1-3 | | | |
| I-1-2-1-4 | | | |

TABLE 7-continued

| No. | R¹ | Z | MG |
|---|---|---|---|
| I-1-2-2-1 | HO-CH₂-CH₂- | -O-CH₂- | (structure) |
| I-1-2-2-2 | HO-(CH₂)₃- | -O-CH₂- | (structure) |
| I-1-2-2-3 | HO-CH₂-CH₂- | -CH₂-CH₂- | (structure) |
| I-1-2-2-4 | HO-CH₂-CH₂- | -O-CH₂- | (structure) |
| I-1-2-2-5 | CH₃— | -C≡C- | (structure) |
| I-1-2-2-6 | HO-(CH₂)₃- | -CF=CF- | (structure) |
| I-1-2-2-7 | CH₃-(CH₂)₃- | -CF₂-O- | (structure) |
| I-1-2-2-8 | HO-CH₂-CH₂- | -CH₂-CH₂- | (structure) |

TABLE 8

| No. | R¹ | Z | MG |
|---|---|---|---|
| I-1-2-3-1 | HO-CH₂-CH₂- | -O-CH₂- | (structure) |
| I-1-2-3-2 | CH₃— | -O-CH₂- | (structure) |

TABLE 8-continued
| No. | R¹ | Z | MG |
|---|---|---|---|
| I-1-2-3-3 |  | 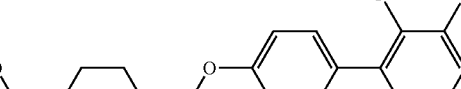 |  |
| I-1-2-3-4 | 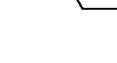 | 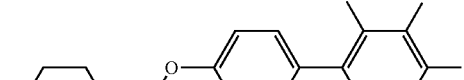 | 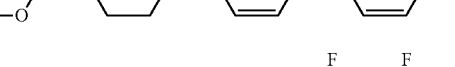 |
| I-1-2-3-5 |  | 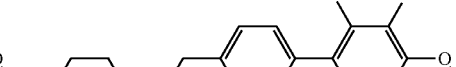 | 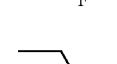 |
| I-1-2-3-6 | 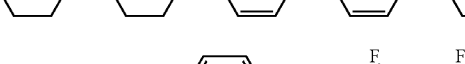 | 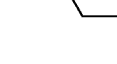 | 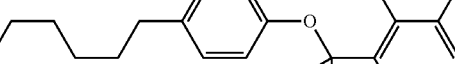 |
| I-1-2-3-7 |  |  |  |
| I-1-2-3-8 | 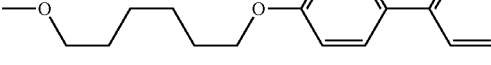 | | |
| I-1-2-4-1 | | | |
| I-1-2-4-2 | CH₃— | | |
| I-1-2-4-3 | | | |
| I-1-2-4-4 | | | |
| I-1-2-4-5 | | | |

TABLE 8-continued
| No. | R¹ | Z | MG |
|---|---|---|---|
| I-1-2-4-6 |  | 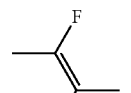 | 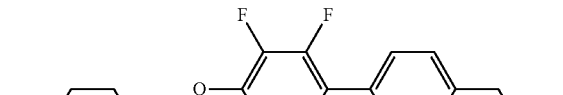 |
| I-1-2-4-7 | | | |
| I-1-2-4-8 | | | |
TABLE 9
| No. | R¹ | Z | MG |
|---|---|---|---|
| I-1-2-5-1 | | | |
| I-1-2-5-2 | | | |
| I-1-2-5-3 | | | |
| I-1-2-5-4 | | | |
| I-1-2-5-5 | | | |
| I-1-2-5-6 | | | |
| I-1-2-6-1 | | | |
| I-1-2-6-2 | | | |

TABLE 9-continued

| No. | R¹ | Z | MG |
|---|---|---|---|
| I-1-2-6-3 | (butyl) | -O-CF₂- | structure |
| I-1-2-6-4 | HO-propyl | -O-CH₂- | structure |
| I-1-2-6-5 | pentenyl | -CH=CH- | structure |
| I-1-2-6-6 | CH₃- | -O-CH₂- | structure |

TABLE 10

| No. | R¹ | Z | MG |
|---|---|---|---|
| I-1-2-7-1 | HO-butyl | -O-CH₂- | structure |
| I-1-2-7-2 | CH₃- | -C≡C- | structure |
| I-1-2-7-3 | hexyl | -CF=CF- | structure |
| I-1-2-7-4 | HO-pentyl | -O-CF₂- | structure |
| I-1-2-7-5 | HO-propyl | -CH=CH- | structure |
| I-1-2-7-6 | H₃C-C≡C- | -O-C(=O)- | structure |
| I-1-2-8-1 | HO-ethyl | -O-CH₂- | structure |

TABLE 10-continued

| No. | R¹ | Z | MG |
|---|---|---|---|
| I-1-2-8-2 | (HO-butyl) | (propyl) | (structure) |
| I-1-2-8-3 | (hexenyl) | (propyl) | (structure) |
| I-1-2-8-4 | (butenyl) | (OCF₂-) | (structure) |
| I-1-2-8-5 | (H₃C-butynyl) | (propyl) | (structure) |
| I-1-2-8-6 | CH₃— | (CF=CF-) | (structure) |
| I-1-2-8-7 | (HO-butyl) | (propyl) | (structure) |
| I-1-2-8-8 | (HO-pentyl) | (OCF₂-) | (structure) |

TABLE 11

| No. | R¹ | Z | MG |
|---|---|---|---|
| I-1-2-9-1 | (HO-propyl) | —O— (ethyl) | (structure) |
| I-1-2-9-2 | (HO-butyl) | (propyl) | (structure) |
| I-1-2-9-3 | CH₃— | —O— (ethyl) | (structure) |
| I-1-2-9-4 | (HO-propyl) | (propyl) | (structure) |

TABLE 11-continued

| No. | R¹ | Z | MG |
|---|---|---|---|
| I-1-2-9-5 | (2-pentenyl) | (ethynyl) | (structure) |
| I-1-2-9-6 | (pentyl) | (OCF₂-) | (structure) |
| I-1-2-10-1 | HO-(butyl) | -O-ethyl | (structure) |
| I-1-2-10-2 | HO-ethyl | -O-ethyl | (structure) |
| I-1-2-10-3 | HO-(butyl) | (butyl) | (structure) |
| I-1-2-10-4 | HO-propyl | CF=CF- | (structure) |
| I-1-2-10-5 | (pentyl) | -OCF₂- | (structure) |
| I-1-2-10-6 | H₃C-C≡C- | -C≡C- | (structure) |

TABLE 12

| No. | R¹ | Z | MG |
|---|---|---|---|
| I-1-2-11-1 | HO-ethyl | -O-ethyl | (structure) |
| I-1-2-11-2 | HO-(butyl) | (butyl) | (structure) |
| I-1-2-11-3 | HO-(butyl) | (butyl) | (structure) |

TABLE 12-continued
| No. | R¹ | Z | MG |
|---|---|---|---|
| I-1-2-11-4 |  | 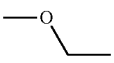 | 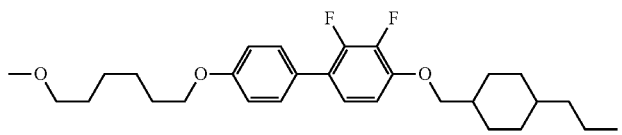 |
| I-1-2-11-5 | 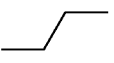 | 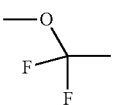 | 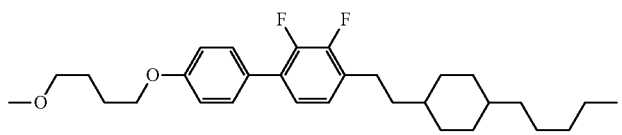 |
| I-1-2-11-6 |  | 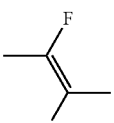 | 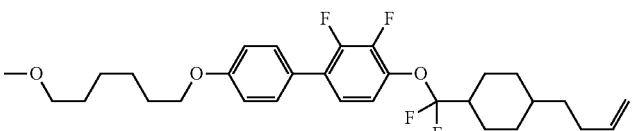 |
| I-1-2-12-1 |  | 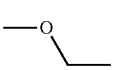 | 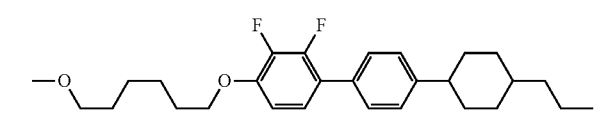 |
| I-1-2-12-2 |  | 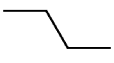 | 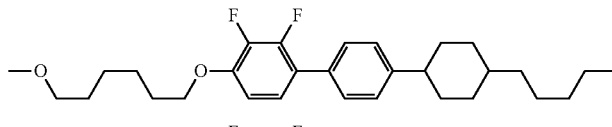 |
| I-1-2-12-3 | 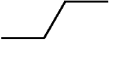 | 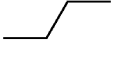 | 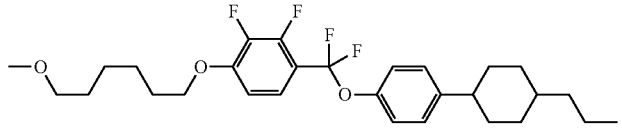 |
| I-1-2-12-4 | CH₃— |  |  |
| I-1-2-12-5 | 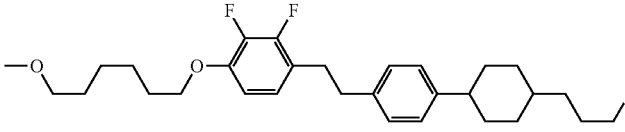 | 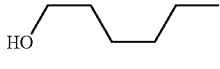 | 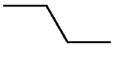 |
| I-1-2-12-6 | 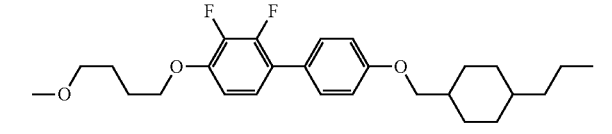 |  | 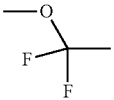 |
TABLE 13
| No. | R¹ | Z | MG |
|---|---|---|---|
| I-1-2-13-1 | 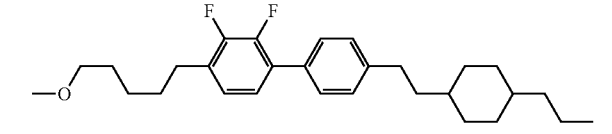 |  |  |
| I-1-2-13-2 | 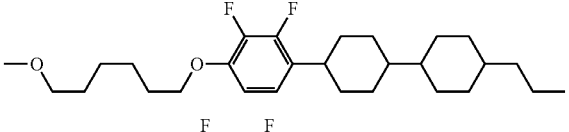 | 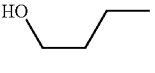 |  |

TABLE 13-continued

| No. | R¹ | Z | MG |
|---|---|---|---|
| I-1-2-13-3 | HO-ethyl | butyl | [structure with difluorobenzene, two O linkages, cyclohexyl-cyclohexyl-propyl] |
| I-1-2-13-4 | HO-butyl | ethynyl | [structure with difluorobenzene, two O linkages, cyclohexyl-cyclohexyl-propyl] |
| I-1-2-13-5 | HO-hexyl | OCF₂ | [structure with difluorobenzene, cyclohexyl, CH=CH, cyclohexyl-propyl] |
| I-1-2-13-6 | HO-ethyl | OCH₃ | [structure with difluorobenzene, O, cyclohexyl, CH=CH, cyclohexyl-propyl] |
| I-1-2-13-7 | H₃C-C≡C-ethyl | OCH₃ | [structure with difluorobenzene, O, cyclohexyl, O-CH₂, cyclohexyl-propyl] |
| I-1-2-13-8 | propyl | vinyl | [structure with difluorobenzene, cyclohexyl, CH₂CH₂, cyclohexyl-vinyl] |
| I-1-2-14-1 | propyl | OCF₂ | [structure with difluorobenzene, O, cyclohexyl, cyclohexyl-propyl] |
| I-1-2-14-2 | hexyl | OCF₂O | [structure with difluorobenzene, O, cyclohexyl, cyclohexyl-propyl] |
| I-1-2-14-3 | HO-hexyl | ethynyl | [structure with difluorobenzene, two OCH₂ linkages, hexyl-cyclohexyl and cyclohexyl-propyl] |
| I-1-2-14-4 | octenyl | CF=CF | [structure with difluorobenzene, two linkages, cyclohexyl-CH₂ and cyclohexyl-butyl] |
| I-1-2-14-5 | H₃C-C≡C | butyl | [structure with difluorobenzene, O, cyclohexyl, O-CH₂, cyclohexyl-butyl] |

TABLE 13-continued

| No. | R¹ | Z | MG |
|---|---|---|---|
| I-1-2-14-6 | (structure) | (structure) | (structure) |

TABLE 14

| No. | R¹ | Z | MG |
|---|---|---|---|
| I-1-3-1-1 | (structure) | (structure) | (structure) |
| I-1-3-1-2 | (structure) | (structure) | (structure) |
| I-1-3-1-3 | (structure) | (structure) | (structure) |
| I-1-3-1-4 | (structure) | (structure) | (structure) |
| I-1-3-2-1 | (structure) | (structure) | (structure) |
| I-1-3-2-2 | (structure) | (structure) | (structure) |
| I-1-3-2-3 | (structure) | (structure) | (structure) |
| I-1-3-2-4 | (structure) | (structure) | (structure) |
| I-1-3-2-5 | (structure) | (structure) | (structure) |
| I-1-3-2-6 | (structure) | (structure) | (structure) |
| I-1-3-3-1 | (structure) | (structure) | (structure) |

TABLE 14-continued

| No. | R¹ | Z | MG |
|---|---|---|---|
| I-1-3-3-2 | (pentyl) | — | (methoxy-pentyloxy-biphenyl-ethoxy) |
| I-1-3-3-3 | HO-(butyl) | -O-(ethyl) | (methoxy-propyloxy-biphenyl-propyl) |
| I-1-3-3-4 | (propyl) | (ethoxy) | (ethynyl-phenyl-CF₂-O-phenyl-methyl) |

TABLE 15

| No. | R¹ | Z | MG |
|---|---|---|---|
| I-1-3-4-1 | HO-(ethyl) | -O-(ethyl) | (methoxy-pentyloxy-(2-F-biphenyl)-propyl) |
| I-1-3-4-2 | HO-(butyl) | (propyl) | (methoxy-pentyloxy-(2-F-biphenyl)-methyl) |
| I-1-3-4-3 | HO-(hexyl) | (CF=CF) | (methoxy-propyloxy-(2-F-biphenyl)-ethyl) |
| I-1-3-4-4 | (butyl) | -O-CF₃ | (methoxy-pentyloxy-(3-F-phenyl)-ethynyl-phenyl-butyl) |
| I-1-3-5-1 | HO-(ethyl) | -O-(ethyl) | (methoxy-pentyloxy-(2-F-biphenyl)-propyl) |
| I-1-3-5-2 | HO-(butyl) | (propyl) | (methoxy-pentyloxy-(2-F-biphenyl)-methyl) |
| I-1-3-5-3 | HO-(propyl) | (CF=CF) | (methoxy-propyloxy-(2-F-biphenyl)-butyl) |

TABLE 15-continued

| No. | R¹ | Z | MG |
|---|---|---|---|
| I-1-3-5-4 | | | |
| I-1-3-6-1 | | | |
| I-1-3-6-2 | | | |
| I-1-3-6-3 | | | |
| I-1-3-6-4 | | | |
| I-1-3-7-1 | | | |
| I-1-3-7-2 | | | |
| I-1-3-7-3 | | | |
| I-1-3-7-4 | | | |

TABLE 16

| No. | R¹ | Z | MG |
|---|---|---|---|
| I-1-3-8-1 | | | |
| I-1-3-8-2 | | | |
| I-1-3-8-3 | | | |

TABLE 16-continued

| No. | R¹ | Z | MG |
|---|---|---|---|
| I-1-3-8-4 | | | |
| I-1-3-9-1 | | | |
| I-1-3-9-2 | | | |
| I-1-3-9-3 | | | |
| I-1-3-9-4 | | | |
| I-1-3-10-1 | | | |
| I-1-3-10-2 | | | |
| I-1-3-10-3 | | | |
| I-1-3-10-4 | | | |

TABLE 17

| No. | R¹ | Z | MG |
|---|---|---|---|
| I-1-3-11-1 | | | |
| I-1-3-11-2 | | | |

TABLE 17-continued

| No. | R¹ | Z | MG |
|---|---|---|---|
| I-1-3-11-3 | butyl | OCF₂– | (structure) |
| I-1-3-11-4 | HO-butyl | –O– | (structure) |
| I-1-3-11-5 | H₃C–C≡C– | — | (structure) |
| I-1-3-11-6 | HO-pentyl | –C≡C– | (structure) |
| I-1-3-12-1 | HO-ethyl | –O– | (structure) |
| I-1-3-12-2 | CH₃– | butyl | (structure) |
| I-1-3-12-3 | pentyl | — | (structure) |
| I-1-3-12-4 | HO-butyl | –O– | (structure) |
| I-1-3-12-5 | pentyl | –CF=CF– | (structure) |
| I-1-3-12-6 | butyl | –OCF₂– | (structure) |

TABLE 18

| No. | R¹ | Z | MG |
|---|---|---|---|
| I-1-3-13-1 | HO-ethyl | –O– | (structure) |

TABLE 18-continued

| No. | R¹ | Z | MG |
|---|---|---|---|
| I-1-3-13-2 | (HO-butyl) | (2,3-difluoro-2-butenyl) | (−O−propyl−O−phenyl−phenyl−cyclohexyl−pentyl) |
| I-1-3-13-3 | (HO-ethyl) | (−O−ethyl) | (−O−pentyl−O−phenyl−phenyl−cyclohexyl−vinyl) |
| I-1-3-13-4 | (hexyl) | (−O−CF₂−methyl) | (−O−propyl−O−phenyl−phenyl−cyclohexyl−propenyl) |
| I-1-3-13-5 | (butyl) | (butyl) | (−O−pentyl−O−phenyl−phenyl−ethyl−cyclohexyl−CH=CF₂) |
| I-1-3-13-6 | (H₃C−C≡C−) | — | (−O−pentyl−O−phenyl−phenyl−O−CH₂−cyclohexyl−ethyl−F) |
| I-1-3-14-1 | (HO-ethyl) | (−O−ethyl) | (−O−pentyl−O−(2-F-phenyl)−phenyl−cyclohexyl−butyl) |
| I-1-3-14-2 | CH₃− | (butyl) | (−O−butyl−O−(2-F-phenyl)−phenyl−cyclohexyl−propyl) |
| I-1-3-14-3 | (hexyl) | (−O−CF₂−methyl) | (−O−pentyl−O−(2-F-phenyl)−phenyl−cyclohexyl−propenyl−F) |
| I-1-3-14-4 | (HO-butyl) | (−O−ethyl) | (−O−butyl−O−(2-F-phenyl)−phenyl−cyclohexyl−vinyl) |
| I-1-3-14-5 | (propyl) | — | (−O−pentyl−O−(2-F-phenyl)−phenyl−ethyl−cyclohexyl−ethyl) |
| I-1-3-14-6 | (H₃C−C≡C−CH₂CH₂−) | (−C≡C−methyl) | (−O−pentyl−O−(2-F-phenyl)−ethyl−phenyl−cyclohexyl−allyl) |

TABLE 19

| No. | R¹ | Z | MG |
|---|---|---|---|
| I-1-3-15-1 | | | |
| I-1-3-15-2 | | | |
| I-1-3-15-3 | | | |
| I-1-3-15-4 | | | |
| I-1-3-15-5 | | | |
| I-1-3-15-6 | | | |
| I-1-3-16-1 | | | |
| I-1-3-16-2 | | | |
| I-1-3-16-3 | | | |
| I-1-3-16-4 | | | |
| I-1-3-16-5 | | | |
| I-1-3-16-6 | | | |
| I-1-3-17-1 | | | |
| I-1-3-17-2 | | | |
| I-1-3-17-3 | | | |

TABLE 19-continued

| No. | R¹ | Z | MG |
|---|---|---|---|
| I-1-3-17-4 |  |  |  |

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

The following examples are for illustrative purposes only and are not intended, nor should they be interpreted to, limit the scope of the invention.

EXAMPLES

Hereinafter, the invention will be explained in greater detail. However, the invention is not limited by the Examples. Unless otherwise noted, a unit "%" is expressed in terms of "% by weight."

Examples 1 to 13, Comparative Examples 1 and 2

Compound (1) was manufactured and evaluated in Examples 1 to 7. In Examples 8 to 13, liquid crystal compositions containing compound (1) in Examples 1 to 7 were manufactured and evaluated. In Comparative Example 1, a comparative compound was manufactured and evaluated. In Comparative Example 2, a liquid crystal composition containing the comparative compound was manufactured and evaluated.

¹H-NMR Analysis of Compound (1)

Compound (1) obtained was identified by using spectrograms or the like obtained by ¹H-NMR analysis.

As a measuring apparatus, DRX-500 (made by Bruker BioSpin Corporation) was used. Samples prepared in Examples and so forth were dissolved in a deuterated solvent such as $CDCl_3$ in which the samples were soluble, and measurement was carried out under the conditions of room temperature, thirty-two times of accumulation and 500 MHz. In the explanation of nuclear magnetic resonance spectra obtained, symbols s, d, t, q, quin, sex, m and br stand for a singlet, a doublet, a triplet, a quartet, a quintet, a sextet, a multiplet and being broad, respectively. Tetramethylsilane (TMS) was used as a reference material for a zero point of chemical shifts (δ values).

Liquid Crystal Composition Containing Compound (1)

Liquid crystal compositions containing compound (1) obtained in Examples 1 to 7 were manufactured. Hereinafter, all components other than compound (1) are referred to as "base liquid crystal." A mixture described below was used as the base liquid crystal.

Base Liquid Crystal BM-1

Formula 36

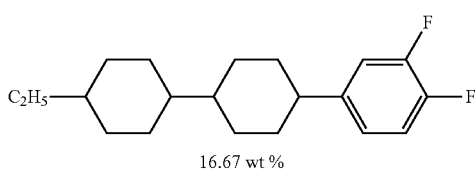

16.67 wt %

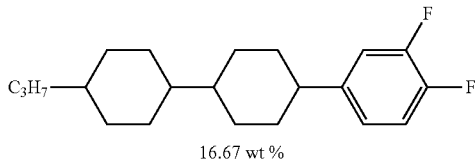

16.67 wt %

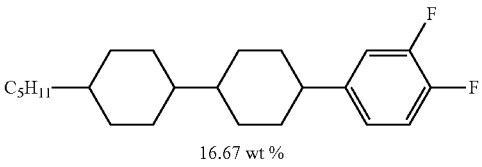

16.67 wt %

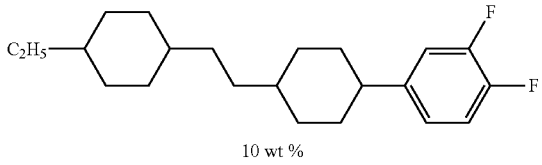

10 wt %

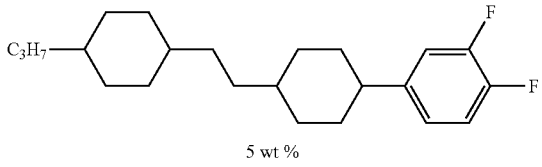

5 wt %

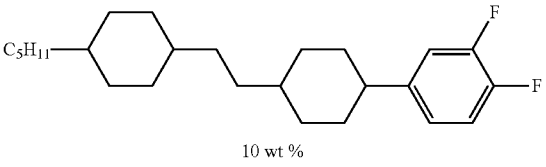

10 wt %

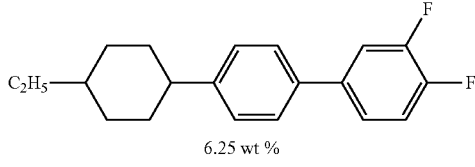

6.25 wt %

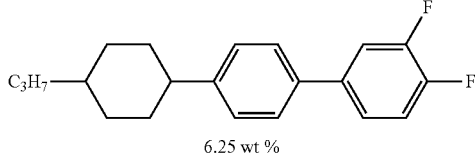

6.25 wt %

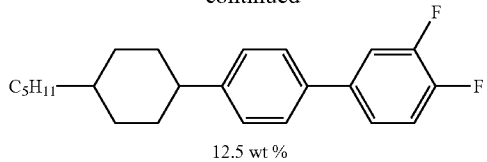

12.5 wt %

Methods for Calculating Values of Physical Properties of Compound (1)

Extrapolated values calculated from measured values of a liquid crystal composition containing compound (1) in accordance with an extrapolation method expressed in an equation below are described as values of physical properties of compound (1).

(Extrapolated value)={100×(Measured value of a sample)−(% by weight of base liquid crystal)}× (Measured value of base liquid crystal)/(% by weight of compound).

When a smectic phase or crystals precipitated at 25° C. even when a ratio of a liquid crystal compound to the base liquid crystal is 15% by weight of the liquid crystal to 85% by weight of the base liquid crystal, for example, a ratio of the liquid crystal compound to the base liquid crystal was changed in the order of (10% by weight: 90% by weight), (5% by weight: 95% by weight) and (1% by weight: 99% by weight), and then the values of physical properties of the sample were determined at a ratio in which the smectic phase or the crystals did not precipitate at 25° C.

Most of the measurement methods are applied as described in EIAJ ED-2521A, the Standards of Electronic Industries Association of Japan, or modified thereon. No TFT was attached to a TN device and a VA device used for measurement.

Phase Structure and Transition Temperature (° C.)

Measurement was carried out according to methods (1) and (2) described below.

(1) A sample was placed on a hot plate of a melting point apparatus (FP-52 Hot Stage made by Mettler-Toledo International Inc.) equipped with a polarizing microscope, and a state of phase and a change thereof were observed with the polarizing microscope while the compound was heated at a rate of 3° C. per minute, and a kind of the phase was specified.

(2) A sample was heated and then cooled at a rate of 3° C. per minute using a Perkin-Elmer differential scanning calorimeter, DSC-7 System or Diamond DSC System. A starting point (on set) of an endothermic peak or an exothermic peak caused by a phase change of the sample was determined by means of extrapolation, and thus a phase transition temperature was determined.

Hereinafter, a crystal was expressed as C. When crystals were distinguishable, each of the crystals was expressed as $C_1$ or $C_2$. A glass state was expressed as G A smectic phase or a nematic phase was expressed as S or N, respectively. A liquid (isotropic) was expressed using a symbol Iso. When a smectic B phase and a smectic A phase were distinguishable in the smectic phases, each of the phases was expressed as SmB or SmA. As an expression of a phase transition temperature, for example, "C 50.0 N 100.0 Iso" means that a phase transition temperature from crystals to a nematic phase (CN) is 50.0° C., and a phase transition temperature from the nematic phase to a liquid (NI) is 100.0° C. A same rule applied to any other expression.

Maximum Temperature of a Nematic Phase ($T_{NI}$; ° C.)

A sample (a liquid crystal composition or a mixture of the liquid crystal compound and a base liquid crystal) was placed on a hot plate of a melting point apparatus (FP-82 Hot Stage made by Mettler-Toledo International Inc.) equipped with a polarizing microscope, and was observed with the polarizing microscope while being heated at a rate of 1° C. per minute. Temperature at which part of the sample began to change from a nematic phase to an isotropic liquid was described as a maximum temperature. Hereinafter, a higher limit of a temperature range of the nematic phase may be occasionally abbreviated simply as "maximum temperature."

Compatibility at a Low Temperature

Samples were prepared in which a liquid crystal compound was mixed with a base liquid crystal for the liquid crystal compound to be 20% by weight, 15% by weight, 10% by weight, 5% by weight, 3% by weight and 1% by weight, and put in glass vials. After the glass vials were kept in freezers at −10° C. or −20° C. for a predetermined period of time, whether or not a crystal or a domain of a smectic phase was generated was observed.

Viscosity (Bulk Viscosity; η; Measured at 20° C.; mPa·s)

Measurement was carried out using an E-type rotational viscometer.

Viscosity (Rotational Viscosity; γ1; Measured at 25° C.; mPa·s)

Rotational viscosity was measured according to the method described in M. Imai et al., Molecular Crystals and Liquid Crystals, Vol. 259, p. 37 (1995). A sample (a liquid crystal composition or a mixture of the liquid crystal compound and a base liquid crystal) was placed in a VA device in which a distance (cell gap) between two glass substrates was 20 micrometers. Voltage was stepwise applied to the device in the range of 30 V to 50 V at an increment of 1 V. After a period of 0.2 second with no voltage application, voltage was applied repeatedly under the conditions of only one of rectangular waves (rectangular pulse; 0.2 second) and no voltage application (2 seconds). A peak current and a peak time of a transient current generated by the applied voltage were measured. A value of the rotational viscosity was obtained from the measured values and a calculation equation (8) on page 40 of the paper presented by M. Imai et al. In addition, as dielectric anisotropy necessary for the calculation, a value obtained by measuring the dielectric anisotropy described below was used.

Optical Anisotropy (Refractive Index Anisotropy; Measured at 25° C.; Δn)

Measurement was carried out using an Abbe refractometer with a polarizing plate attached to an ocular using light having a wavelength of 589 nanometers under a temperature of 25° C. A surface of a main prism was rubbed in one direction, and then a sample (a liquid crystal composition or a mixture of the liquid crystal compound and a base liquid crystal) was added dropwise onto the main prism. A refractive index (n∥) was measured when the direction of polarized light was parallel to the direction of rubbing. A refractive index (n⊥) was measured when the direction of polarized light was perpendicular to the direction of rubbing. A value of refractive index anisotropy (Δn) was calculated from an equation: Δn=n∥−n⊥.

Dielectric Anisotropy (Δ∈; Measured at 25° C.)

An ethanol (20 mL) solution of octadecyltriethoxysilane (0.16 mL) was applied to a well-washed glass substrate. After rotating a glass substrate with a spinner, the glass substrate was heated at 150° C. for 1 hour. A VA device in which a distance (cell gap) was 20 micrometers was assembled from two glass substrates.

A polyimide alignment film was prepared on the glass substrates in a similar manner. After rubbing treatment was applied to the alignment film formed on the glass substrates, a TN device in which a distance between two glass substrates was 9 micrometers and a twist angle was 80 degrees was assembled.

A sample (a liquid crystal composition or a mixture of the liquid crystal compound and a base liquid crystal) was put in the VA device obtained, a voltage of 0.5 V (1 kHz, sine waves) was applied to the sample, and then dielectric constant ($\in\|$) in the major axis direction of liquid crystal molecules was measured.

Moreover, the sample (the liquid crystal composition or the mixture of the liquid crystal compound and the base liquid crystal) was put in the TN device obtained, a voltage of 0.5 V (1 kHz, sine waves) was applied to the sample, and then dielectric constant ($\in\perp$) in the minor axis direction of the liquid crystal molecules was measured. A value of dielectric anisotropy was calculated from an equation of $\Delta\in=\in\|-\in\perp$.
Elastic Constants ($K_{11}$, $K_{22}$ and $K_{33}$; Measured at 25° C.)

Elastic constants in a liquid crystal material are classified into three constants: splay, twist and bend elastic constants corresponding to each deformation, and expressed as $k_{11}$, $k_{22}$ and $k_{33}$, respectively. Elastic Constant Measurement System Model EC-1 made by TOYO Corporation was used for the measurement. A sample was put in a vertical alignment cell in which a distance (cell gap) between two glass substrates was 20 micrometers. An electric charge of 20 V to 0 V was applied to the cell, and electrostatic capacity and applied voltage were measured. Measured values of the electrostatic capacity (C) and the applied voltage (V) were fitted to equation (2.98) and equation (2.101) on page 75 of "Liquid Crystal Device Handbook (Ekisho Debaisu Handobukku in Japanese)" (The Nikkan Kogyo Shimbun, Ltd.) and values of elastic constants were obtained from equation (2.100).

Example 1

Synthesis of compound (I-1-1-16-1) was performed according to a scheme below.

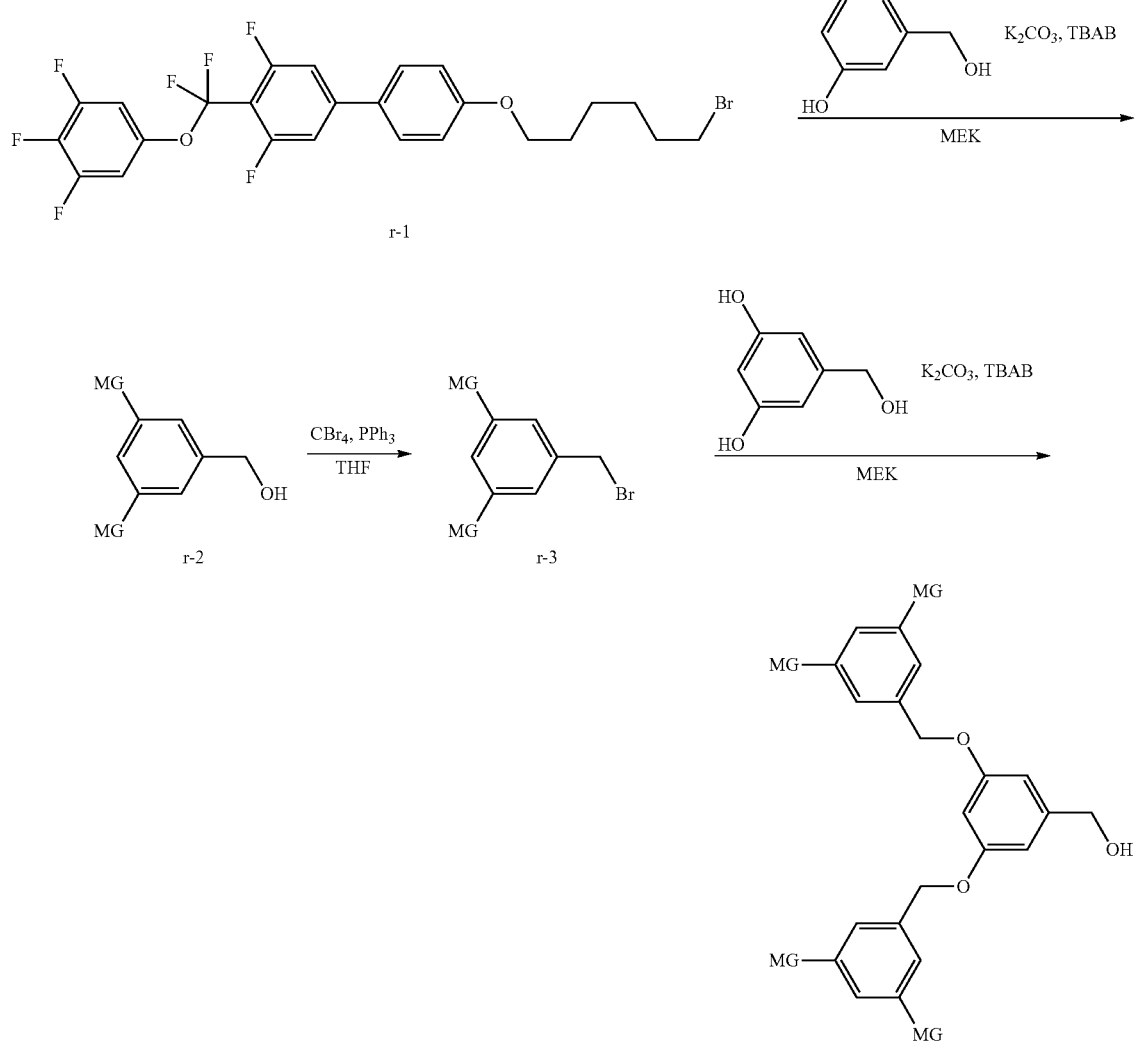

Formula 37

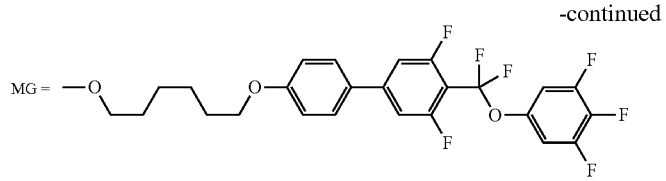

First Step:

To 1.0 g of 3,5-dihydroxybenzyl alcohol dissolved in 20 mL of 2-butanone, 2.3 g of potassium carbonate and 0.55 g of tetrabutylammonium bromide (TBAB) were added thereto, and then 9.6 g of 5-((4-(6-hydroxyhexyloxy)phenyl)phenyl)-difluoromethoxy)-1,2,3-trifluorobenzene (r-1) dissolved in 10 mL of 2-butanone was added thereto, and the resultant mixture was stirred for 6 hours under heating reflux. Water was added to the resultant reaction mixture to terminate a reaction, extraction was carried out with ethyl acetate, and a combined organic layer was washed with saturated brine, and then dried over anhydrous magnesium sulfate. A solvent was distilled off under reduced pressure, a residue was purified by silica gel column chromatography (eluent: heptane:ethyl acetate=1:1 (in a volume ratio)), and thus 7.0 g (6.32 mmol) of compound (r-2) was obtained.

Second Step:

Under a nitrogen atmosphere, 3.32 g of triphenylphosphine was added to 7.0 g of compound (r-2) dissolved in 50 mL of tetrahydrofuran (THF) and 3.14 g of carbon tetrabromide, and the resultant mixture was stirred at room temperature for 4 hours. A crystal precipitated was separated by suction filtration, and then washed with diethyl ether, and A filtrate was distilled under reduced pressure to remove a solvent. A residue was purified by silica gel column chromatography (eluent: heptane:toluene=1:2 (in a volume ratio)), and thus 3.75 g (3.2 mmol) of compound (r-3) was obtained.

Third Step:

To 0.22 g of 3,5-dihydroxybenzyl alcohol dissolved in 10 mL of 2-butanone, 0.88 g of potassium carbonate and 0.21 g of TBAB were added. Then, 3.75 g of compound (r-3) dissolved in 40 mL of 2-butanone was added thereto, and the resultant mixture was stirred under heating reflux for 6 hours. Water was added to the resultant reaction mixture to terminate a reaction, extraction was carried out with ethyl acetate, and a combined organic layer was washed with saturated brine, and then dried over anhydrous magnesium sulfate. A solvent was distilled off under reduced pressure, a residue was purified by silica gel column chromatography (eluent: toluene:ethyl acetate=9:1 (in a volume ratio)), and further purified by recrystallization from heptane/Solmix=5/1 (in a volume ratio), and thus 2.72 g (1.17 mmol) of compound (I-1-1-16-1) was obtained.

$^1$H-NMR (CDCl$_3$, δ (ppm)); 7.48 (d, 8H), 7.32 (d, 8H), 6.97 (d, 8H), 6.97 (t, 8H), 6.62 (d, 2H), 6.56 (d, 4H), 6.54 (t, 1H), 6.41 (t, 2H), 4.95 (s, 4H), 4.62 (s, 2H), 4.00 (t, 8H), 3.96 (t, 8H), 1.85-1.80 (m, 16H), 1.68 (s, OH), 1.56-1.54 (m, 16H).

Example 2

Synthesis of compound (I-1-1-16-2) was performed according to a scheme below.

Formula 38

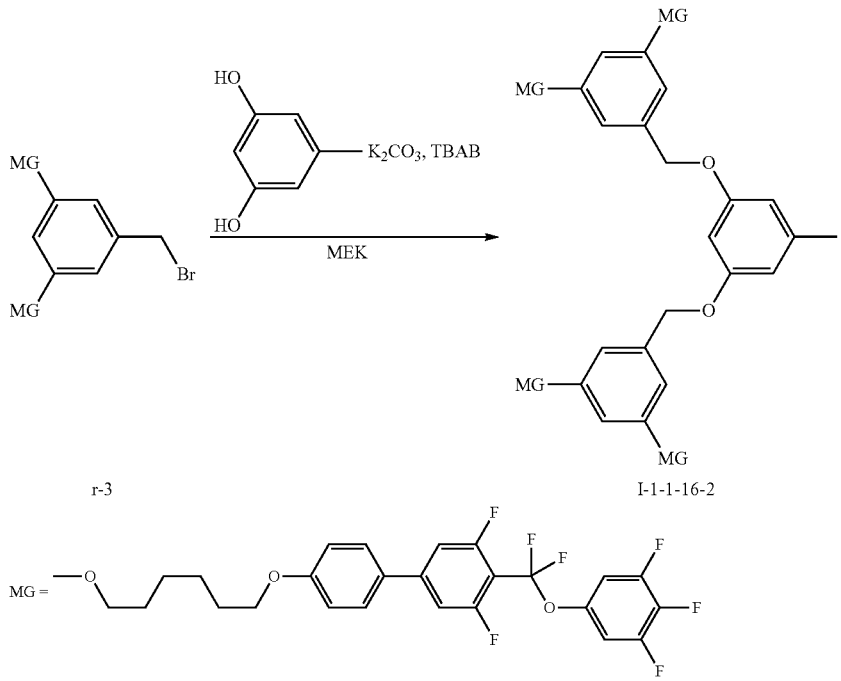

To 0.23 g of 3,5-dihydroxytoluene monohydrate dissolved in 10 mL of 2-butanone, 0.88 g of potassium carbonate and 0.21 g of TBAB were added. Then, 3.75 g of compound (r-3) dissolved in 40 mL of 2-butanone was added thereto, and the resultant mixture was stirred under heating reflux for 6 hours. Water was added to the resultant reaction mixture to terminate a reaction, extraction was carried out with ethyl acetate, and a combined organic layer was washed with saturated brine, and then dried over anhydrous magnesium sulfate. A solvent was distilled off away under reduced pressure, a residue was purified by silica gel column chromatography (eluent: toluene), and further purified by recrystallization from heptane/diethyl ether=5/1 (in a volume ratio), and thus 2.25 g (9.76 mmol) of compound (I-1-1-16-2) was obtained.

$^1$H-NMR (CDCl$_3$, δ (ppm)); 7.48 (d, 8H), 7.14 (d, 8H), 6.98 (t, 8H), 6.97 (d, 8H), 6.57 (d, 4H), 6.44 (d, 1H), 6.43 (d, 2H), 6.40 (t, 2H), 4.92 (s, 4H), 4.00 (t, 8H), 3.96 (t, 8H), 2.29 (s, 3H), 1.85-1.80 (m, 16H), 1.55-1.54 (m, 16H).

Example 3

Synthesis of compound (I-1-2-3-1) was performed according to a scheme below.

First Step:

To 1.2 g of 3,5-dihydroxybenzyl alcohol dissolved in 30 mL of 2-butanone, 2.7 g of potassium carbonate and 0.60 g of tetrabutylammonium bromide (TBAB) were added. Then, 7.9 g of 4-(6-hydroxyhexyloxy)phenyl-2,3-difluorophenetole (r-4) dissolved in 15 mL of 2-butanone was added thereto, and the resultant mixture was stirred under heating reflux for 6 hours. Water was added to the resultant reaction mixture to terminate a reaction, extraction was carried out with ethyl acetate, and a combined organic layer was washed with saturated brine, and then dried over anhydrous magnesium sulfate. A solvent was distilled off under reduced pressure, a residue was purified by silica gel column chromatography (eluent: heptane:ethyl acetate=6:4 (in a volume ratio)), and thus 5.89 g (7.30 mmol) of compound (r-5) was obtained.

Second Step:

Under a nitrogen atmosphere, 3.83 g of triphenyl phosphine was added to 5.89 g of compound (r-5) dissolved in 50 mL of tetrahydrofuran (THF) and 3.65 g of carbon tetrabromide, and the resultant mixture was stirred at room temperature for 4 hours. A crystal precipitated was separated by suction filtration, and then washed with diethyl ether, and a solvent of a filtrate thereof was distilled off under reduced pressure. A residue was purified by silica gel column chromatography (eluent: toluene), and thus 6.33 g (7.29 mmol) of compound (r-6) was obtained.

Formula 39

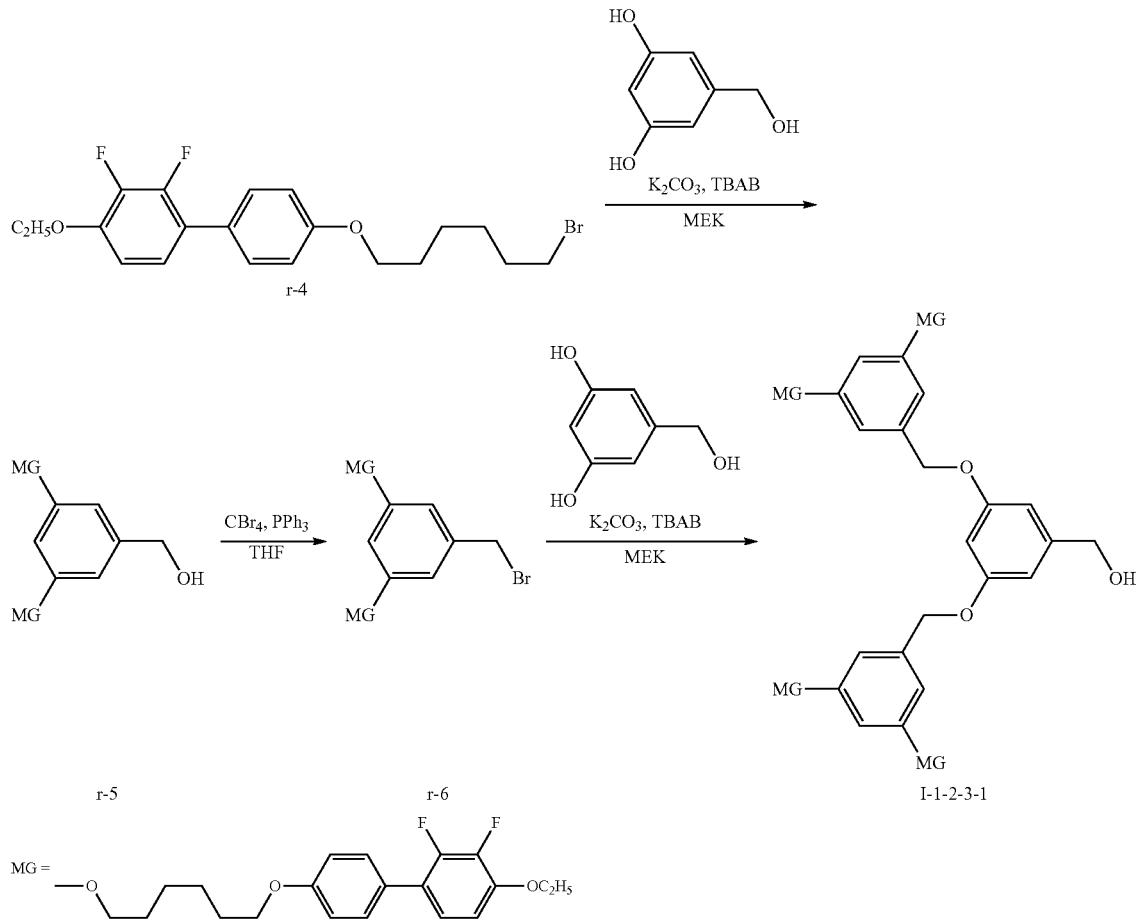

¹H-NMR (CDCl₃, δ (ppm)); 7.40 (d, 8H), 7.03 (td, 4H), 6.94 (d, 8H), 6.75 (td, 4H), 6.60 (d, 2H), 6.56 (d, 4H), 6.53 (t, 1H), 6.41 (t, 2H), 4.95 (s, 4H), 4.60 (s, 2H), 4.12 (q, 8H), 3.98 (t, 8H), 3.95 (t, 8H), 1.83-1.79 (m, 16H), 1.54-1.53 (m, 16H), 1.46 (t, 12H).

Example 4

Synthesis of compound (I-1-1-5-1) was performed according to a scheme below.

added thereto, and the resultant mixture was stirred under heating reflux for 6 hours. Water was added to the resultant reaction mixture to terminate a reaction, extraction was carried out with ethyl acetate, and a combined organic layer was washed with saturated brine, and then dried over anhydrous magnesium sulfate. A solvent was distilled off under reduced pressure, a residue was purified by silica gel column chromatography (eluent: heptane:ethyl acetate=1:1 (in a volume ratio)), and thus 3.26 g (4.13 mmol) of compound (r-8) was obtained.

Formula 40

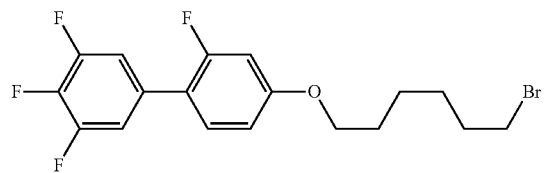
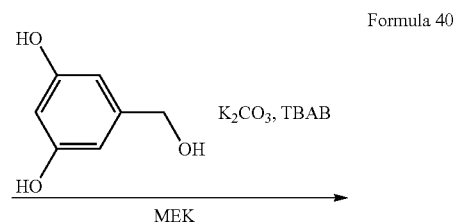
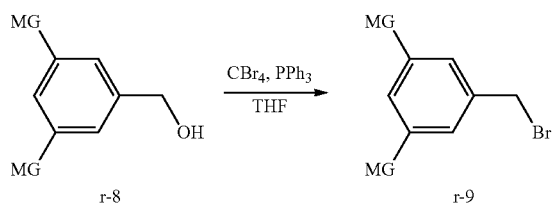
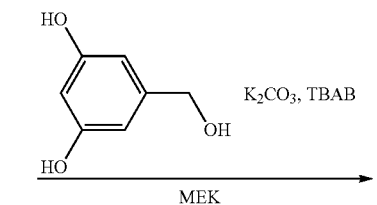
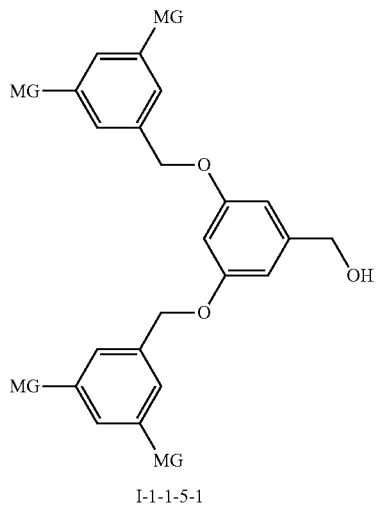
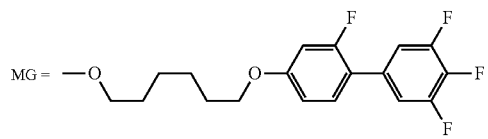

First Step:

To 1.0 g of 3,5-dihydroxybenzyl alcohol dissolved in 20 mL of 2-butanone, 2.3 g of potassium carbonate and 0.55 g of tetrabutylammonium bromide (TBAB) were added. Then, 6.9 g of 5-(6-hydroxyhexyloxy)-2-fluorophenyl-1,2,3-trifluorobenzene (r-7) dissolved in 10 mL of 2-butanone was Second Step:

Under a nitrogen atmosphere, 2.17 g of triphenylphosphine was added to 3.26 g of compound (r-8) dissolved in 50 mL of tetrahydrofuran (THF) and 2.06 g of carbon tetrabromide, and the resultant mixture was stirred at room temperature for 4 hours. A crystal precipitated was separated by suction filtration, and then washed with diethyl ether, and A filtrate was distilled under reduced pressure to remove a solvent. A residue was purified by silica gel column chromatography (eluent: heptane:toluene=1:2 (in a volume ratio)), and thus 2.28 g (2.67 mmol) of compound (r-9) was obtained.

Third Step:

To 0.22 g of 3,5-dihydroxybenzyl alcohol dissolved in 10 mL of 2-butanone, 0.74 g of potassium carbonate and 0.17 g of TBAB were added. Then, 2.28 g of compound (r-9) dissolved in 40 mL of 2-butanone was added thereto, and the resultant mixture was stirred under heating reflux for 6 hours. Water was added to the resultant reaction mixture to terminate a reaction, extraction was carried out with ethyl acetate, and a combined organic layer was washed with saturated brine, and then dried over anhydrous magnesium sulfate. A solvent was distilled off under reduced pressure, a residue was purified by silica gel column chromatography (eluent: toluene/ethyl acetate=9/1 (in a volume ratio)), and further purified by recrystallization from heptane/Solmix=5/1 (in a volume ratio), and thus 1.1 g (0.65 mmol) of compound (I-1-1-5-1) was obtained.

$^1$H-NMR (CDCl$_3$, δ (ppm)); 7.24 (dd, 4H), 7.11 (t, 8H), 6.74 (dd, 4H), 6.68 (dd, 4H), 6.61 (d, 2H), 6.56 (d, 4H), 6.53 (t, 1H), 6.40 (t, 2H), 4.95 (s, 4H), 4.62 (s, 2H), 3.98 (t, 8H), 3.96 (t, 8H), 1.85-1.80 (m, 16H), 1.68 (s, OH), 1.56-1.54 (m, 16H).

Example 5

Synthesis of compound (I-1-1-5-2) was performed according to a scheme below.

Formula 41

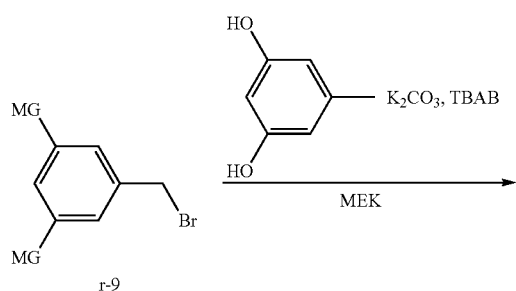

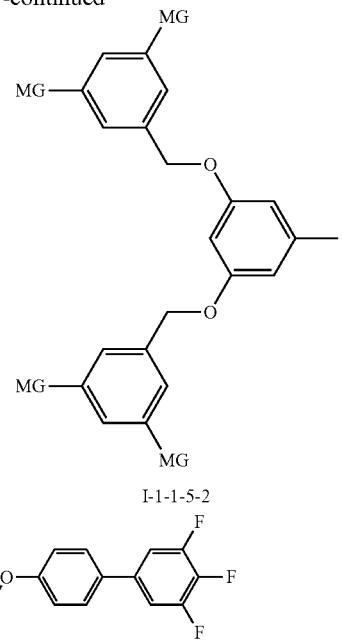

To 0.18 g of 3,5-dihydroxytoluene monohydrate dissolved in 10 mL of 2-butanone, 0.70 g of potassium carbonate and 0.16 g of TBAB were added. Then, 2.16 g of compound (r-9) dissolved in 40 mL of 2-butanone was added thereto, and the resultant mixture was stirred under heating reflux for 6 hours. Water was added to the resultant reaction mixture to terminate a reaction, extraction was carried out with ethyl acetate, and a combined organic layer was washed with saturated brine, and then dried over anhydrous magnesium sulfate. A solvent was distilled off under reduced pressure, a residue was purified by silica gel column chromatography (eluent: toluene), and further purified by recrystallization from heptane/diethyl ether=5/1 (in a volume ratio), and thus 0.8 g (0.48 mol) of compound (I-1-1-5-2) was obtained.

$^1$H-NMR (CDCl$_3$, δ (ppm)); 7.23 (dd, 4H), 7.11 (t, 8H), 6.74 (dd, 4H), 6.68 (dd, 4H), 6.55 (d, 4H), 6.55 (t, 1H), 6.42 (d, 2H), 6.40 (t, 2H), 4.92 (s, 4H), 3.97 (t, 8H), 3.95 (t, 8H), 2.29 (s, 3H), 1.85-1.80 (m, 16H), 1.56-1.54 (m, 16H).

Values of physical properties of compound (I-1-1-5-2) are shown in Table 20.

Example 6

Synthesis of compound (I-1-3-2-2) was performed according to a scheme below.

Formula 42

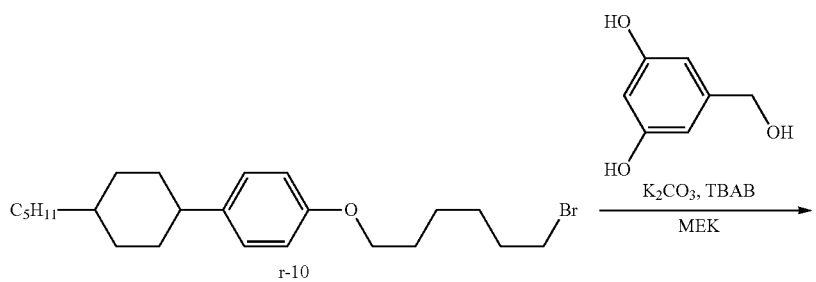

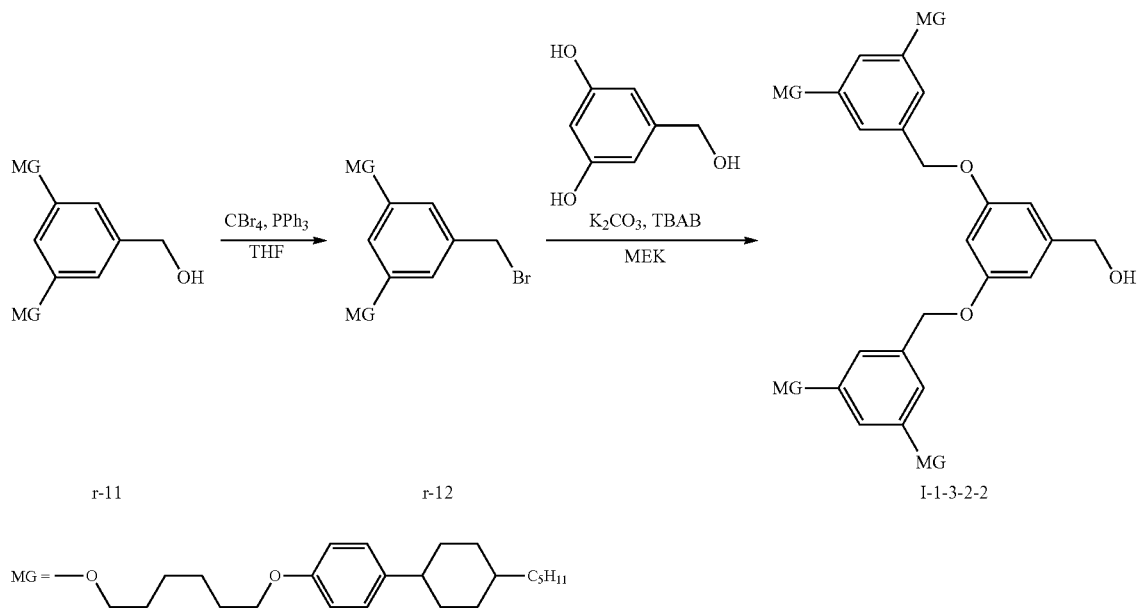

First Step:

To 1.75 g of 3,5-dihydroxybenzyl alcohol dissolved in 40 mL of 2-butanone, 4.15 g of potassium carbonate and 0.97 g of tetrabutylammonium bromide (TBAB) were added. Then, 12.3 g of 1-(6-hydroxyhexyloxy)phenyl-4-pentylbenzene (r-10) dissolved in 20 mL of 2-butanone was added thereto, and the resultant mixture was stirred under heating reflux for 6 hours. Water was added to the resultant reaction mixture to terminate a reaction, extraction was carried out with ethyl acetate, and a combined organic layer was washed with saturated brine, and then dried over anhydrous magnesium sulfate. A solvent was distilled off under reduced pressure, a residue was purified by silica gel column chromatography (eluent: heptane:ethyl acetate=7:3 (in a volume ratio)), and thus 8.82 g (11.1 mmol) of compound (r-11) was obtained.

Second Step:

Under a nitrogen atmosphere, 5.15 g of triphenylphosphine was added to 7.82 g of compound (r-11) dissolved in 100 mL of tetrahydrofuran (THF) and 4.88 g of carbon tetrabromide, and the resultant mixture was stirred at room temperature for 4 hours. A crystal precipitated was separated by suction filtration, and then washed with diethyl ether, and A filtrate was distilled under reduced pressure to remove a solvent. A residue was purified by silica gel column chromatography (eluent: toluene:heptane=4:1 (in a volume ratio)), and thus 8.38 g (9.74 mmol) of compound (r-12) was obtained.

Third Step:

To 0.22 g of 3,5-dihydroxybenzyl alcohol dissolved in 20 mL of 2-butanone, 0.97 g of potassium carbonate and 0.22 g of TBAB were added. Then, 3.02 g of compound (r-12) dissolved in 30 mL of 2-butanone was added thereto, and the resultant mixture was stirred under heating reflux for 6 hours. Water was added to the resultant reaction mixture to terminate a reaction, extraction was carried out with ethyl acetate, and a combined organic layer was washed with saturated brine, and then dried over anhydrous magnesium sulfate. A solvent was distilled off under reduced pressure, a residue was purified by silica gel column chromatography (eluent: toluene/ethyl acetate=9/1 (in a volume ratio)), and further purified by recrystallization from heptane/Solmix=5/1 (in a volume ratio), and thus 2.25 g (1.32 mmol) of compound (I-1-3-2-2) was obtained.

$^1$H-NMR (CDCl$_3$, δ (ppm)); 7.09 (d, 8H), 6.81 (d, 8H), 6.59 (d, 2H), 6.55 (d, 4H), 6.53 (t, 1H), 6.39 (t, 2H), 4.93 (s, 4H), 4.74 (d, 2H), 3.93 (t, 8H), 3.92 (t, 8H), 2.39 (tt, 4H), 1.85-1.83 (m, 16H), 1.79-1.77 (m, 16H), 1.53-1.49 (m, 16H), 1.43-1.36 (m, 8H), 1.35-1.18 (m, 37H), 1.06-0.98 (m, 8H), 0.89 (t, 12H).

Example 7

Synthesis of compound (I-1-1-16-7) was performed according to a scheme below.

Formula 43

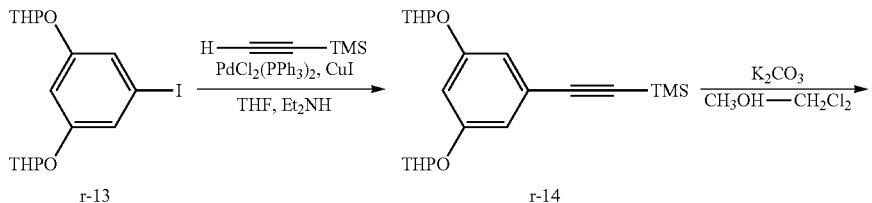

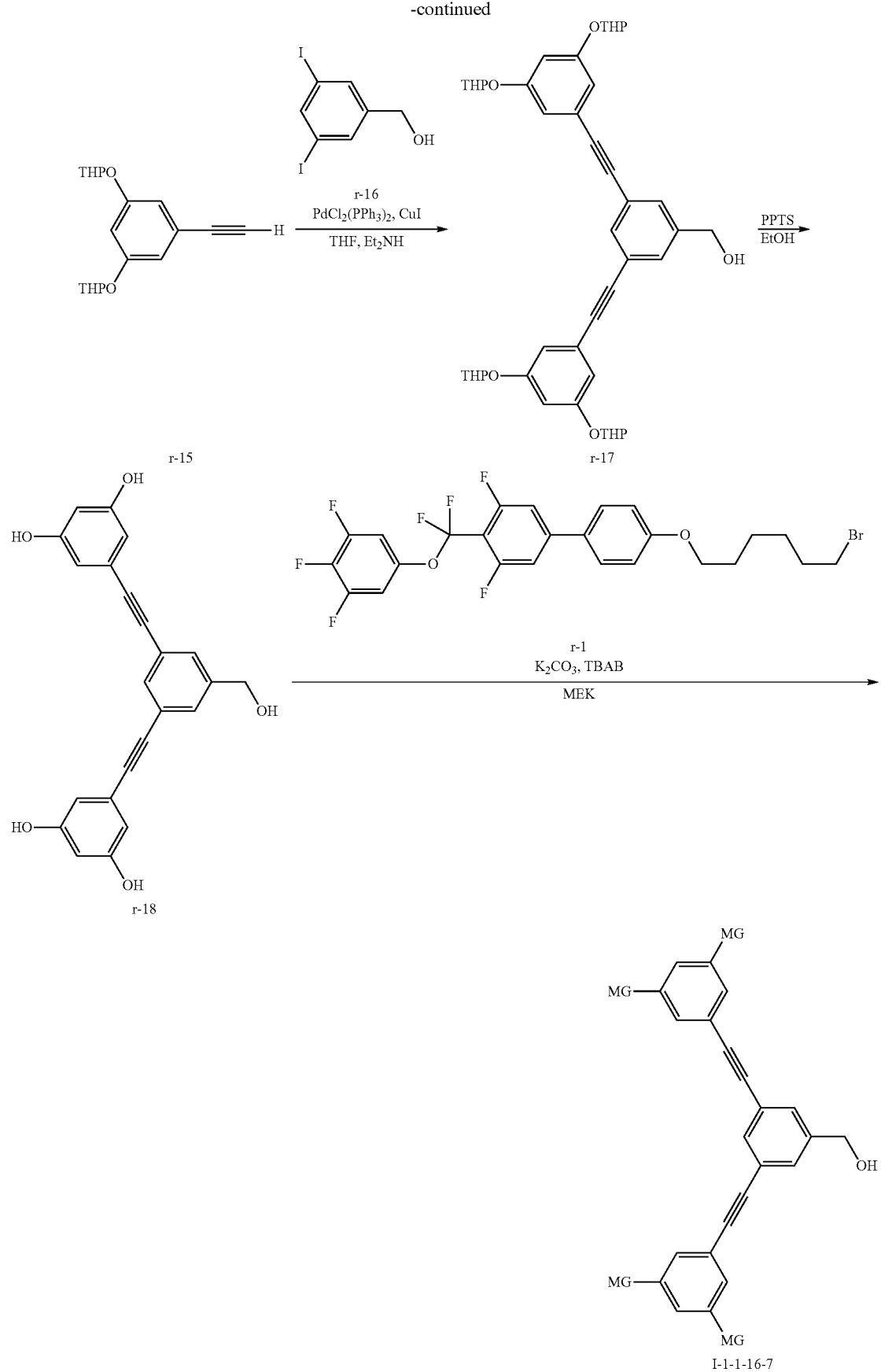

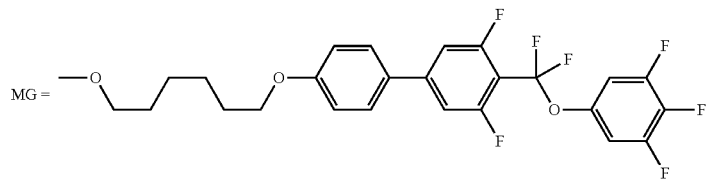

First Step:

Under an argon atmosphere, 3.68 g of trimethylsilyl acetylene was gradually added dropwise to 13.7 g of compound (r-13), 2.39 g of dichlorobis(triphenylphosphine)palladium, and 0.65 g of copper iodide (I) that were dissolved in 125 mL of THF and 125 mL of diethylamine that were subjected to degassing treatment, and the resultant mixture was stirred at room temperature for 2 hours. After reaction completion, a solvent was distilled off, and a residue was purified by silica gel column chromatography (eluate: heptane:toluene=6:4 (in a volume ratio)), and thus 7.69 g (20.5 mmol) of compound (r-14) was obtained.

Second Step:

Under a nitrogen atmosphere, 3.40 g of potassium carbonate was added to 7.69 g of compound (r-14) dissolved in 60 mL of chloromethane and 60 mL of methanol, and the resultant mixture was stirred at room temperature for 4 hours. Water was added to the resultant reaction mixture to terminate a reaction, extraction was carried out with dichloromethane, and a combined organic layer was washed with saturated brine, and then dried over anhydrous magnesium sulfate. A filtrate thereof was distilled under reduced pressure to remove a solvent. A residue was purified by silica gel column chromatography (eluent: heptane:ethyl acetate=6:4 (in a volume ratio)), and thus 1.31 g (4.33 mmol) of compound (r-15) was obtained.

Third Step:

Under an argon atmosphere, 1.31 g of compound (r-15) dissolved in 10 mL of THF was added dropwise to 0.92 g of compound (r-16), 0.36 g of dichlorobis(triphenylphosphine)palladium, and 0.1 g of copper iodide (I) that were dissolved in 10 mL of THF and 10 mL of diethylamine that were subjected to degassing treatment, and the resultant mixture was stirred at room temperature for 2 hours. After reaction completion, a solvent was distilled off, and a residue was purified by silica gel column chromatography (eluate: heptane:ethyl acetate=7:3 (in a volume ratio)), and thus 1.39 g (1.96 mmol) of compound (r-17) was obtained.

Fourth Step:

Under a nitrogen atmosphere, 0.19 g of pyridinium p-toluenesulfonate was added to 1.39 g of compound (r-17) dissolved in 100 mL of ethanol, and the resultant mixture was stirred under heating reflux for 4 hours. Water was added to the resultant reaction mixture to terminate a reaction, extraction was carried out with ethyl acetate, and a combined organic layer was washed with saturated brine, and then dried over anhydrous magnesium sulfate. A filtrate thereof was distilled under reduced pressure to remove a solvent. A residue was purified by silica gel column chromatography (eluent: heptane:ethyl acetate=1:1 (in a volume ratio)), and thus 0.73 g (1.96 mmol) of compound (r-18) was obtained.

Fifth Step:

To 0.73 g of compound (r-18) dissolved in 30 mL of 2-butanone, 1.08 g of potassium carbonate and 0.25 g of TBAB were added. Then, 2.21 g of compound (r-1) dissolved in 20 mL of 2-butanone was added thereto, and the resultant mixture was stirred under heating reflux for 6 hours. Water was added to the resultant reaction mixture to terminate a reaction, extraction was carried out with ethyl acetate, and a combined organic layer was washed with saturated brine, and then dried over anhydrous magnesium sulfate. A solvent was distilled off under reduced pressure, a residue was purified by silica gel column chromatography (eluent: heptane:ethyl acetate=9:1 (in a volume ratio)), and further purified by recrystallization from heptane/Solmix=5/1 (in a volume ratio), and thus 2.1 g (0.90 mmol) of compound (I-1-1-16-7) was obtained.

$^1$H-NMR (CDCl$_3$, δ (ppm)); 7.38 (t, 1H), 7.67 (d, 2H), 7.46 (d, 8H), 7.35 (d, 4H), 7.33 (d, 8H), 6.98 (d, 8H), 6.95 (t, 8H), 6.32 (t, 2H), 4.61 (s, 2H), 4.02 (t, 8H), 3.98 (t, 8H), 1.87-1.81 (m, 16H), 1.66 (s, OH), 1.55-1.52 (m, 16H).

Comparative Example 1

As a comparative compound, a compound represented by general formula (C) (hereinafter, referred to as "LC-6-G2OH") that was disclosed in Non-patent literature No. 3 was prepared according to a scheme below.

Formula 44

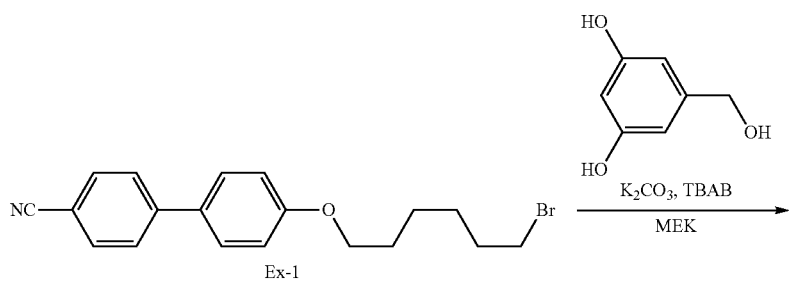

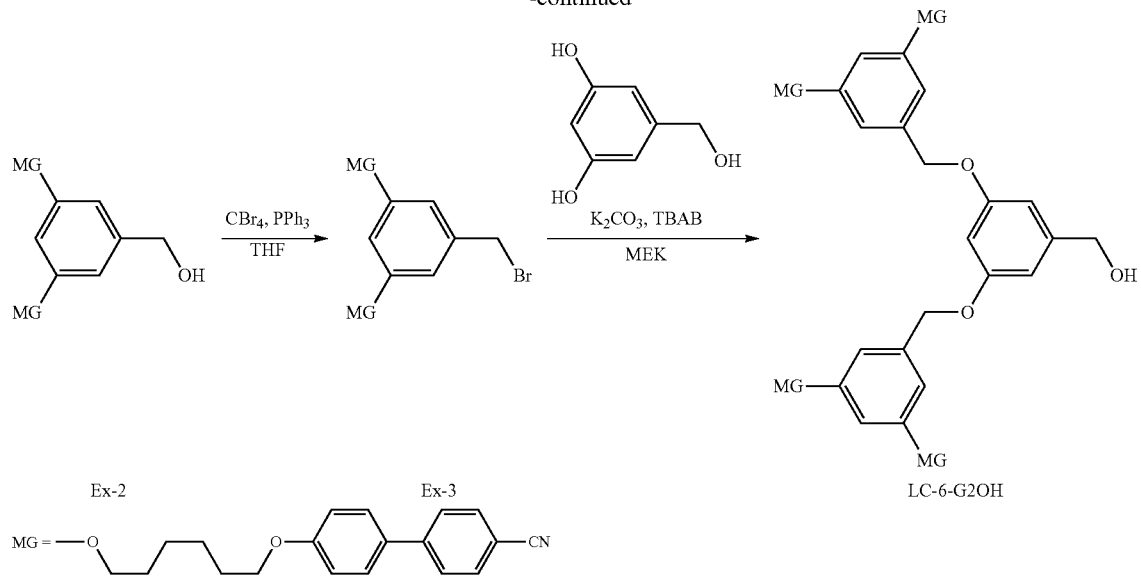

First Step:

To 2.0 g of 3,5-dihydroxybenzyl alcohol dissolved in 40 mL of 2-butanone, 6.2 g of potassium carbonate and 1.45 g of tetrabutylammonium bromide (TBAB) were added. Then, 10.8 g of 1-(6-hydroxyhexyloxy)phenyl-4-cyanobenzene (Ex-1) dissolved in 20 mL of 2-butanone was added thereto, and the resultant mixture was stirred under heating reflux for 6 hours. Water was added to the resultant reaction mixture to terminate a reaction, extraction was carried out with ethyl acetate, and a combined organic layer was washed with saturated brine, and then dried over anhydrous magnesium sulfate. A solvent was distilled off under reduced pressure, a residue was purified by silica gel column chromatography (eluent: heptane:ethyl acetate=1:1 (in a volume ratio)), and thus 3.74 g (5.38 mmol) of compound (Ex-2) was obtained.

Second Step:

Under a nitrogen atmosphere, 2.83 g of triphenylphosphine was added to 3.74 g of compound (Ex-2) dissolved in 35 mL of tetrahydrofuran (THF) and 2.67 g of carbon tetrabromide, and the resultant mixture was stirred at room temperature for 4 hours. A crystal precipitated was separated by suction filtration, and then washed with diethyl ether, and a filtrate thereof was distilled under reduced pressure to remove a solvent. A residue was purified by silica gel column chromatography (eluent: toluene:ethyl acetate=1:1 (in a volume ratio)), and thus 3.35 g (4.42 mmol) of compound (Ex-3) was obtained.

Third Step:

To 0.31 g of 3,5-dihydroxybenzyl alcohol dissolved in 10 mL of 2-butanone, 1.22 g of potassium carbonate and 0.28 g of TBAB were added. Then, 3.35 g of compound (Ex-3) dissolved in 20 mL of 2-butanone was added thereto, and the resultant mixture was stirred under heating reflux for 6 hours. Water was added to the resultant reaction mixture to terminate a reaction, extraction was carried out with ethyl acetate, and a combined organic layer was washed with saturated brine, and then dried over anhydrous magnesium sulfate. A solvent was distilled off under reduced pressure, a residue was purified by silica gel column chromatography (eluent: toluene/ethyl acetate=7/3 (in a volume ratio)), and further purified by recrystallization from toluene/Solmix=1/2 (in a volume ratio), and thus 1.81 g (1.21 mmol) of compound (LC-6-G2OH) was obtained.

$^1$H-NMR (CDCl$_3$, δ (ppm)); 7.67 (dd, 16H), 7.55 (d, 8H), 7.01 (d, 8H), 6.81 (d, 8H), 6.59 (d, 2H), 6.55 (d, 4H), 6.65 (d, 1H), 6.60 (d, 2H), 6.56 (t, 1H), 6.45 (t, 2H), 4.99 (s, 4H), 4.66 (d, 2H), 4.04 (t, 8H), 3.99 (t, 8H), 1.90-1.83 (m, 16H), 1.79-1.77 (m, 16H).

Comparative compound LC-6-G2OH is a cyano-based compound as described above. Thus, the compound does not dissolve in base liquid crystal BM-1 used for the method for calculating the values of physical properties of the compounds obtained in Examples 1 to 6. Therefore, a cyano-based liquid crystal composition, product ZLI-1132, made by Merck KGaA was used for calculation of values of physical properties of compound LC-6-G2OH in place of base liquid crystal BM-1.

The values of physical properties of compound (1) obtained in Examples 1 to 6 and compound (LC-6-G2OH) in Comparative Example 1 are shown in Table 20. In Table 20, "solubility" refers to solubility in base liquid crystal BM-1 being a general fluorine-based liquid crystal material as a liquid crystal material.

TABLE 20

|  | Compound | Phase Transition Temperature (° C.) | $T_{NI}$ (° C.) | Δε | Δn | Solubility |
|---|---|---|---|---|---|---|
| Example 1 | I-1-1-16-1 | G 6.0 N 48.4 Iso | 46.8 | 15.1 | 0.126 | Good |
| Example 2 | I-1-1-16-2 | G 6.5 N 22.8 Iso | 28.6 | 12.6 | 0.128 | Good |
| Example 3 | I-1-2-3-1 | G 7.8 N 39.2 Iso | 49.1 | −2.9 | 0.133 | Good |
| Example 4 | I-1-1-5-1 | G −9.4 Iso | −39.9 | 8.43 | 0.080 | Good |
| Example 5 | I-1-1-5-2 | G −12.5 Iso | −127.2 | 6.43 | 0.072 | Good |
| Example 6 | I-1-3-2-2 | G SmA 84.0 Iso | 49.4 | −0.13 | 0.086 | Good |

TABLE 20-continued

| | Compound | Phase Transition Temperature (° C.) | $T_{NI}$ (° C.) | Δε | Δn | Solubility |
|---|---|---|---|---|---|---|
| Comparative Example 1 | LC-6-G2OH | G 32.2 N 83.9 Iso | 78.7 | 14.1 | 0.207 | Poor |

Examples 8 to 13, Comparative Example 2

Liquid crystal compositions were obtained by mixing compound (1) in Examples 1 to 6 and base liquid crystal BM-1. The values of physical properties of the compositions are shown in Table 21 as Examples 8 to 13, respectively. As Comparative Example 2, an attempt was made for manufacturing a liquid crystal composition by mixing comparative compound LC-6-G2OH with base liquid crystal BM-1 in a similar manner, but compound LC-6-G2OH did not dissolve in base liquid crystal BM-1, and such a liquid crystal composition was not obtained. Thus, values of physical properties thereof were not determined Therefore, the values of physical properties are expressed using a symbol "-." Comparative Example 3 refers to a liquid crystal composition consisting of BM-1 and without containing compound (1) of the invention.

TABLE 21

| | Compounds used | Content | $T_{NI}$ (° C.) | Δε | $k_{11}$ | $k_{22}$ | $k_{33}$ |
|---|---|---|---|---|---|---|---|
| Example 8 | I-1-1-16-1 | 3 wt % | 98.7 | 5.40 | 9.02 | 7.31 | 16.06 |
| Example 9 | I-1-1-16-2 | 20 wt % | 85.8 | 6.6 | 8.39 | 5.73 | 11.04 |
| Example 10 | I-1-2-3-1 | 20 wt % | 89.9 | 3.50 | 10.85 | 5.76 | 10.95 |
| Example 11 | I-1-1-5-1 | 3 wt % | 95.9 | 5.2 | 8.44 | 6.60 | 18.03 |
| Example 12 | I-1-1-5-2 | 15 wt % | 66.0 | 5.3 | 7.51 | 4.59 | 11.63 |
| Example 13 | I-1-3-2-2 | 15 wt % | 92.5 | 4.4 | 10.18 | 4.53 | 11.45 |
| Comparative Example 2 | LC-6-G2OH | No dissolution | — | — | — | — | — |
| Comparative Example 3 | Base liquid crystal BM-1 | — | 100.1 | 5.1 | 9.77 | 11.06 | 23.75 |

Furthermore, liquid crystal compositions as described below were manufactured. A parenthesized figure represents a ratio based on the total amount of the liquid crystal composition. Description of compounds used for the base liquid crystal is in accordance with an abbreviation method in Table 21. In Table 22, 1,4-cyclohexylene has a trans configuration. Unless otherwise noted, a ratio (percentage) of each compound is expressed in terms of weight percent (% by weight) based on the total weight of the composition. Values of characteristics of the liquid crystal compositions obtained are shown in the last part of each Example. The number described in the last part of the liquid crystal compound name (example: (formula number 3-100) in the column of the component of base liquid crystal BM-2 in Example 14) corresponds to the formula number showing each of compounds of components A to E exemplified previously.

TABLE 22

Table Method for Description of Compounds using Symbols
R—(A$_1$)—Z$_1$— ... —Z$_n$—(A$_n$)—R'

| 1) Left-terminal group R— | Symbol |
|---|---|
| $C_nH_{2n+1}$— | n- |
| $C_nH_{2n+1}O$— | nO— |
| $C_mH_{2m+1}OC_nH_{2n}$— | mOn— |
| $CH_2$=CH— | V— |
| $C_nH_{2n+1}$—CH=CH— | nV— |
| $CH_2$=CH—$C_nH_{2n}$— | Vn— |
| $C_mH_{2m+1}$—CH=CH—$C_nH_{2n}$— | mVn— |
| $CF_2$=CH— | VFF— |
| $CF_2$=CH—$C_nH_{2n}$— | VFFn— |

| 2) Right-terminal Group —R' | Symbol |
|---|---|
| —$C_nH_{2n+1}$ | -n |
| —$OC_nH_{2n+1}$ | —On |
| —COOCH$_3$ | —EMe |
| —CH=CH$_2$ | —V |
| —CH=CH—$C_nH_{2n+1}$ | —Vn |
| —$C_nH_{2n}$—CH=CH$_2$ | —nV |
| —$C_mH_{2m}$—CH=CH—$C_nH_{2n+1}$ | —mVn |
| —CH=CF$_2$ | —VFF |
| —F | —F |
| —Cl | —CL |
| —OCF$_3$ | —OCF3 |
| —OCHF$_2$ | —OCHF2 |
| —CF$_3$ | —CF3 |

| 3) Bonding Group —Z$_n$— | Symbol |
|---|---|
| —$C_nH_{2n}$— | n |
| —COO— | E |
| —CH=CH— | V |
| —CH$_2$O— | 1O |
| —OCH$_2$— | O1 |
| —CF$_2$O— | X |
| —OCF$_2$— | x |
| —C≡C— | T |

| 4) Ring Structure —A$_n$— | Symbol |
|---|---|
| ⬡ (cyclohexylene) | H |

TABLE 22-continued

Table Method for Description of Compounds using Symbols
R—(A$_1$)—Z$_1$—...—Z$_n$—(A$_n$)—R'

| Structure | Symbol |
|---|---|
| | B |
| | B(F) |
| | B(2F) |
| | B(F,F) |
| | B(2F,5F) |
| | B(2F,3F) |
| | Py |
| | G |

5) Example of Description

Example 1 3-HH-4

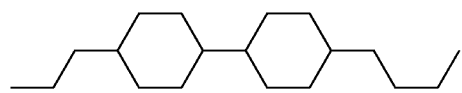

Example 2 3-HBB(F,F)—F

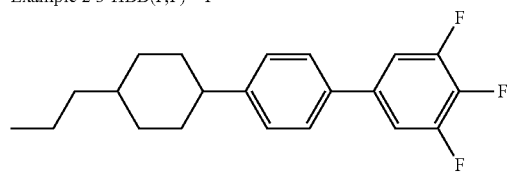

Physical properties of compounds were measured according to the methods described below. Most of the measurement methods are described in EIAJ ED-2521A, the Standard of Electronic Industries Association of Japan, or modified thereon.

(1) Maximum Temperature of a Nematic Phase (NI; ° C.)

A sample was placed on a hot plate in a melting point apparatus equipped with a polarizing microscope and was heated at a rate of 1° C. per minute. Temperature when part of the sample began to change from a nematic phase to an isotropic liquid was measured. Hereinafter, a higher limit of the temperature range of a nematic phase may be occasionally abbreviated as "maximum temperature."

(2) Minimum Temperature of a Nematic Phase ($T_c$; ° C.)

Samples each having a nematic phase were kept in freezers at temperatures of 0° C., −10° C., −20° C., −30° C. and −40° C. for 10 days, and then liquid crystal phases were observed. For example, when a sample maintained the nematic phase at −20° C. and changed to crystals or a smectic phase at −30° C., Tc was expressed as Tc≤−20° C. A lower limit of the temperature range of the nematic phase may be occasionally abbreviated as "minimum temperature."

(3) Optical Anisotropy (Δn; Measured at 25° C.)

Measurement was carried out by means of an Abbe refractometer with a polarizing plate mounted on an ocular, using light at a wavelength of 589 nanometers. A surface of a main prism was rubbed in one direction, and then a sample was dropped on the main prism. A refractive index (n∥) was measured when the direction of polarized light was parallel to the direction of rubbing. A refractive index (n⊥) was measured when the direction of polarized light was perpendicular to the direction of rubbing. A value of optical anisotropy was calculated from an equation: Δn=n∥−n⊥.

(4) Viscosity (Bulk Viscosity; η; Measured at 20° C.; mPa·s)

A cone-pate (E-type) viscometer was used for measurement.

(5) Dielectric Anisotropy (Δ∈; Measured at 25° C.)

An ethanol (20 mL) solution of octadecyltriethoxysilane (0.16 mL) was applied to a well-washed glass substrate. After rotating the glass substrate with a spinner, the glass substrate was heated at 150° C. for 1 hour. A VA device in which a distance (cell gap) was 20 micrometers was assembled from two glass substrates.

A polyimide alignment film was prepared on the glass substrates in a similar manner. After rubbing treatment was applied to the alignment film formed on the glass substrates, a TN device in which a distance between the two glass substrates was 9 micrometers and a twist angle was 80 degrees was assembled.

A sample (a liquid crystal composition or a mixture of the liquid crystal compound and a base liquid crystal) was put in the VA device obtained, a voltage of 0.5 V (1 kHz, sine waves) was applied to the sample, and then dielectric constant (∈∥) in the major axis direction of liquid crystal molecules was measured.

The sample (the liquid crystal composition or the mixture of the liquid crystal compound and the base liquid crystal) was put in the TN device obtained, a voltage of 0.5 V (1 kHz, sine waves) was applied to the sample, and then dielectric constant (∈⊥) in the minor axis direction of the liquid crystal molecules was measured.

A value of dielectric anisotropy was calculated from an equation of Δ∈=∈∥−∈⊥. A composition having a negative value has a negative dielectric anisotropy.

Example 14

A liquid crystal composition was prepared using:
compound (1) (I-1-1-16-1) (15%) and
base liquid crystal BM-2:

| | | |
|---|---|---|
| 3-HHXB(F,F)-F | (Formula number 3-100) | (10%) |
| 3-BB(F)B(F,F)XB(F,F)-F | (Formula number 4-47) | (2%) |
| 4-BB(F)B(F,F)XB(F,F)-F | (Formula number 4-47) | (7%) |
| 5-BB(F)B(F,F)XB(F,F)-F | (Formula number 4-47) | (7%) |
| V2-HHB-1 | (Formula number 13-1) | (12%) |
| 3-HH-V | (Formula number 12-1) | (29%) |
| 3-HH-V1 | (Formula number 12-1) | (11%) |
| 3-BB(F,F)XB(F,F)-F | (Formula number 13-1) | (7%) |

Values of physical properties of the liquid crystal composition obtained are shown in Table 23.

Example 15

A liquid crystal composition was prepared using:
compound (1) (I-1-1-16-2) (15%) and
base liquid crystal BM-2: Constituents and a compounding ratio of each component are identical with the constituents and the ratio in Example 14.

Values of physical properties of the liquid crystal composition obtained are shown in Table 23.

Example 16

A liquid crystal composition was prepared using:
compound (1) (I-1-1-5-1) (15%) and
base liquid crystal BM-2: Constituents and a compounding ratio of each component are identical with the constituents and the ratio in Example 14.

Values of physical properties of the liquid crystal composition obtained are shown in Table 23.

Example 17

A liquid crystal composition was prepared using:
compound (1) (I-1-2-3-1) (15%) and
base liquid crystal BM-3:

| | | |
|---|---|---|
| 3-HH-V | (Formula number 12-1) | (20%) |
| V-HHB-1 | (Formula number 13-1) | (10%) |
| V2-HHB-1 | (Formula number 13-1) | (5%) |
| 3-H2B(2F,3F)-O2 | (Formula number 6-4) | (15%) |
| 5-H2B(2F,3F)-O2 | (Formula number 6-4) | (15%) |
| 3-HBB(2F,3F)-O2 | (Formula number 7-7) | (10%) |
| 3-HBB(2F,3F)-O2 | (Formula number 7-7) | (10%) |

Values of physical properties of the liquid crystal composition obtained are shown in Table 23.

Example 18

A liquid crystal composition was prepared using:
compound (1) (I-1-3-2-2) (20%) and
base liquid crystal BM-3: Constituents and a compounding ratio of each component are identical with the constituents and the ratio in Example 17.

Values of physical properties of the liquid crystal composition obtained are shown in Table 23.

TABLE 23

| | $\Delta\epsilon$ | $k_{11}$ | $k_{22}$ | $K_{33}$ |
|---|---|---|---|---|
| Example 14 | 7.54 | — | 6.91 | — |
| Example 15 | 7.57 | — | 6.94 | — |
| Example 16 | 7.08 | — | 5.74 | — |
| Example 17 | −2.36 | 12.65 | — | 14.43 |
| Example 18 | −2.39 | 12.98 | — | 11.62 |

The composition in Example 14 shows a positive value of dielectric anisotropy and a small value of k22. Therefore, the composition is suitable for use in a device having the IPS mode. The composition of Example 15 shows a positive value of dielectric anisotropy and a small value of k22. Therefore, the composition in Example 15 is suitable for use in the device having the IPS mode. The composition in Example 16 shows a positive value of dielectric anisotropy and a small value of k22. Therefore, the composition in Example 16 is suitable for use in the device having the IPS mode.

The composition in Example 17 shows a negative value of dielectric anisotropy and a small value of k33. Therefore, the composition in Example 17 is suitable for use in a device having the VA mode or the PSA mode. The composition in Example 18 shows a negative value of dielectric anisotropy and a small value of k33. Therefore, the composition in Example 18 is suitable for use in the device having the VA mode or the PSA mode.

Thus, a liquid crystal composition showing any of a positive or negative value of dielectric anisotropy can be obtained by containing compound (1) of the invention as the constituent. The liquid crystal composition obtained can correspond to various modes, such as the PS mode, the VA mode and the PSA mode.

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

INDUSTRIAL APPLICABILITY

A compound per se of the invention shows a low threshold voltage and has an excellent compatibility with other liquid crystal compounds. The compound further has general physical properties required for the compound, namely, stability to heat, light and so forth, a suitable optical anisotropy and a suitable dielectric anisotropy. A liquid crystal composition of the invention contains at least one of the compounds, and has a high maximum temperature of a nematic phase, a low minimum temperature of the nematic phase, a small viscosity, a suitable optical anisotropy and a low threshold voltage. A liquid crystal display device of the invention includes the composition, and has a wide usable temperature range, a short response time, a large contrast ratio and a low driving voltage, and therefore can be used for a liquid crystal projector, a liquid crystal television and so forth.

What is claimed is:

1. A compound represented by formula (I):

Formula 1

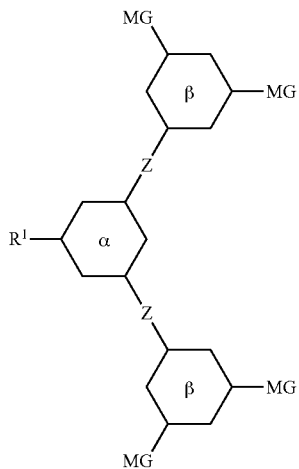

wherein, in formula (I), $R^1$ is fluorine, chlorine, or alkyl having 1 to 10 carbons, and in the alkyl, at least one of —$CH_2$— may be replaced by —O—, —S—, —CO— or —$SiH_2$—, and at least one of —$(CH_2)_2$— may be replaced by —CH=CH— or —C≡C—;

α and β are independently cyclohexane-1,3,5-triyl or benzene-1,3,5-triyl, and in the rings, —$CH_2$— may be replaced by —O—, —CH— may be replaced by —N—, and —$(CH_2)_2$— may be replaced by —CH=CH—, and in the rings, at least one of hydrogen may be replaced by fluorine, chlorine, —$CF_3$, —$CHF_2$, —$CH_2F$, —$OCF_3$, —$OCHF_2$ or —$OCH_2F$;

Z is a single bond or unbranched alkylene having 1 to 4 carbons, and in the alkylene, at least one of —$CH_2$— may be replaced by —O—, —CO—, —S— or —$SiH_2$—, at least one of —$(CH_2)_2$— may replaced by —CH=CH— or —C≡C—, and at least one of hydrogen may be replaced by fluorine; and MG is represented by formula (II):

Formula 2

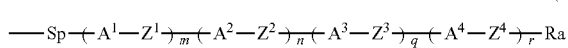

wherein, in formula (II), Sp is a single bond or unbranched alkylene having 1 to 10 carbons, and in the alkylene, at least one of —$CH_2$— may be replaced by —O—, —S—, —CO— or —$SiH_2$—, and at least one of —$(CH_2)_2$— may replaced by —CH=CH— or —C≡C—; Ra is independently fluorine, chlorine, or unbranched alkyl having 1 to 10 carbons, and in the alkyl, at least one of —$CH_2$— may be replaced by —O—, —S—, —CO— or —$SiH_2$—, and at least one of —$(CH_2)_2$— may be replaced by —CH=CH— or —C≡C—;

$A^1$, $A^2$, $A^3$ and $A^4$ are independently 1,4-cyclohexylene, 1,4-phenylene, cyclohexene-1,4-diyl, decahydronaphthalene-2,6-diyl, 1,2,3,4-tetrahydronaphthalene-2,6-diyl or naphthalene-2,6-diyl, and in the rings, one of —$CH_2$— may be replaced by —O—, —S—, —CO— or —$SiH_2$—, and at least one of —$(CH_2)_2$— may be replaced by —CH=CH—, and in the rings, at least one of hydrogen may be replaced by fluorine, chlorine, —$CF_3$, —$CHF_2$, —$CH_2F$, —$OCF_3$, —$OCHF_2$ or —$OCH_2F$;

$Z^1$, $Z^2$, $Z^3$ and $Z^4$ are independently a single bond or alkylene having 1 to 4 carbons, and in the alkylene, at least one of —$CH_2$— may be replaced by —O—, —S—, —CO— or —$SiH_2$—, at least one of —$(CH_2)_2$— may be replaced by —CH=CH— or —C≡C—, and at least one of hydrogen may be replaced by fluorine; and m, n, q and r are independently 0, 1 or 2, and a sum of m, n, q and r is 2, 3, 4 or 5.

2. The compound according to claim 1, wherein, in formula (I), $R^1$ is fluorine, alkyl having 1 to 10 carbons, alkenyl having 2 to 10 carbons, alkoxy having 1 to 9 carbons, alkoxyalkyl having 2 to 9 carbons, alkenyloxy having 3 to 9 carbons, polyfluoroalkyl having 1 to 10 carbons, polyfluoroalkoxy having 1 to 9 carbons, polyfluoroalkenyl having 2 to 10 carbons, or hydroxy-terminated alkyl having 1 to 10 carbons;

α and β are independently cyclohexane-1,3,5-triyl, 1,3,5-trioxane-2,4,6-triyl, benzene-1,3,5-triyl or 1,3,5-triazine-2,4,6-triyl; Z is a single bond, —$(CH_2)_2$—, —$CH_2O$—, —$OCH_2$—, —$CF_2O$—, —$OCF_2$—, —CH=CH—, —CF=CF—, —C≡C—, —COO—, —OCO—, —$CH_2SiH_2$—, —$SiH_2CH_2$—, —$(CH_2)_2COO$—, —$OCO(CH_2)_2$—, —$(CH_2)_2CF_2O$—, —$OCF_2(CH_2)_2$—, —$(CH_2)_3O$—, —$O(CH_2)_3$— or —$(CH_2)_4$—;

and in formula (II),

Sp is a single bond, unbranched alkylene having 1 to 10 carbons, alkenylene having 1 to 10 carbons, alkynylene having 1 to 10 carbons, oxyalkylene having 2 to 10 carbons, alkyleneoxy having 2 to 10 carbons or oxyalkyleneoxy having 3 to 10 carbons;

Ra is independently fluorine, alkyl having 1 to 10 carbons, alkenyl having 2 to 10 carbons, alkoxy having 1 to 9 carbons, alkoxyalkyl having 2 to 9 carbons, alkenyloxy having 3 to 9 carbons, polyfluoroalkyl having 1 to 10 carbons, polyfluoroalkoxy having 1 to 9 carbons or polyfluoroalkenyl having 2 to 10 carbons;

$A^1$, $A^2$, $A^3$ and $A^4$ are independently 1,4-cyclohexylene, 1,4-phenylene, cyclohexene-1,4-diyl, decahydronaphthalene-2,6-diyl, 1,2,3,4-tetrahydronaphthalene-2,6-diyl or naphthalene-2,6-diyl, and at least one of hydrogen may be replaced by fluorine, chlorine, —$CF_3$ or —$CHF_2$;

$Z^1$, $Z^2$, $Z^3$ and $Z^4$ are independently a single bond, —$(CH_2)_2$—, —COO—, —OCO—, —$CH_2O$—, —$OCH_2$—, —$CF_2O$—, —$OCF_2$—, —CH=CH—, —CF=CF—, —C≡C—, —$CH_2CO$—, —$COCH_2$—, —$CH_2SiH_2$—, —$SiH_2CH_2$—, —$(CH_2)_2COO$—, —$OCO(CH_2)_2$—, —$(CH_2)_2CF_2O$—, —$OCF_2(CH_2)_2$—, —$(CH_2)_3O$—, —$O(CH_2)_3$— or —$(CH_2)_4$—;

and m, n, q and r are independently 0 or 1, and a sum of m, n, q and r is 2, 3 or 4.

3. The compound according to claim 1, wherein, in formula (I), $R^1$ is fluorine, alkyl having 1 to 6 carbons, alkenyl having 2 to 6 carbons, alkoxy having 2 to 6 carbons, alkoxyalkyl having 2 to 6 carbons, alkenyloxy having 3 to 6 carbons, polyfluoroalkyl having 1 to 6 carbons, polyfluoroalkoxy having 1 to 6 carbons, polyfluoroalkenyl having 2 to 6 carbons or hydroxy-terminated alkyl having 1 to 6 carbons; α and β are benzene-1,3,5-triyl;

Z is a single bond, —(CH$_2$)$_2$—, —CH$_2$O—, —OCH$_2$—, —CF$_2$O—, —OCF$_2$—, —CH═CH—, —CF═CF—, —C≡C—, —COO— or —OCO—;

and in formula (II),

Sp is a single bond, unbranched alkylene having 1 to 10 carbons, alkenylene having 1 to 10 carbons, alkynylene having 1 to 10 carbons, oxyalkylene having 2 to 10 carbons, alkyleneoxy having 2 to 10 carbons or oxyalkyleneoxy having 3 to 10 carbons;

Formula 4

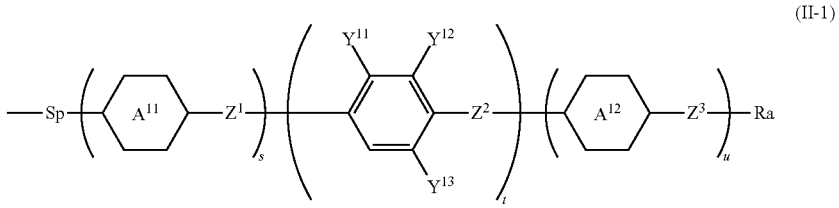

(II-1)

Ra is independently fluorine, alkyl having 1 to 6 carbons, alkenyl having 2 to 6 carbons, alkoxy having 1 to 6 carbons, polyfluoroalkyl having 1 to 6 carbons, polyfluoroalkoxy having 2 to 6 carbons or polyfluoroalkenyl having 2 to 6 carbons;

A$^1$, A$^2$, A$^3$ and A$^4$ are independently 1,4-cyclohexylene, 1,4-phenylene, cyclohexene-1,4-diyl, 2-fluoro-1,4-phenylene, 2,3-difluoro-1,4-phenylene, 3,5-difluoro-1,4-phenylene, 2,5-difluoro-1,4-phenylene, 2-fluoro-3-trifluoromethyl-1,4-phenylene or 2-fluoro-3-difluoromethyl-1,4-phenylene;

Z$^1$, Z$^2$, Z$^3$ and Z$^4$ are independently a single bond, —(CH$_2$)$_2$—, —CH$_2$O—, —OCH$_2$—, —CF$_2$O—, —OCF$_2$—, —CH═CH—, —CF═CF—, —C≡C—, —(CH$_2$)$_2$CF$_2$O—, —OCF$_2$(CH$_2$)$_2$—, —(CH$_2$)$_3$O—, —O(CH$_2$)$_3$— or —(CH$_2$)$_4$—; and m, n, q and r are independently 0 or 1, and a sum of m, n, q and r is 2, 3 or 4.

4. The compound according to claim 2, represented by formula (I-1):

Formula 3

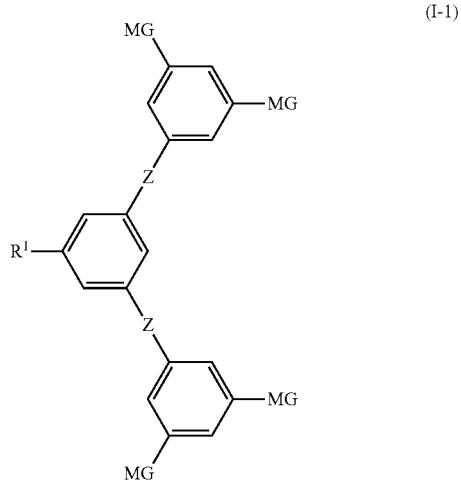

(I-1)

wherein, in formula (I-1), R$^1$ is fluorine, alkyl having 1 to 6 carbons, alkenyl having 2 to 6 carbons, alkoxy having 2 to 6 carbons, alkoxyalkyl having 2 to 6 carbons, alkenyloxy having 3 to 6 carbons, polyfluoroalkyl having 1 to 6 carbons, polyfluoroalkoxy having 1 to 6 carbons, polyfluoroalkenyl having 2 to 6 carbons or hydroxy-terminated alkyl having 1 to 6 carbons;

Z is a single bond, —(CH$_2$)$_2$—, —CH$_2$O—, —OCH$_2$—, —CF$_2$O—, —OCF$_2$—, —CH═CH—, —CF═CF— or —C≡C—; and MG is represented by formula (II-1):

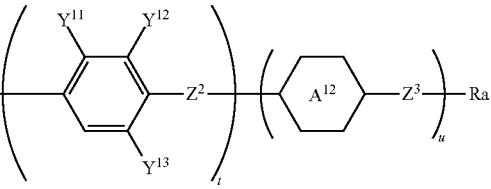

wherein, in formula (II-1), Sp is a single bond, unbranched alkylene having 1 to 10 carbons, alkenylene having 2 to 10 carbons, alkynylene having 2 to 10 carbons, oxyalkylene having 1 to 9 carbons, alkyleneoxy having 1 to 9 carbons or oxyalkyleneoxy having 1 to 8 carbons;

Ra is independently fluorine, alkyl having 1 to 6 carbons, alkenyl having 2 to 6 carbons, alkoxy having 1 to 5 carbons, polyfluoroalkyl having 1 to 6 carbons, polyfluoroalkoxy having 1 to 5 carbons or polyfluoroalkenyl having 2 to 6 carbons;

A$^{11}$ and A$^{12}$ are 1,4-cyclohexylene or 1,4-phenylene;

Y$^{11}$, Y$^{12}$ and Y$^{13}$ are independently hydrogen, fluorine, —CF$_3$ or —CF$_2$H;

Z$^1$, Z$^2$ and Z$^3$ are independently a single bond, —(CH$_2$)$_2$—, —CH$_2$O—, —OCH$_2$—, —CF$_2$O—, —OCF$_2$—, —CH═CH—, —CF═CF— or —C≡C—; and s and u are independently 0, 1 or 2, t is always 1, and a sum of s, t and u is 2, 3 or 4.

5. The compound according to claim 4, wherein, in formula (I-1), R$^1$ is alkyl having 1 to 3 carbons, alkenyl having 2 to 3 carbons, alkoxy having 2 to 3 carbons or hydroxy-terminated alkyl having 1 to 3 carbons; and Z is a single bond, —(CH$_2$)$_2$—, —CH$_2$O—, —OCH$_2$—, —CH═CH— or C≡C—.

6. The compound according to claim 5, wherein, in formula (II-1), Sp is a single bond, unbranched alkylene having 1 to 8 carbons, alkenylene having 2 to 8 carbons, alkynylene having 2 to 8 carbons, oxyalkylene having 1 to 7 carbons, alkyleneoxy having 1 to 7 carbons or oxyalkyleneoxy having 1 to 6 carbons; Ra is independently fluorine, polyfluoroalkyl having 1 to 6 carbons, polyfluoroalkoxy having 2 to 6 carbons or polyfluoroalkenyl having 2 to 6 carbons; A$^{11}$ and A$^{12}$ are 1,4-cyclohexylene or 1,4-phenylene; Y$^{11}$ is hydrogen, Y$^{12}$ and Y$^{13}$ are independently hydrogen or fluorine, but at least one is fluorine; Z$^1$, Z$^2$ and Z$^3$ are independently a single bond, —(CH$_2$)$_2$—, —CF$_2$O—, —CH═CH—, —CF═CF— or —C≡C—; and a sum of s, t and u is 2 or 3.

7. The compound according to claim 5, wherein, in formula (II-1), Sp is a single bond, unbranched alkylene having 1 to 8 carbons, alkenylene having 2 to 8 carbons, alkynylene having 2 to 8 carbons, oxyalkylene having 1 to 7 carbons, alkyleneoxy having 1 to 7 carbons or oxyalkyleneoxy having 1 to 6 carbons; Ra is independently alkyl having 1 to 6 carbons, alkenyl having 2 to 6 carbons or alkoxy having 1 to 5 carbons; A$^{11}$ and A$^{12}$ are 1,4-cyclohexylene or 1,4-phenylene; Y$^{11}$ and $Y^{12}$ are fluorine and $Y^{13}$ is hydrogen; $Z^1$, $Z^2$ and $Z^3$ are independently a single bond, $-(CH_2)_2-$, $-CH_2O-$, $-OCH_2-$, $-CH=CH-$, $-CF=CF-$ or $-C\equiv C-$; and a sum of s, t and u is 2 or 3.

8. The compound according to claim 5, wherein, in formula (II-1), Sp is a single bond, unbranched alkylene having 1 to 8 carbons, alkenylene having 2 to 8 carbons, alkynylene having 2 to 8 carbons, oxyalkylene having 1 to 7 carbons, alkyleneoxy having 1 to 7 carbons or oxyalkyleneoxy having 1 to 6 carbons; Ra is independently alkyl having 1 to 6 carbons, alkenyl having 2 to 6 carbons or alkoxy having 1 to 5 carbons; $A^{11}$ and $A^{12}$ are 1,4-cyclohexylene or 1,4-phenylene; $Y^{11}$ and $Y^{13}$ are independently hydrogen or fluorine, and $Y^{12}$ is hydrogen; $Z^1$, $Z^2$ and $Z^3$ are independently a single bond, $-(CH_2)_2-$, $-CH=CH-$, $-CF=CF-$ or $-C\equiv C-$; and a sum of s, t and u is 2 or 3.

9. The compound according to claim 5, wherein, in formula (I-1), MG is represented by any one of formula (II-1-1-1) to formula (II-1-1-16):

Formula 5

(II-1-1-1)
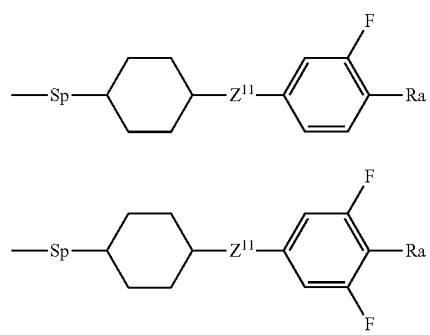

(II-1-1-2)

(II-1-1-3)

(II-1-1-4)
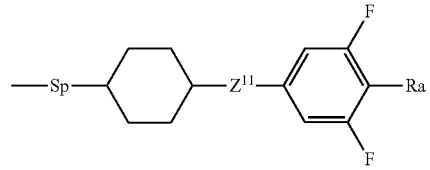

(II-1-1-5)

(II-1-1-6)
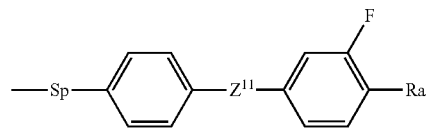

(II-1-1-7)
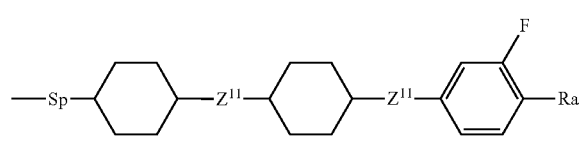

(II-1-1-8)

(II-1-1-9)

(II-1-1-10)
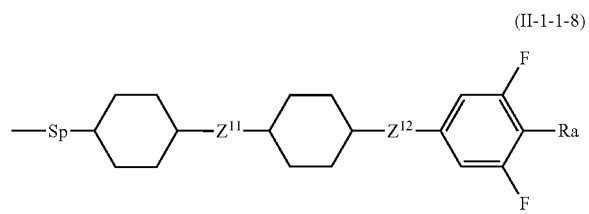

(II-1-1-11)

(II-1-1-12)
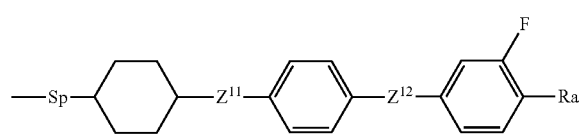

(II-1-1-13)

(II-1-1-14)
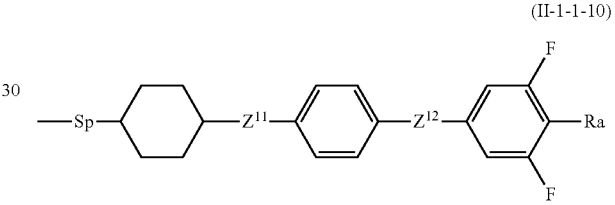

153
-continued (II-1-1-15)
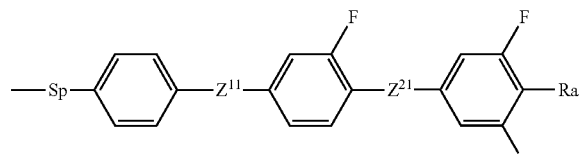

(II-1-1-16)
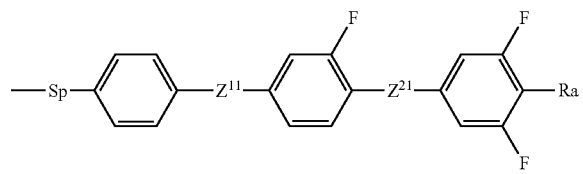

wherein, in formula (II-1-1-1) to formula (II-1-1-16), Sp is a single bond, unbranched alkylene having 1 to 8 carbons, alkenylene having 2 to 8 carbons, alkynylene having 2 to 8 carbons, oxyalkylene having 1 to 7 carbons, alkyleneoxy having 1 to 7 carbons or oxyalkyleneoxy having 1 to 6 carbons; Ra is independently fluorine, —CF$_3$, —CF$_2$H or —OCF$_3$; and Z$^{11}$, Z$^{12}$ and Z$^{21}$ are independently a single bond, —(CH$_2$)$_2$—, —CF$_2$O—, —CH=CH—, —CF=CF— or —C≡C—.

10. The compound according to claim 5, wherein, in formula (I-1), MG is represented by any one of formula (II-1-2-1) to formula (II-1-2-14):

Formula 6

(II-1-2-1)
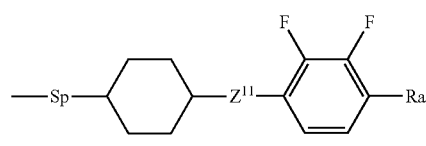

(II-1-2-2)
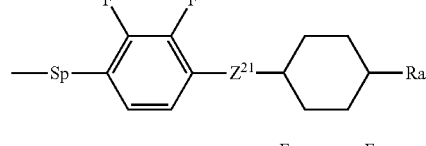

(II-1-2-3)
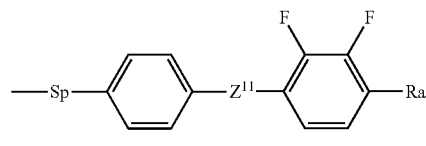

(II-1-2-4)
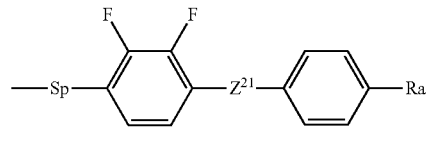

(II-1-2-5)
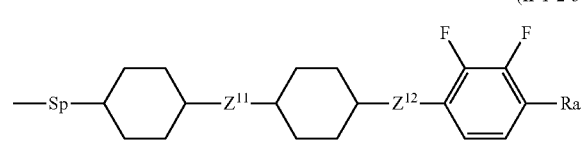

154
-continued (II-1-2-6)
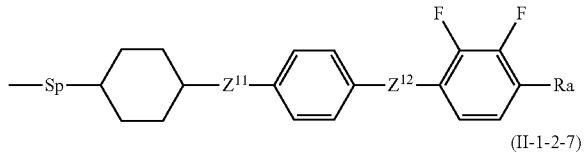

(II-1-2-7)
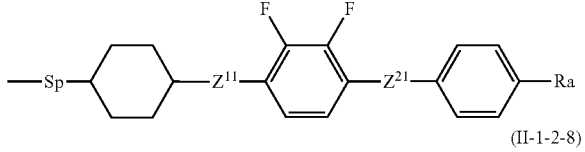

(II-1-2-8)
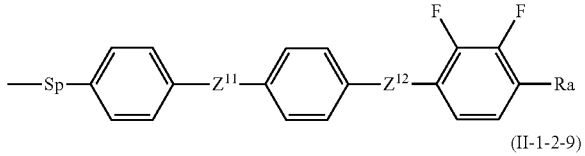

(II-1-2-9)
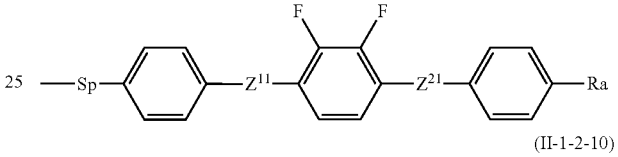

(II-1-2-10)
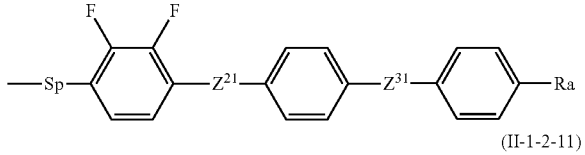

(II-1-2-11)
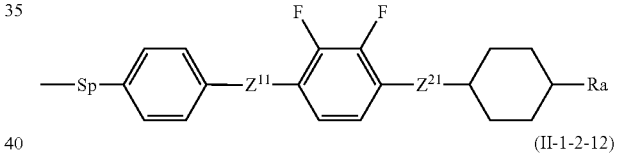

(II-1-2-12)
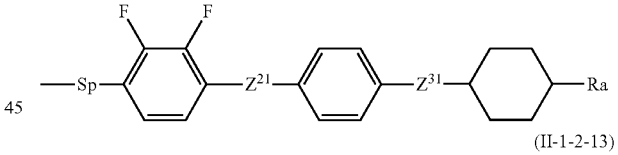

(II-1-2-13)
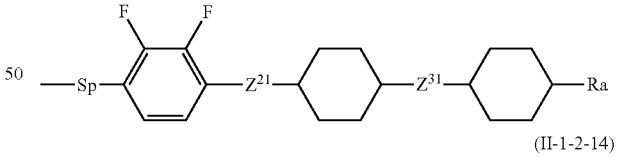

(II-1-2-14)
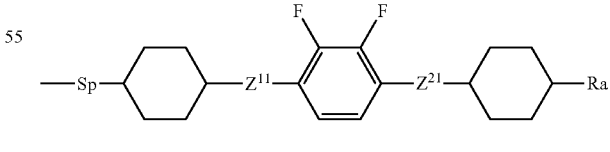

wherein, in formula (II-1-2-1) to formula (II-1-2-14), Sp is a single bond, unbranched alkylene having 1 to 8 carbons, alkenylene having 2 to 8 carbons, alkynylene having 2 to 8 carbons, oxyalkylene having 2 to 6 carbons, alkyleneoxy having 2 to 6 carbons or oxyalkyleneoxy having 3 to 6 carbons; Ra is independently alkyl having 1 to 6 carbons, alkenyl having 2 to 6 carbons or alkoxy having 1 to 6 carbons; and $Z^{11}$, $Z^{12}$, $Z^{21}$ and $Z^{31}$ are independently a single bond, —(CH$_2$)$_2$—, —CH$_2$O—, —OCH$_2$—, —CH=CH—, —CF=CF— or —C≡C—.

11. The compound according to claim 5, wherein, in formula (I-1), MG is represented by any one of formula (II-1-3-1) to formula (II-1-3-17):

Formula 7

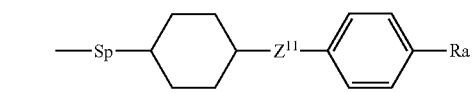
(II-1-3-1)

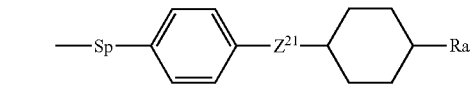
(II-1-3-2)

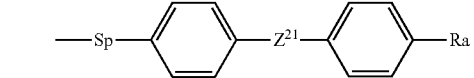
(II-1-3-3)

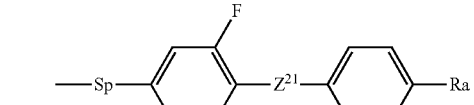
(II-1-3-4)

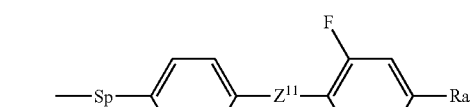
(II-1-3-5)

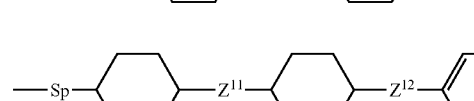
(II-1-3-6)

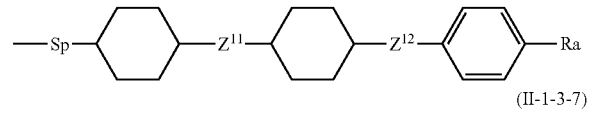
(II-1-3-7)

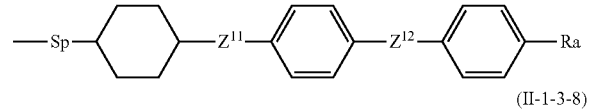
(II-1-3-8)

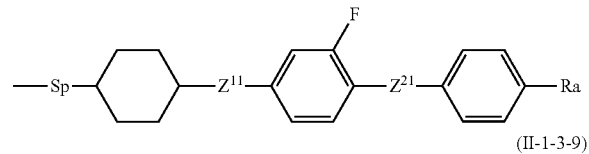
(II-1-3-9)

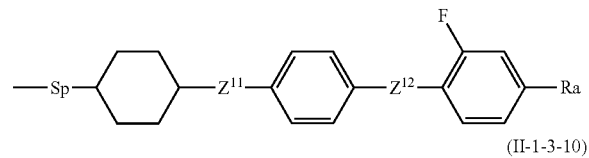
(II-1-3-10)

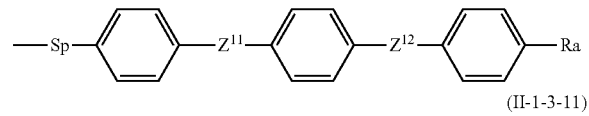
(II-1-3-11)

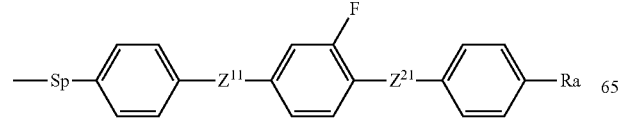
(II-1-3-12)

-continued

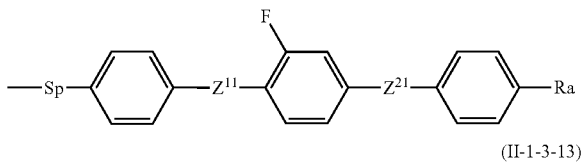
(II-1-3-13)

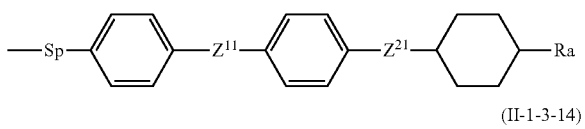
(II-1-3-14)

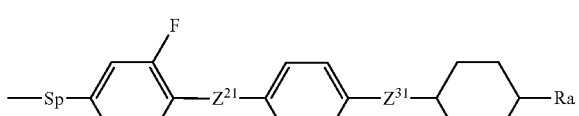
(II-1-3-15)

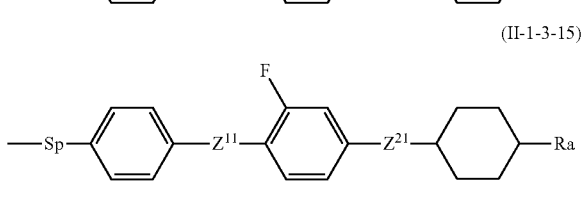
(II-1-3-16)

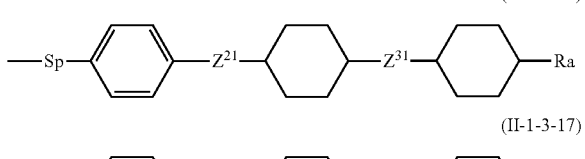
(II-1-3-17)

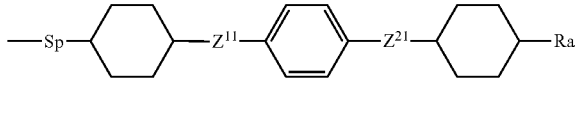

wherein, in formula (II-1-3-1) to formula (II-1-3-17), Sp is a single bond, unbranched alkylene having 1 to 8 carbons, alkenylene having 2 to 8 carbons, alkynylene having 2 to 8 carbons, oxyalkylene having 2 to 6 carbons, alkyleneoxy having 2 to 6 carbons or oxyalkyleneoxy having 3 to 6 carbons; Ra is independently alkyl having 1 to 6 carbons, alkenyl having 2 to 6 carbons or alkoxy having 1 to 6 carbons; and $Z^{11}$, $Z^{12}$, $Z^{21}$ and $Z^{31}$ are independently a single bond, —(CH$_2$)$_2$—, —CH$_2$O—, —OCH$_2$—, —CH=CH—, —CF=CF— or —C≡C—.

12. A liquid crystal composition containing at least one compound represented by formula (1) according to claim 1.

13. The liquid crystal composition according to claim 12, containing at least one of compound (1) and at least one compound represented by formula (2), (3) or (4):

Formula 8

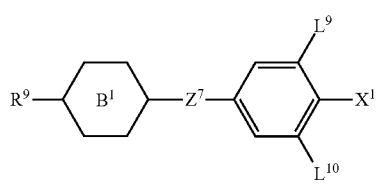
(2)

-continued

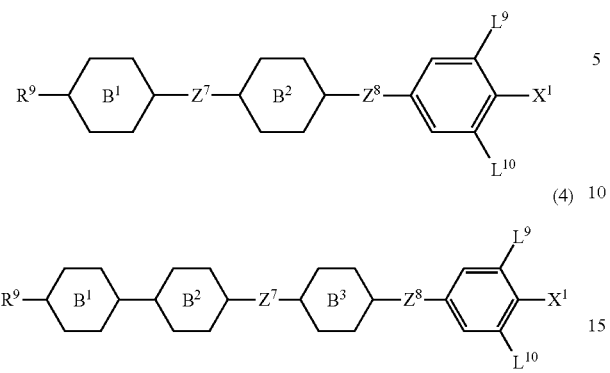

(3)

(4)

wherein, in formulas (2) to (4), R⁹ is independently alkyl having 1 to 10 carbons or alkenyl having 2 to 10 carbons, and in the alkyl and the alkenyl, at least one of hydrogen may be replaced by fluorine, and at least one of —CH₂— may be replaced by —O—;
X¹ is fluorine, chlorine, —OCF₃, —OCHF₂, —CF₃, —CHF₂, —CH₂F, —OCF₂CHF₂ or —OCF₂CHFCF₃;
ring B¹, ring B² and ring B³ are independently 1,4-cyclohexylene, 1,3-dioxane-2,5-diyl, pyrimidine-2,5-diyl, 1-tetrahydropyran-2,5-diyl, 1,4-phenylene, 2-fluoro-1,4-phenylene, 3-fluoro-1,4-phenylene or 3,5-difluoro-1,4-phenylene;
Z⁷ and Z⁸ are independently —(CH₂)₂—, —(CH₂)₄—, —COO—, —CF₂O—, —OCF₂—, —CH=CH—, —C≡C—, —CH₂O— or a single bond; and
L⁹ and L¹⁰ independently ndependently hydrogen or fluorine.

Formula 10

14. The liquid crystal composition according to claim 12, containing at least one of compound (1) and at least one of compound represented by formula (5):

Formula 9

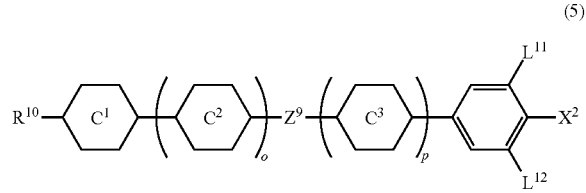

(5)

wherein, in formula (5), R¹⁰ is alkyl having 1 to 10 carbons or alkenyl having 2 to 10 carbons, and in the alkyl and the alkenyl, at least one of hydrogen may be replaced by fluorine, and at least one of —CH₂— may be replaced by —O—;
X² is —C≡N or —C≡C—C≡N;
ring C¹, ring C² and ring C³ are independently 1,4-cyclohexylene, 1,4-phenylene in which at least one of hydrogen may be replaced by fluorine, 1,3-dioxane-2,5-diyl, 1-tetrahydropyran-2,5-diyl or pyrimidine-2,5-diyl;
Z⁹ is —(CH₂)₂—, —COO—, —CF₂O—, —OCF₂—, —C≡C—, —CH₂O— or a single bond;
L¹¹ and L¹² are independently hydrogen or fluorine; and
o is 0, 1 or 2, p is 0 or 1, and a sum of o and p is 0, 1, 2 or 3.

15. The liquid crystal composition according to claim 12, containing at least one of compound (1) and at least one compound represented by any one of formulas (6) to (11):

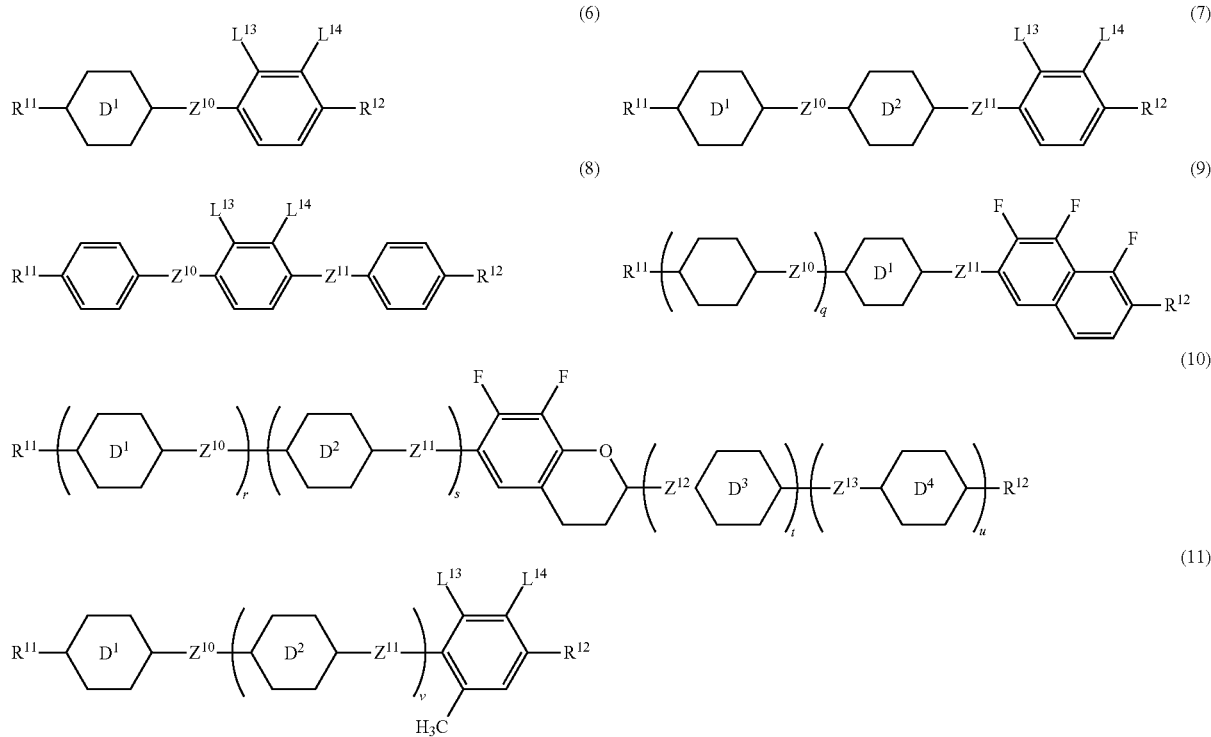

wherein, in formulas (6) to (11), $R^{11}$ and $R^{12}$ are independently alkyl having 1 to 10 carbons or alkenyl having 2 to 10 carbons, and in the alkyl and the alkenyl, at least one of hydrogen may be replaced by fluorine, and at least one of —$CH_2$— may be replaced by —O—;

ring $D^1$, ring $D^2$, ring $D^3$ and ring $D^4$ are independently 1,4-cyclohexylene, 1,4-cyclohexenylene, 1,4-phenylene in which at least one of hydrogen may be replaced by fluorine, 6-tetrahydropyran-2,5-diyl or decahydro-2,6-naphthalene;

$Z^{10}, Z^{11}, Z^{12}$ and $Z^{13}$ are independently —$(CH_2)_2$—, —COO—, —$CH_2O$—, —$OCF_2$—, —$OCF_2(CH_2)_2$— or a single bond;

$L^{13}$ and $L^{14}$ are independently fluorine or chlorine; and q, r, s, t, u and v are independently 0 or 1, and a sum of r, s, t and u is 1 or 2.

16. The liquid crystal composition according to claim 12, containing at least one of compound (1) and at least one of compounds represented by formula (12), (13) or (14):

Formula 11

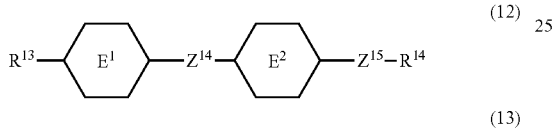
(12)

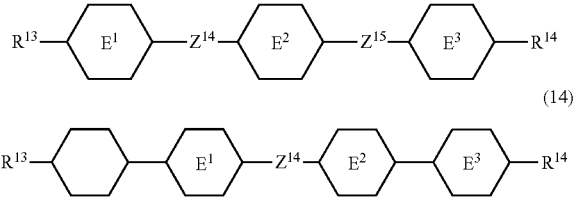
(13)

(14)
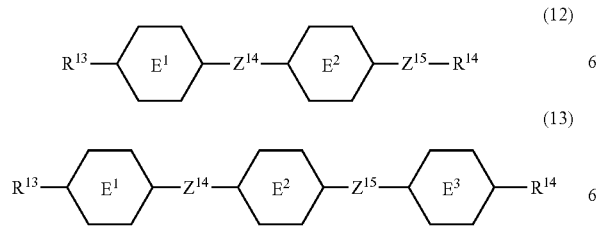

wherein, in formulas (12) to (14), $R^{13}$ and $R^{14}$ are independently alkyl having 1 to 10 carbons or alkenyl having 2 to 10 carbons, and in the alkyl and the alkenyl, at least one of —$CH_2$—may be replaced by —O—;

ring $E^1$, ring $E^2$ and ring $E^3$ are independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and $Z^{14}$ and $Z^{15}$ are independently —C≡C—, —COO—, —$(CH_2)_2$—, —CH=CH— or a single bond.

17. The liquid crystal composition according to claim 13, further containing at least one compound represented by formula (5).

18. The liquid crystal composition according to claim 13, further containing at least one compound represented by formula (12), (13) or (14):

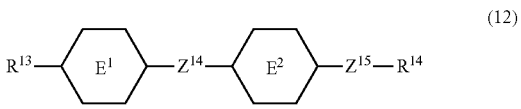
(12)

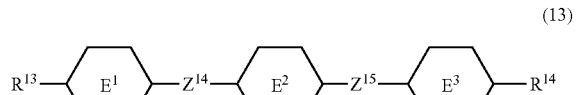
(13)

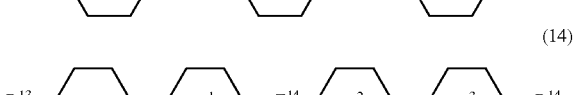
(14)

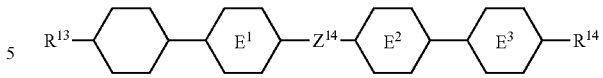

wherein, in formulas (12) to (14), $R^{13}$ and $R^{14}$ independently ndependently alkyl having 1 to 10 carbons or alkenyl having 2 to 10 carbons, and in the alkyl and the alkenyl, at least one of —$CH_2$—may be replaced by —O—;

ring $E^1$, ring $E^2$ and ring $E^3$ are independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and $Z^{14}$ and $Z^{15}$ are independently —C≡C—, —COO—, —$(CH_2)_2$—, —CH=CH— or a single bond.

19. The liquid crystal composition according to claim 14, further containing at least one compound represented by formula (12), (13) or (14):

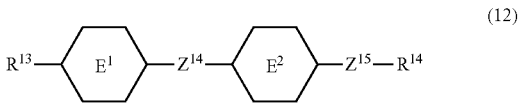
(12)

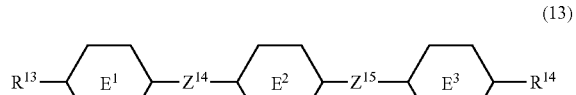
(13)

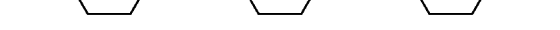
(14)

wherein, in formulas (12) to (14), $R^{13}$ and $R^{14}$ independently ndependently alkyl having 1 to 10 carbons or alkenyl having 2 to 10 carbons, and in the alkyl and the alkenyl, at least one of —$CH_2$—may be replaced by —O—;

ring $E^1$, ring $E^2$ and ring $E^3$ are independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and $Z^{14}$ and $Z^{15}$ are independently —C≡C—, —COO—, —$(CH_2)_2$—, —CH=CH— or a single bond.

20. The liquid crystal composition according to claim 15, further containing at least one compound represented by formula (12), (13) or (14):

-continued

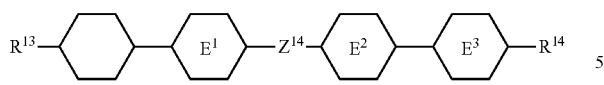
(14)

wherein, in formulas (12) to (14), $R^{13}$ and $R^{14}$ independently ndependently alkyl having 1 to 10 carbons or alkenyl having 2 to 10 carbons, and in the alkyl and the alkenyl, at least one of —$CH_2$— may be replaced by —O—;

ring $E^1$, ring $E^2$ and ring $E^3$ are independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and $Z^{14}$ and $Z^{15}$ are independently —C≡C—, —COO—, —$(CH_2)_2$—, —CH=CH— or a single bond.

21. The liquid crystal composition according to claim 12, further containing at least one optically active compound or at least one polymerizable compound.

22. The liquid crystal composition according to claim 12, further containing at least one antioxidant or at least one ultraviolet light absorber.

23. A liquid crystal display device including the liquid crystal composition according to claim 12.

* * * * *